United States Patent
Schlumpf et al.

(10) Patent No.: US 11,389,513 B2
(45) Date of Patent: *Jul. 19, 2022

(54) COLLAGEN PEPTIDE-BASED MEDICAMENT COMPOSITIONS AND DEVICES AND METHODS OF PRODUCTION AND USE THEREOF

(71) Applicant: SUSTAIN HOLDINGS, LLC, Stuart, FL (US)

(72) Inventors: Richard E. Schlumpf, Stuart, FL (US); Robert Baratta, Palm City, FL (US); Shawn Delorey, Charlotte, NC (US); David J. Calkins, Nashville, TN (US)

(73) Assignee: SUSTAIN HOLDINGS, LLC, Stuart, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/855,097

(22) Filed: Apr. 22, 2020

(65) Prior Publication Data

US 2020/0353056 A1 Nov. 12, 2020

Related U.S. Application Data

(60) Provisional application No. 62/959,282, filed on Jan. 10, 2020, provisional application No. 62/933,685, filed on Nov. 11, 2019, provisional application No. 62/836,934, filed on Apr. 22, 2019.

(51) Int. Cl.
*A61K 38/39* (2006.01)
*A61P 27/02* (2006.01)
*A61K 9/00* (2006.01)

(52) U.S. Cl.
CPC ............ *A61K 38/39* (2013.01); *A61K 9/0019* (2013.01); *A61K 9/0048* (2013.01); *A61P 27/02* (2018.01)

(58) Field of Classification Search
None
See application file for complete search history.

(56) References Cited

U.S. PATENT DOCUMENTS

| | | | |
|---|---|---|---|
| 5,120,764 A | 6/1992 | McCarthy et al. |
| 5,201,456 A | 4/1993 | Reynal et al. |
| 5,252,608 A | 10/1993 | Palfreyman et al. |
| 5,973,112 A | 10/1999 | Raines et al. |
| 6,197,934 B1 | 3/2001 | DeVore et al. |
| 6,448,378 B2 | 9/2002 | DeVore et al. |
| 6,946,440 B1 | 9/2005 | DeWoolfson et al. |
| 7,122,521 B2 | 10/2006 | Raines et al. |
| 7,402,562 B2 | 7/2008 | DeWoolfson et al. |
| 7,858,741 B2 | 12/2010 | Raines et al. |
| 8,283,414 B2 | 10/2012 | Yu et al. |
| 8,461,303 B2 | 6/2013 | Smith et al. |
| 8,658,167 B2 | 2/2014 | Smith et al. |
| 8,680,246 B2 | 3/2014 | McCauley et al. |
| 8,883,964 B2 | 11/2014 | Yu et al. |
| 9,176,139 B2 | 11/2015 | Smith et al. |
| 9,255,086 B2 | 2/2016 | Arora et al. |
| 9,289,396 B2 | 3/2016 | Devore et al. |
| 9,289,447 B2 | 3/2016 | Smith et al. |
| 9,399,102 B2 | 7/2016 | Dewoolfson et al. |
| 9,623,129 B2 | 4/2017 | Gonzales et al. |
| 9,758,569 B2 | 9/2017 | Raines et al. |
| 9,988,434 B2 | 6/2018 | Raines et al. |
| 10,632,168 B2 * | 4/2020 | Schlumpf ............. A61L 31/044 |
| 2007/0275897 A1 | 11/2007 | Raines et al. |
| 2008/0287342 A1 | 11/2008 | Yu et al. |

(Continued)

FOREIGN PATENT DOCUMENTS

| | | | |
|---|---|---|---|
| WO | 2016/165788 A1 | 10/2016 |
| WO | 2018187530 A1 | 10/2018 |
| WO | WO-2018187530 A1 * | 10/2018 | ............. A61L 27/24 |

OTHER PUBLICATIONS

Mix K "Chemical Methods for Protein Modification and Cellular Delivery" Doctoral Dissertation. 276 pages. University of Wisconsin-Madison. (Year: 2017).*
Albu et al., "Collagen-Based Drug Delivery Systems for Tissue Engineering", in: Biomaterials Applications for Nanomedicine, Prof. Pignatello, R. (Ed.), 2011, ISBN: 978-953-307-661-4, DOI: 10.5772/22981, Rijeka, Croatia: InTech, available from https://www.intechopen.com/books/biomaterials-applications-for-nanomedicine/collagen-based-drug-delivery-systems-for-tissue-engineering.
An et al., "Collagen interactions: Drug design and delivery," Advanced Drug Delivery Reviews (2016) 97:69-84.
Bala et al., "PLGA nanoparticles in drug delivery: the state of the art.," Critical Reviews in Therapeutic Drug Carrier Systems (2004) 21(5):387-422.
Bautista et al., "Insulin-like growth factors I and II are present in the skeletal tissues often vertebrates," Metabolism (1990) 39(1):96-100.

(Continued)

*Primary Examiner* — Sudhakar Katakam
*Assistant Examiner* — Zachary J Miknis
(74) *Attorney, Agent, or Firm* — Medler Ferro Woodhouse & Mills PLLC

(57) ABSTRACT

The present invention is in the fields of medicinal chemistry, biotechnology and pharmaceuticals. The invention provides compositions comprising one or more collagen mimetic peptides, optionally attached to one or more therapeutic compounds or one or more imaging compounds, for use in methods of treating, preventing, ameliorating, curing and diagnosing certain diseases and physical disorders in humans and veterinary animals, particularly anterior and posterior segment ocular diseases and physical disorders, paraocular and extraocular diseases and physical disorders, and nerve or nervous system diseases and physical disorders, as well as methods of manufacturing such compositions. The invention also provides medical devices comprising one or more such compositions of the invention. The invention also provides methods of use of such compositions and devices in treating and diagnosing certain diseases and physical disorders in humans and veterinary animals, including anterior and posterior segment ocular diseases or disorders, paraocular and extraocular diseases and physical disorders, and nerve or nervous system diseases or disorders.

13 Claims, 16 Drawing Sheets

Specification includes a Sequence Listing.

(56) References Cited

U.S. PATENT DOCUMENTS

| | | | |
|---|---|---|---|
| 2011/0118349 | A1 | 5/2011 | Garrigue et al. |
| 2012/0195828 | A1 | 8/2012 | Nakamura et al. |
| 2013/0129807 | A1 | 5/2013 | Devore et al. |
| 2013/0164220 | A1 | 6/2013 | Yu et al. |
| 2015/0111308 | A1 | 4/2015 | Yu et al. |
| 2015/0209472 | A1 | 7/2015 | McCoy |
| 2016/0075764 | A1 | 3/2016 | Raines et al. |
| 2016/0215018 | A1 | 7/2016 | Yang et al. |
| 2018/0111979 | A1 | 4/2018 | Phopase |
| 2018/0325977 | A1* | 11/2018 | Schlumpf ............. A61K 9/0014 |
| 2019/0002531 | A1* | 1/2019 | Popel ..................... C07K 14/78 |
| 2020/0246415 | A1* | 8/2020 | Schlumpf ............. A61K 38/39 |

OTHER PUBLICATIONS

Besseau et al., "Stabilization of Fluid Cholesteric Phases of Collagen to Ordered Gelated Matrices", J. Mol. Biol. (1995) 251:197-202.

Bondareva et al., "The Lysyl Oxidase Inhibitor, β-Aminopropionitrile, Diminishes the Metastatic Colonization Potential of Circulating Breast Cancer Cells," PLoS One (2009) 4(6):e5620.

Bradley, "Some mechanical property considerations of reconstituted collagen for drug release supports", Biomaterials, Medical Devices, and Artificial Organs (1997) 5(2):159-175.

Buechter et al., "Co-translational Incorporation of Trans-4-Hydroxyproline into Recombinant Proteins in Bacteria," Journal of Biological Chemistry (2003) 278(1):645-650.

Carlson et al., "Impact of Hyaluronic Acid-Containing Artificial Tear Products on Reepithelialization in an In Vivo Corneal Wound Model," Journal of Ocular Pharmacology and Theapeutics, published online Feb. 2, 2018, accessed at https://doi.org/10.1089/jop.2017.0080.

Cavallaro et al., "Collagen Fabrics as Biomaterials", Biotechnology and Bioengineering (1994) 43:781-791.

Chak et al., "A Review of Collagen Based Drug Delivery Systems," International Journal of Pharmacy & Teaching and Practices (2013) 4(4):811-820.

Chan et al., "Photochemical crosslinking improves the physicochemical properties of collagen scaffolds", J. Biomed. Mater. Res. (2005) 75A:689-701.

Chattopadhyay et al., "Anchoring a Cytoactive Factor in a Wound Bed Promotes Healing," Journal of Tissue Engineering Regenerative Medicine (2014) 10(12):1012-1020.

Chattopadhyay et al., "Peptides that anneal to natural collagen in vitro and ex vivo.," Organic & Biomolecular Chemistry (2012) 10(30):5892-5897.

Chattopadhyay et al., "Collagen-based biomaterials for wound healing," Biopolymers (2014)101(8):821-833.

Chung et al., "Collagenase unwinds triple-helical collagen prior to peptide bond hydrolysis," The EMBO Journal (2004) 23(15):3020-3030.

Cooperman et al., "The immunogenicity of injectable collagen. I. A 1-year prospective study," Journal of the American Academy of Dermatology (1984) 10(4):636-646.

Coudrillier et al., "Glaucoma-related Changes in the Mechanical Properties and Collagen Micro-architecture of the Human Sclera," PLoS One (2015) (10):e0131396.

Davis et al., "Regulation of Tissue Injury Responses by the Exposure of Matricryptic Sites within Extracellular Matrix Molecules," American Journal of Patholofy (2000) 156(5):1489-1498.

Del Bouno et al., "Procol™, a New Technology for Drug Delivery," Sustain Biotechnology.

Dua et al., "The collagen matrix of the human trabecular meshwork is an extension of the novel pre-Descemet's layer (Dua's layer)," British Journal of Ophthalmology (2014) 98(5):691-697.

Ellison et al., "Convenient Synthesis of Collagen-Related Tripeptides for Segment Condensation," Peptide Science (2015) 104(6):676-681.

Epstein, Howard, "Cosmeceutical Vehicles," Clininical Dermatology (2009) 27(5):453-460.

Erler et al., "Hypoxia-induced lysyl oxidase is a critical mediator of bone marrow cell recruitment to form the pre-metastatic niche," Cancer Cell (2009) 15(1):35-44.

Erler, J.T., et al., "Lysyl oxidase is essential for hypoxia-induced metastasis," Nature (2006) 440(27):1222-1226.

Fallas, et al., "Synthetic collagen mimics: self-assembly of homotrimers, heterotrimers and higher order structures," Chem Soc Rev (2010) 39:3510-3527.

Fang et al., "Collagen as a double-edged sword in tumor progression," Tumour Biology: The Journal of the International Society for Oncodevelopmental Biology and Medicine (2014) 35(4):2871-2882.

FDA Drug Safety Communication: FDA updates warnings for oral and injectable fluoroquinolone antibiotics due to disabling side effects, accessed Nov. 6, 2017, at https://www.fda.gov/Drugs/DrugSafety/ucm511530.htm.

Fleischmajer et al., "Dermal collagen fibrils are hybrids of type 1 and type 3 collagen molecules," Journal of Strutural Biology (1990) 105:162-169.

Frenkel et al., "Chondrocyte transplantation using a collagen bilayer matrix for cartilage repair," The Journal of Bone and Joint Surgery (1997) 79-B:831-836.

Gaudana et al., "Ocular Drug Delivery," The AAPS Journal (2010) 12(3):348-360.

Garg et al., "To Study the Efficacy of Difluprednate Opthalmic Emulsion and Prednisolone Acetate Opthalmic Suspension on Postoperative Inflammation in Cataract Surgery," Journal of Clinical and Diagnostic Research (2016) 10(12):NC05-NC08.

Gelse et al., "Collagens—structure, function, and biosynthesis," Advanced Drug Delivery Reviews (2003) 55(12):1531-1546.

Giusti et al., "Collagen-based new bioartificial polymeric materials," Biomaterials (1994) 15(15):1229-1233.

Gottlieb et al., "Self-Assembled collagen-like peptide fibers as templates for metallic nanowires," Journal of Materials Chemistry (2008) 18:3865-3870.

Grabarek et al., "Zero-length crosslinking procedure with the use of active esters," Analytical Biochemistry (1990) 185:131-135.

Granchi et al., "Bioreductively Activated Lysyl Oxidase Inhibitors against Hypoxic Tumours," ChemMedChem (2009) 4(10):1590-1594.

Hay, Elizabeth D., "Extracellular matrix," Journal of Cell Biology (1981) 91(3):205-223.

Hodges et al., "Stereoelectronic and Steric Effects in the Collagen Triple Helix: Toward a Code for Strand Association," J. A,. Chem. Soc. (2005) 127:15923-15932.

Hong et al., "Collagenase-Mediated Tissue Modeling of Corneal Ectasia and Collagen Cross-Linking Treatments," Investigative Ophthalmology & Visual Science (2012) 53(4):2321-2327.

Huang et al., "Collagen: A potential factor involved in the pathogenesis of glaucoma," Medical Science Monitor Basic Research (2013) 19:237-240.

Hulmes, D.J.S., "Collagen Diversity, Synthesis and Assembly," in: Collagen: Structure and Mechanics (2008) pp. 15-47.

Jangamreddy et al., "Short peptide analogs as alternatives to collagen in pro-regenerative corneal implants," Acta Biomaterialia (2018) 69:120-130.

Jones et al., "Analysis of structural design-features in collagen," Journal of Molecular Biology (1991) 218:209-219.

Joseph et al., "Drug delivery to the eye: what benefits to nanocarriers offer?," Nanomedicine (Lond.) (2017) 12(6):683-702.

Karthikeyan et al., "The concept of ocular inserts as drug delivery systems: An overview," Asian Journal of Pharmaceutics (2008) 2(4):192-200.

Kelkar et al., "Theranostics: combining imaging and therapy," Bioconjugate Chem (2011) 22:1879-1903.

Kolenik et al., "Use of a Lyophilized Bovine Collagen Matrix in Postoperative Wound Healing," Dermatol Surg (1999) 25:303-307.

Kumar et al., "A Nanostructured Synthetic Collagen Mimic for Hemostasis," Biomacromolecules (2014) 15:1484-1490.

Kumar et al., "Polymer Gels: Perspectives and Applications," Springer (2018).

(56) References Cited

OTHER PUBLICATIONS

Lauer et al., "Collagen in Cancer," In: The Tumor Microenvironment, Springer-Verlag New York (2010) p. 477-507.
Lee et al., "Enhanced chondrogenesis of mesenchymal stem cells in collagen mimetic peptide mediated microenvironment," Tissue Engineering (2008) Part A 14(11):1843-1851.
Li et al., "Targeting and mimicking collagens via triple helical peptide assembly," Curr. Opin. Chem. Biol. (2013) 17:968-975.
Lodish, et al., "Collagen: The Fibrous Proteins of the Matrix", In: Molecular Cell Biology, 4th edition New York: W. H. Freeman, 2000, Section 22.3.
Luo et al., "Collagen-like peptides and peptide-polymer conjugates in the design of assembled materials," Eur Polym J (2013) 49(10):2998-3009.
Lutolf et al., "Synthetic biomaterials as instructive extracellular microenvironments for morphogenesis in tissue engineering," Nat Biotechnol (2005) 23(1):47-55.
Lynn et al., "Antigenicity and immunogenicity of Collagen," Journal of Applied Biomedical Materials Research (2004) 71B:343-354.
Ma et al., "Crosslinking strategies for preparation of extracellular matrix-derived cardiovascular scaffolds," Regenerative Biomaterials (2014) 1(1):81-89.
Mattson et al., "A pratical approach to crosslinking," Molecular Biology Reports (1993) 17(3):167-183.
Niyibizi et al., "Bone Type V Collagen: Chain Composition and Location of a Trypsin Cleavage Site," Connective Tissue Research (1989) 20(1-4):247-250.
O'Reilly et al., "Endostatin: An Endogenous Inhibitor of Angiogenesis and Tumor Growth," Cell (1997) 88(2):277-285.
Ortega et al., "New functional roles for non-collagenous domains of basement membrane collagens," Journal Cell Science (2002)115:4201-4214.
Przbyla et al., "Higher-Order Assembly of Collagen Peptides into Nano- and Microscale Materials," J. Biochemistry (2010) 49:4411-4419.
Chopra et al., "Conformational implications of enzymatic proline hydroxylation in collagen," Proceedings of the National Academy of Science of the United States of America (1982) 79(23):7180-7184.
Rush et al., "Administration of Menadione, Vitamin K3, Ameliorates Off-Target Effects on Corneal Epithelial Wound Healing Due to Receptor Tyrosine Kinase Inhibition," Investigative Ophthalmology & Visual Science (2016) 57(14):5864-5871.
Rush et al., "Antagonizing c-Cbl Enhances EGFR-Dependent Corneal Epithelial Homeostasis," Investigative Ophthalmology & Visual Science (2014) 55(8):4691-4699.
Sakakibara, et al., "Synthesis of (Pro-Hyp-Gly)n of defined molecular weights Evidence for the stabilization of collagen triple helix by hydroxypyroline," Biochimica et Biophysica Acta (1973) 303(1):198-202.
Schlegel et al., "De novo bone formation using bovine collagen and platelet-rich plasma," Biomaterials (2004) 25(23):5387-5393.
Schuppan et al., "Collagens in the Liver Extracellular Matrix Bind Hepatocyte Growth Factor," Gastroenterology (1998) 114(1):139-152.
Shoulders et al., "Collagen structure and stability," Annual Review Biochememistry (2009) 78:929-958.
Siebler et al., "From Azidoproline to Functionalizable Collagen," Chimia (2013) 67:891-895.
Staros et al., "Enchancement by N-hydroxysulfosuccinimide of water-soluble carbodiimide-mediated coupling reactions," Analytical Biochemistry (1986) 156:220-222.
Strauss et al., "Advances in the design and higher-order assembly of collagen mimetic peptides for regenerative medicine," Current Opinion in Biotechnology (2017) 46:34-41.
Tanrikulu et al., "Peptide tessellation yields micron-scale collagen triple helices," Nat. Chem. (2016) 8(12):1008-1014.
Miyata et al., "Collagen Engineering for Biomaterial Use," Clinical Materials (1992) 9:139-148.
Timkovich, Russell, "Detection of the stable addition of carbodiimide to proteins," Analytical Biochemistry (1977) 79:135-43.
Wakitani, et al., "Repair of rabbit articular surfaces with allograft chondrocytes embedded in collagen gel," The Journal of Bone Joint Surgery (1989) 71-B:74-80.
Wang et al., "Facile Modification of Collagen Directed by Collagen Mimetic Peptides," J. Am. Chem. Soc. (2004):1.9.
Wollensak et al. "Riboflavin/ultraviolet-A-induced collagen crosslinking for the treatment of keratoconus"; American Journal of Ophthalmology, Ophthalmic (2003) 135(5):620-627.
Yamaguchi et al., "Negative regulation of transforming growth factor-B by the proteoglycan decorin," Nature (1990) 346:281-284.
Yu et al., "Collagen mimetic peptides: progress towards functional applications," Soft Matter (2011) 7:7927-7938.
Zhu et al., "Type IIA Procollagen Containing the Cyteine-rich Amino Propeptide Is Deposited in the Extracellular Matrix of Prechondrogenic Tissue and Binds to TGF-$\beta$1 and BMP-2," Journal of Cell Biology (1999) 144(5):1069-1080.
Karlen et al., "Deep sclerectomy with collagen implant: medium term results," Br. J. Ophthalmol. 83:6-11 (1999) (Year: 1999).
Dada et al., "Trabeculectomy With Combined Use of Subconjunctival Collagen Implant and Low-dose Mitomycin C," J. Glaucoma 22:659-662 (2013) (Year: 2013).
Wipperman et al., "Evaluation and Management of Corneal Abrasions," American Family Physician 87: 114-120 (2013) (Year: 2013).
Abelson et al., "Glaucoma and Dry Eye: A Tough Combo," Rev. Ophthalmology (Oct. 2011), accessed Nov. 1, 2019 at URL: reviewofophthalmology.com/article/glaucoma-and-dry-eye-a-tough-combo, pp. 1-7 (Year: 2011).
Cameron et al., "Type IV Collagen and Corneal Epithelial Adhesion and Migration," Investigative Opthalmology & Visual Science 32:2766-2773 (1991).
Torricelli et al., "The Corneal Epithelial Basement Membrane: Structure, Function, and Disease," Investigative Ophthalmology & Visual Science 54:6390-6400 (2013).

\* cited by examiner

COLLAGEN PEPTIDE-BASED MEDICAMENT COMPOSITIONS AND DEVICES AND METHODS OF PRODUCTION AND USE THEREOF

CROSS-REFERENCE TO RELATED APPLICATIONS AND INCORPORATION BY REFERENCE

The present application is related to and claims the benefit of the filing dates of U.S. Provisional Application No. 62/836,934, filed on Apr. 22, 2019, 62/933,685, filed Nov. 11, 2019, and 62/959,282, filed Jan. 10, 2020, all entitled "Collagen-Based Medicament Compositions and Devices and Methods of Production and Use Thereof" and naming as inventors Richard E. Schlumpf, Robert Baratta, Shawn A. DeLorey and David J. Calkins. The contents of these applications are incorporated herein by reference in their entireties.

STATEMENT REGARDING FEDERALLY SPONSORED RESEARCH AND DEVELOPMENT

Not applicable.

NAMES OF THE PARTIES TO A JOINT RESEARCH AGREEMENT

Not applicable.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Jul. 16, 2020, is named 0123-0009US1_SL.txt and is 338,738 bytes in size.

BACKGROUND OF THE INVENTION

Field of the Invention

The present invention is in the fields of medicinal chemistry, biotechnology, pharmaceuticals and medical devices, as well as the use of medicinal compounds and medical devices for the treatment, prevention and amelioration of diseases, disorders and physical ailments in humans and veterinary animals.

Background Art

Collagen is the most abundant protein in vertebrates, and is the fundamental structural protein for vertebrate tissues, occurring in virtually every tissue including skin and other epithelial tissues (including the lining of most luminal organs such as those of the gastrointestinal tract), tendons, bone, blood vessels, cartilage, ligaments and teeth. In humans, collagen makes up about a third of the total protein and about three-quarters of the dry weight of skin (see Shoulders, M. D., and Raines, R. T., Ann. Rev. Biochem. 78:929-958 (2009); Gelse, K., et al., Adv. Drug Deliv. Rev. 55:1531-1546 (2003)).

Collagen is a fibrous protein that is composed of a triple helix, which generally consists of two identical chains and a third chain that differs slightly in its chemical composition. Mammals produce at least 46 distinct collagen polypeptide chains that combine to form variants or "types" of collagen. To date, 28 types of collagen have been described. Collagen types are generally grouped according to their structural forms: fibrillar (types I, II, III, V and XI) which represent about 90% of all collagen protein found in mammals, and non-fibrillar (basement membrane or type IV, and other non-fibrillar collagen types with interrupted helix structures) see Id.). The five most common types of collagen, and their tissue distributions, are:

Type I: skin, tendon, organs, bone, vascular connective tissue;

Type II: cartilage;

Type III: reticular connective tissue, often associated with Type I collagen;

Type IV: basement membranes of epithelial tissues and certain solid tumors; and

Type V: hair, placenta, external cellular membranes.

In each of these variants, the polypeptide chains of collagen are composed of approximately 300 repeats of the amino acids proline (Pro), 4(R)-hydroxyproline (Hyp) and glycine (Gly), usually in the sequence X-Y-Gly, where X is often a Pro residue and Y is often a (Hyp) residue; in vertebrates, the typical repeat motif in collagen is ProProGly (see Hulmes, D. J. S., "Collagen Diversity, Synthesis and Assembly," in: Collagen: Structure and Mechanics, P. Fratzl, Ed., New York: Springer, pp. 15-47 (2008)). Subsequently, in vivo, the hydroxylation of Pro residues is performed enzymatically after collagen biosynthesis but before the chains begin to form a triple helix. Thus, hydroxylation of at least one Pro residue in the ProProGly motif, typically forming ProHypGly, appears to be important for both the proper folding and stability of the collagen triple helix, both of which are key to the normal structure and function of collagen in vivo (see Shoulders, M. D., and Raines, R. T., Ann. Rev. Biochem. 78:929-958 (2009)). For example, the melting temperature of a triple helix of (ProHypGly)$_{10}$ (SEQ ID NO: 396) chains is 58° C., while that of a triple helix of (ProProGly)$_{10}$ (SEQ ID NO: 397) chains is only 24° C. (Sakakibara et al., Biochim. Biophys. Acta, 303:198-202 (1973)), and the rate at which (ProHypGly)$_{10}$ (SEQ ID NO: 396) chains fold into a triple helix is substantially greater than the corresponding rate for (ProProGly)$_{10}$ SEQ ID NO: 397) chains (Chopra and Ananthanarayanan, Proc. Natl. Acad. Sci. USA, 79:7180-7184 (1982)).

Type I collagen is the most abundant and best-studied collagen. In humans and most other animals it forms more than 90% of the organic mass of bone and is the major collagen of tendons, skin, ligaments, cornea, and many interstitial connective tissues with the exception of a very few such as hyaline cartilage, brain and the vitreous body. The collagen type I triple helix is usually formed as a heterotrimer by two identical α1 chains and one α2 chain. The triple helical fibers are, in vivo, primarily incorporated into composite fibrils containing other types of collagens, which as noted above vary depending upon tissue type and location (Fleischmajer, E. D. et al., J. Struct. Biol. 105: 162-169 (1990); Niyibizi, C. and Eyre, D. R., Connect. Tissue Res. 20: 247-250 (1989)). In most organs and notably in tendons and fascia, type I collagen provides tensile rigidity and in bone, it defines the biomechanical properties relating to load bearing, tensile strength and torsional stiffness.

In connective tissues (such as bone, tendon, cartilage, ligament, skin, blood vessels and teeth), individual collagen molecules are wound together in tight triple helices. These helices are organized into fibrils of great tensile strength (Jones & Miller, J. Mol. Biol., 218:209-219 (1991)) via cross-linking of individual triple helix fibers (Lodish, H. et al., "Collagen: The Fibrous Proteins of the Matrix", in: Molecular Cell Biology, 4th ed., Section 22.3, New York: W. H. Freeman (2000)). Varying the arrangements and cross linking of the collagen fibrils enables vertebrates to support stress in one dimension (tendons), two dimensions (skin) or three dimensions (cartilage).

Collagens serve within the body to a considerable extent for the maintenance of the structural integrity of tissues and organs. In all parenchymal organs, collagens represent the major component of the interstitial matrix as well as the basement membranes, while in all connective tissues, particularly bone and cartilage, collagens provide the major functional backbone of the structures. Besides the biomechanical aspects, however, collagens are also involved in a variety of additional functions. For example, specific cell surface and intracellular receptors interact with collagens, and signaling by these receptors is involved in cellular adhesion, differentiation, growth and other cellular activities, as well as the survival of cells both in vivo and in vitro (Vogel, W. F., Eur. J. Dermatol. 11: 506-514 (2001); Gelse, K., et al., Adv. Drug Deliv. Rev. 55:1531-1546 (2003)). Collagens also are involved in the entrapment, local storage and delivery of growth factors and cytokines in a variety of tissues in which the collagens are found. Through these receptor interactions and storage and delivery functions, collagen plays a key role in organ development, wound healing and tissue repair (Chattopadhyay, S. and R. Raines, Biopolymers 101: 821-833 (2014); Yamaguchi, Y. et al., Nature 346: 281-284 (1990); Hay, E. D., J. Cell Biol. 91:205s-223s (1981); Bautista, C. M. et al., Metabolism 39: 96-100 (1990); Zhu, Y. et al., J. Cell Biol. 144: 1069-1080 (1998); Schlegel, K. A. et al., Biomaterials 25:5387-5393 (2004); Kumar, V. A., et al., Biomacromol. 15: 1484-1490 (2014)). These functions also qualify collagens as candidate transport vehicles for the delivery of therapeutic compounds (see, e.g., Chattopadhyay, S. et al., J. Tissue Eng. Regen. Med. 10:1012-1020 (2012); Schuppan, D. et al., Gastroenterol. 114: 139-152 (1998); Frenkel, S. R. et al., J. Bone Jt. Surg. 79-B: 831-836 (1997); Albu, M. G. et al., "Collagen-Based Drug Delivery Systems for Tissue Engineering", in: Biomaterials Applications for Nanomedicine, Pignatello, R. (Ed.), ISBN: 978-953-307-661-4, DOI: 10.5772/22981, Rijeka, Croatia: InTech, available from: https://www.intechopen.com/books/biomaterials-applications-for-nanomedicine/collagen-based-drug-delivery-systems-for-tissue-engineering (2011)), and for use in wound healing by directly promoting tissue repair or regeneration (Wakitani, S. et al., J. Bone Jt. Surg. 71-B: 74-80 (1989); Kumar, V. A., et al., Biomacromol. 15: 1484-1490 (2014)). Collagen (more particularly, disrupted collagen) has also been implicated in tumor progression and metastasis in humans and other vertebrates (for a review of this issue, see Fang, M., et al., Tumor Biol. 35:2871-2882 (2014)).

Beyond intact collagen molecules, however, fragments of collagen may also have potential therapeutic uses, and indeed, may perform in a superior fashion relative to native collagen. For example, non-collagenous fragments of collagens IV, XV and XVIII have been shown to promote the growth of blood vessels and tumor cells, and to influence a variety of other cellular activities (Ortega, N. and Werb, Z., J. Cell Sci. 115: 4201-4214 (2002); Davis, G. E. et al., Am. J. Pathol. 156: 1489-1498 (2000); O'Reilly, M. S. et al., Cell 88: 277-285 (1997)). Analogously, as described in greater detail below, fragments or synthetic collagen mimetic peptides (CMPs) of collagen type I have recently been studied for their utility in treatment of diseases and medical disorders, both as active pharmaceutical ingredients (APIs) in their own right and in the delivery of a skin wound-healing agent (see U.S. Pat. Nos. 5,973,112, 7,122,521, 7,858,741, and U.S. Patent Publ. No. US 2007/0275897 A1, the disclosures of all of which are incorporated herein by reference in their entireties; see also e.g., Chattopadhyay, S. et al., J. Tissue Eng. Regen. Med. 10:1012-1020 (2012); Kumar, V. A. et al., Biomacromolecules 15:1484-1490 (2014)).

Collagen abnormalities are associated with a wide variety of human diseases, including diseases and disorders of the eye such as cataracts and glaucoma (Coudrillier, B., et al., PLoS ONE 10: e0131396 (2015); Huang, W. et al., Med. Sci. Monit. Basic Res. 19: 237-240 (2013); Dua, H. S., et al., Br. J. Ophthalmol. 98: 691-697 (2014)), arthritis, rheumatism, brittle bones, atherosclerosis and cirrhosis. Disruptions in collagen are also associated with certain human and veterinary diseases such as certain cancers (particularly carcinomas of the luminal organs, and certain sarcomas); see, e.g., Lauer, J. L., and Fields, G. B., "Collagen in Cancer", in The Tumor Microenvironment, New York: Springer, pp. 477-507 (2010). Collagen is also critically important in wound healing and is known to be upregulated in areas of epithelial wounds where healing is taking place (see, e.g., U.S. Pat. Nos. 5,973,112 and 7,122,521, which are incorporated herein by reference in their entireties; see also Chattopadhyay, S., et al., J. Tissue Eng. Regen. Med. 10:1012-1020 (2012); Chattopadhyay, S., et al., Org. Biomol. Chem. 10:5892-5897 (2012); Kumar, V. A., et al., Biomacromol. 15: 1484-1490 (2014)), including in the skin and the cornea of the eye. Indeed, collagen, collagen fragments or certain mimetic peptides of natural collagen have been reported to show promise in treating certain wounds and diseases in humans and animals, particularly skin wounds (see, e.g., U.S. Pat. Nos. 5,973,112, 7,122,521, 7,858,741, and U.S. Patent Publ. No. US 2007/0275897 A1, all of which are incorporated herein by reference in their entireties; see also Kumar, V. A. et al., Biomacromolecules 15:1484-1490 (2014)). It is thought that these collagen fragments or collagen mimetic peptides may specifically target areas of collagen disruption associated with skin wounds by intercalating into the disrupted collagen and reforming the native collagen I triple helix (see, e.g., Chattopadhyay, S., et al., J. Tissue Eng. Regen. Med. 10:1012-1020 (2012); Chattopadhyay, S., et al., Org. Biomol. Chem. 10:5892-5897 (2012)). As a result, there have been attempts made to use collagen as a vehicle for delivering certain drugs, with varying degrees of success (see, e.g., B. An, et al., Adv. Drug Deliv. Rev. 97:69-84 (2016); V. Chak, et al., Intl. J. Pharm. Teaching and Practices 4:811 (2013)). Collagen mimetic peptides have also been used in a topical application to deliver a conjugated therapeutic compound, the neuropeptide known as Substance P, to areas of skin wounds; such CMP-Substance P conjugates have been shown to accelerate wound healing in a mouse skin model (Chattopadhyay, S., et al., J. Tissue Eng. Regen. Med. 10:1012-1020 (2012)). Certain extracellular matrix (ECM) components, including collagens, are also involved in maintaining proper structure and function of the nervous system, particularly the peripheral nervous system, and disruption of or damage to these ECM components often leads to nerve cell disorder and/or death (see, e.g., Koopmans G, Hasse B, Sinis N. The role of collagen in peripheral nerve repair (Chapter 19). International Review of Neurobiology. Volume 87: Academic Press, Elsevier; pp. 363-79 (2009); Gao X, et al., Rev. Neurosci. 24(4):443-53 (2013); Campbell I C et al., J. Biomech. Eng. 136(2):021005 (2014); Vecino E et al., J.

Cytol. Histol. 53:007 (2015); Vecino E., and Kwok, J. C. F., "The Extracellular Matrix in the Nervous System: The Good and the Bad Aspects", in Composition and Function of the Extracellular Matrix in the Human Body, F. Travascio, ed., Intech Open, ISBN 978-953-51-2416-0 (2016), accessed Nov. 8, 2019, at http://dx.doi.org/10.5772/62527).

Treatments for diseases/disorders are expensive, difficult to deliver with specificity, and may have deleterious effects at sites distal to the intended site of action. For example, many medicinal compositions, including antibiotics, small molecule therapeutics (e.g., anti-cancer compounds) and biologics (e.g., monoclonal antibody therapeutics) are administered parenterally in a non-targeted fashion and must diffuse or otherwise find their way to the site of the affliction before they are able to provide their therapeutic benefits. This "shotgun approach" to therapy necessarily requires higher dosing and can result in longer periods of therapy and reduced patient compliance than a therapeutic approach which would deliver therapeutic compounds and compositions in a more targeted fashion which would allow for controlled or programmable release at or near the site of the affliction in a human or veterinary animal.

Thus, there is a need in the art for drug delivery systems—i.e., compositions and methods of use—that will overcome many of these shortcomings in traditional treatments for certain diseases and disorders in humans and veterinary animals. Such advanced drug delivery systems would allow the use of lower doses of medication and more targeted delivery of the medications to the intended sites of action, as well as reducing the therapeutic problems or delays resulting from patient non-compliance. There also is a need for medical devices coated with such compositions which will facilitate more rapid healing and recovery in humans and animals suffering from such diseases and disorders. Finally, there is a need in the art for methods of producing such compositions and medical devices that will meet the needs of the medical and patient communities in maximizing treatment efficacies while reducing costs.

BRIEF SUMMARY OF THE INVENTION

The present inventors reasoned that since collagen disruption is associated with a variety of diseases and disorders in humans and other animals, the conjugation of a variety of therapeutic compounds and/or diagnostic compounds to collagen or collagen mimetic peptides would provide an elegant, rapid and reproducible way of overcoming many of the above-referenced limitations in drug delivery. Thus, the present invention provides such drug delivery systems, medical devices and methods of manufacturing the same. Accordingly, the present invention meets the needs in the art as expressed hereinabove.

In one aspect, the invention provides compositions comprising one or more collagen mimetic peptides (CMPs), which in certain embodiments have been conjugated one or more therapeutic compounds and/or one or more diagnostic compounds thereby forming CMP conjugates and compositions. Such CMPs and CMP conjugates, and compositions comprising such CMPs and/or CMP conjugates, are useful in treating, preventing, ameliorating and diagnosing a variety of diseases, disorders and physical conditions in humans and veterinary animals. In certain embodiments of this aspect, the invention provides compositions comprising such CMPs and/or CMP conjugates and one or more pharmaceutically acceptable carriers, excipients or compounding agents, and optionally one or more additional therapeutic or diagnostic agents, to provide therapeutic and diagnostic compositions useful in treating, preventing, ameliorating or diagnosing certain diseases and disorders in humans and veterinary animals.

In another aspect, the invention provides methods of treating, preventing, ameliorating or diagnosing certain diseases and disorders in humans and veterinary animals, by administering the conjugates and/or compositions of the invention to a human or veterinary animal suffering from or predisposed to such diseases or disorders. Diseases and disorders suitably treated, prevented, cured, ameliorated or diagnoses according to this aspect of the invention include ocular diseases or disorders, skin diseases or disorders, cancers, gastrointestinal diseases or disorders, genitourinary tract diseases or disorders, fibrotic diseases or disorders, cardiovascular diseases or disorders, bone diseases or disorders, and rheumatic diseases or disorders.

In yet another aspect, the invention provides medical devices coated with or comprising one or more of the conjugates or compositions of the invention. In related aspects, the invention provides methods of treating, curing, preventing or ameliorating diseases or disorders in humans or veterinary animals comprising implanting one or more of the medical devices of this aspect of the invention into the human or veterinary animal, under conditions such that the disease or disorder is treated, cured, prevented or ameliorated.

In still other aspects, the invention provides methods of manufacturing the compositions, conjugates and medical devices of the invention.

Other objects, advantages, and features of the present invention will be readily apparent to those of ordinary skill in the art upon review of the description, drawings, examples and claims presented herein.

BRIEF DESCRIPTION OF THE DRAWINGS

FIG. 1a, 1e), with 100 ng/mL of epidermal growth factor (EGF; FIG. 1b, if), or with 25 nM (about 3 mg/kg) of a (Pro-Pro-Gly)$_7$ CMP of the invention (SEQ ID NO:1) ("Compound 3"; FIG. 1c, 1g), or of a (Hyp-Pro-Gly)$_7$-SubP CMP-TC of the invention (SEQ ID NO:391) ("Compound 10"; FIG. 1d, 1h). The extent of the remaining corneal abrasion and damage to the underlying corneal stroma was then revealed with fluorescein staining and fluorescence photomicrography of the eyes at time 0 (FIGS. 1a-1d) and 16 hours (FIGS. 1e-1h) post-wounding. FIGS. 1i and 1j are photomicrographs of H&E-stained thin sections of corneal epithelial and subepithelial tissue 24 hours post-wounding and treated with PBS (FIG. 1i) or Compound 3 (FIG. 1j).

FIG. 2a: PBS-treated section; FIG. 2b: Compound 3-treated section. Arrows depict the lack of (FIG. 2a) or presence of (FIG. 2b) basement membrane.

FIG. 4a) or with Compound 3 (FIG. 4b) prior to plating cells.

FIG. 5a: vehicle-treated plates; FIG. 5b: plates treated with Compound 3.

FIG. 7a) or Compound 3 (FIG. 7b).

FIG. 8a), native type I collagen (FIG. 8b) or Compound 3 (FIG. 8c), onto the apical side of which RPE cells were plated and permitted to migrate for 24 hours.

FIG. 11A: stained reducing SDS-PAGE of human type I atelocollagen untreated ("Collagen" lane) or treated with MMP-1 ("Cleaved Collagen" lane). $TC^A$: ¾ fragment of α1(I) collagen; $TC^B$: ¼ fragment of α2(I) collagen. Arrows indicate the α1(I) and α2(I) bands quantitated in FIG. 11B. FIG. 11B: bar graph showing quantitation of full-length α1(I) and α2(I) bands in untreated collagen vs. MMP-1-cleaved collagen.

FIG. 12A) or with MMP-1-digested type I collagen ("Cut Collagen"; FIGS. 12B-D). Following coating, plates were treated with vehicle (PBS; FIGS. 12A and 12B) or with CMP A (SEQ ID NO:3) (FIG. 12C) or CMP B (SEQ ID NO:6) (FIG. 12D) prior to plating cells. Cells were incubated for 19 hours at 37° C. for 19 hours prior to photomicrography.

FIG. 13A: all samples shown; FIG. 13B: re-scaling of the data shown in FIG. 13A, with the "Collagen" data excluded for clarity. Error bars are mean±SEM, n=3.

FIG. 14A) or with MMP-1-digested type I collagen ("Cut Collagen"; FIGS. 14B-F). Following coating, plates were treated with vehicle (PBS; FIGS. 14A and 14B) or with CMP A (SEQ ID NO:3) (FIG. 14C), CMP B (SEQ ID NO:6) (FIG. 14D), CMP C (SEQ ID NO:391) (FIG. 14E) or CMP D (SEQ ID NO:13) (FIG. 14F) prior to plating cells. Cells were incubated for 48 hours at 37° C. for 19 hours prior to photomicrography.

FIG. 15A) and length of longest neurite (FIG. 15B) in DRG neurons observed under the various conditions described and depicted in FIG. 14, including treatment with CMPs A (SEQ ID NO:3), B (SEQ ID NO:6), C (SEQ ID NO:391) or D (SEQ ID NO:13). All data were normalized to the adherence observed in "Cut Collagen" replicates. FIG. 15A: *=$p \leq 0.03$ vs. Cut Collagen; FIG. 15B: *=$p \leq 0.02$ vs. Cut Collagen. Error bars are mean SEM, n=3.

FIGS. 16A and 16C show localization of TF2-CMP extranuclearly in the ganglion cell layer of the retina (arrows: retinal blood vessels; arrowheads: nuclei of ganglion cells), while FIGS. 16B and 16D show localization of TF2-CMP in or near the inner limiting membrane (vitreous surface) of the retina.

DETAILED DESCRIPTION OF THE INVENTION

Figure 1:
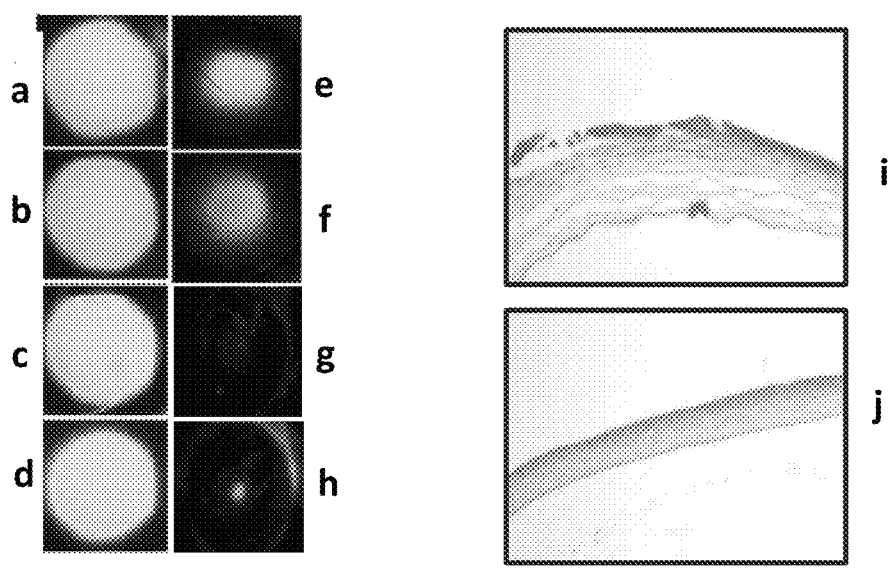
FIG. 1 is a series of photomicrographs depicting the healing of a wound in the cornea of mouse eye, at time 0 and 16 hours post-wounding, upon treatment with certain compositions of the present invention. Wounds were introduced into the corneas of mice, and the mice treated immediately after wounding with vehicle (PBS.

Unless defined otherwise, all technical and scientific terms used herein have the same meanings as commonly understood by one of ordinary skill in the arts to which this invention belongs. Although any methods and materials similar or equivalent to those described herein can be used in the practice or testing of the present invention, the preferred methods and materials are described hereinafter.

According to a first aspect, the invention provides compositions suitable for use in a medicament for treating or preventing a disease, disorder, structural abnormality or injury in a human or veterinary animal in need of treatment or prevention of such as a disease, disorder, structural abnormality or injury. In certain embodiments, the compositions provided by the invention comprise (a) at least one collagen mimetic peptide (CMP) attached to at least one additional therapeutic compound (TC) to form a CMP-TC conjugate, and (b) one or more pharmaceutically suitable carriers. In related aspects, the invention provides compositions suitable for use in a diagnostic agent suitable for diagnosing or detecting a disease, disorder, structural abnormality or injury in a human or veterinary animal in need thereof. In certain embodiments, the compositions provided by the invention comprise (a) at least one collagen mimetic peptide (CMP) attached to at least one diagnostic compound or agent (DC) to form a CMP-DC conjugate, and (b) one or more pharmaceutically suitable carriers. In other related embodiments, the compositions provided by the invention comprise (a) at least one collagen mimetic peptide (CMP) and (b) at least one additional therapeutic compound, wherein the CMP and the at least one additional therapeutic compound are admixed in a formulation, or "co-formulated," optionally together with one or more pharmaceutically suitable carriers. In analogous embodiments, the compositions provided by the invention comprise (a) at least one collagen mimetic peptide (CMP) and (b) at least one diagnostic compound or agent, such as a labeling compound or agent, wherein the CMP and the at least one diagnostic compound or agent are admixed in a formulation, or "co-formulated," optionally together with one or more pharmaceutically suitable carriers, for use in one or more diagnostic methods of the invention.

In certain embodiments of the invention, the collagen mimetic peptide comprises, consists essentially of or consists of an amino acid sequence that is a multimeric repeat of a specific tripeptide having a sequence (Xaa-Yaa-Gly)$_n$ (SEQ ID NO: 398), wherein Xaa is independently selected from the group consisting of proline, 4S-hydroxyproline, fluoroproline, chloroproline, lysine, cysteine and methionine; wherein Yaa is independently selected from the group consisting of proline, 4R-hydroxyproline, fluoroproline, chloroproline, lysine, cysteine and methionine; wherein Gly is a glycine residue; and wherein n is an integer ranging from 1 to 20, such as from 3 to 15, from 5 to 15, or from 5 to 10, and is preferably 5, 6, 7, 8, 9 or 10.

In certain embodiments of the invention, the collagen mimetic peptide comprises, consists essentially of or consists of an amino acid sequence that is or corresponds to a 21-mer comprising seven repeats of a three amino acid sequence of proline-proline-glycine ((Pro-Pro-Gly)$_7$), i.e., an amino acid sequence of: Pro-Pro-Gly-Pro-Pro-Gly-Pro-Pro-Gly-Pro-Pro-Gly-Pro-Pro-Gly-Pro-Pro-Gly-Pro-Pro-Gly (SEQ ID NO:1).

In certain other embodiments of the invention, the collagen mimetic peptide comprises, consists essentially of or consists of an amino acid sequence that is or corresponds to a 21-mer comprising seven repeats of a three amino acid sequence in which hydroxyproline (Hyp), and preferably a 4S-hydroxyproline residue, has been substituted for proline$_1$ in SEQ ID NO:1, yielding a sequence of seven repeats of 4S-hydroxyproline-proline-glycine ((Hyp-Pro-Gly)$_7$), i.e., an amino acid sequence of: Hyp-Pro-Gly-Hyp-Pro-Gly-Hyp-Pro-Gly-Hyp-Pro-Gly-Hyp-Pro-Gly-Hyp-Pro-Gly-Hyp-Pro-Gly (SEQ ID NO:2).

In certain other embodiments of the invention, the collagen mimetic peptide comprises, consists essentially of or consists of an amino acid sequence that is or corresponds to a 21-mer comprising seven repeats of a three amino acid sequence in which Hyp, and preferably a 4S-hydroxyproline residue, has been substituted for proline$_2$ in SEQ ID NO:1, yielding a sequence of seven repeats of 4S-hydroxyproline-proline-glycine ((Pro-Hyp-Gly)$_7$), i.e., an amino acid sequence of: Pro-Hyp-Gly-Pro-Hyp-Gly-Pro-Hyp-Gly-Pro-Hyp-Gly-Pro-Hyp-Gly-Pro-Hyp-Gly-Pro-Hyp-Gly (SEQ ID NO:3).

In certain other embodiments of the invention, the collagen mimetic peptide comprises, consists essentially of or consists of an amino acid sequence that is or corresponds to a 21-mer comprising seven repeats of a three amino acid sequence in which fluoroproline (Flp) has been substituted for proline$_1$ in SEQ ID NO:1, yielding a sequence of seven repeats of fluoroproline-proline-glycine ((Flp-Pro-Gly)$_7$), i.e., an amino acid sequence of: Flp-Pro-Gly-Flp-Pro-Gly-Flp-Pro-Gly-Flp-Pro-Gly-Flp-Pro-Gly-Flp-Pro-Gly-Flp-Pro-Gly (SEQ ID NO:4).

In certain other embodiments of the invention, the collagen mimetic peptide comprises, consists essentially of or consists of an amino acid sequence that is or corresponds to a 21-mer comprising seven repeats of a three amino acid sequence in which Flp has been substituted for proline$_2$ in SEQ ID NO:1, yielding a sequence of seven repeats of proline-fluoroproline-glycine ((Pro-Flp-Gly)$_7$), i.e., an amino acid sequence of: Pro-Flp-Gly-Pro-Flp-Gly-Pro-Flp-Gly-Pro-Flp-Gly-Pro-Flp-Gly-Pro-Flp-Gly-Pro-Flp-Gly (SEQ ID NO:5).

In certain other embodiments of the invention, the collagen mimetic peptide comprises, consists essentially of or consists of an amino acid sequence that is or corresponds to a 21-mer comprising seven repeats of a three amino acid sequence in which fluoroproline (Flp) has been substituted for proline$_1$ in SEQ ID NO:1 and Hyp has been substituted for proline$_2$ in SEQ ID NO:1, yielding a sequence of seven repeats of fluoroproline-hydroxyproline-glycine ((Flp-Hyp-Gly)$_7$), i.e., an amino acid sequence of: Flp-Hyp-Gly-Flp-Hyp-Gly-Flp-Hyp-Gly-Flp-Hyp-Gly-Flp-Hyp-Gly-Flp-Hyp-Gly-Flp-Hyp-Gly (SEQ ID NO:6).

In CMPs containing Flp, the Flp moiety may be in the 4-cis or 4-trans configuration, and preferably is in the 4-cis configuration.

In certain other embodiments of the invention, the collagen mimetic peptide may comprise, consist of or have an amino acid sequence that is or corresponds to a 21-mer comprising seven repeats of a three amino acid sequence in which chloroproline (Clp) has been substituted for proline$_1$ in SEQ ID NO:1, yielding a sequence of seven repeats of chloroproline-proline-glycine ((Clp-Pro-Gly)$_7$), i.e., an amino acid sequence of: Clp-Pro-Gly-Clp-Pro-Gly-Clp-Pro-Gly-Clp-Pro-Gly-Clp-Pro-Gly-Clp-Pro-Gly-Clp-Pro-Gly (SEQ ID NO:7).

In certain other embodiments of the invention, the collagen mimetic peptide may comprise, consist of or have an amino acid sequence that is or corresponds to a 21-mer comprising seven repeats of a three amino acid sequence in which chloroproline (Clp) has been substituted for proline$_2$ in SEQ ID NO:1, yielding a sequence of seven repeats of proline-chloroproline-glycine ((Pro-Clp-Gly)$_7$), i.e., an amino acid sequence of: Pro-Clp-Gly-Pro-Clp-Gly-Pro-Clp-Gly-Pro-Clp-Gly-Pro-Clp-Gly-Pro-Clp-Gly-Pro-Clp-Gly (SEQ ID NO:8).

In certain other embodiments of the invention, the collagen mimetic peptide comprises, consists essentially of or consists of an amino acid sequence that is or corresponds to a 21-mer comprising seven repeats of a three amino acid sequence in which Clp has been substituted for proline$_1$ in SEQ ID NO:1 and Hyp has been substituted for proline$_2$ in SEQ ID NO:1, yielding a sequence of seven repeats of chloroproline-hydroxyproline-glycine ((Clp-Hyp-Gly)$_7$), i.e., an amino acid sequence of: Clp-Hyp-Gly-Clp-Hyp-Gly-Clp-Hyp-Gly-Clp-Hyp-Gly-Clp-Hyp-Gly-Clp-Hyp-Gly-Clp-Hyp-Gly (SEQ ID NO:9).

In CMPs containing Clp, the Clp moiety may be in the 4-cis or 4-trans configuration, and preferably is in the 4-cis configuration.

In certain other embodiments of the invention, the collagen mimetic peptide may comprise, consist of or have an amino acid sequence that is or corresponds to a 21-mer of any one of SEQ ID NOs:1-9, in which at least one cysteine (Cys) residue has been substituted for at least one of the proline residues in SEQ ID NO:1, at least one of the hydroxyproline residues in SEQ ID NOs:2-3 and 6, at least one of the fluoroproline residues in SEQ ID NOs:4-6, or at least one of the chloroproline residues in SEQ ID NOs:7-9, yielding, for example, the following sequences:

```
                                                              (SEQ ID NO: 10)
Pro-Pro-Gly-Pro-Pro-Gly-Cys-Pro-Gly-Pro-Pro-Gly-Pro-Pro-Gly-Pro-
Pro-Gly;

(SEQ ID NO: 11)
Hyp-Pro-Gly-Hyp-Pro-Gly-Cys-Pro-Gly-Hyp-Pro-Gly-Hyp-Pro-Gly-Hyp-Pro-Gly-
Hyp-Pro-Gly;

(SEQ ID NO: 12)
Pro-Hyp-Gly-Pro-Hyp-Gly-Pro-Cys-Gly-Pro-Hyp-Gly-Pro-Hyp-Gly-
Pro-Hyp-Gly;

(SEQ ID NO: 13)
Pro-Flp-Gly-Pro-Flp-Gly-Pro-Cys-Gly-Pro-Flp-Gly-Pro-Flp-Gly-Pro-
Flp-Gly;

(SEQ ID NO: 14)
Pro-Clp-Gly-Pro-Clp-Gly-Pro-Cys-Gly-Pro-Clp-Gly-Pro-Clp-Gly-Pro-
Clp-Gly;

(SEQ ID NO: 15)
Cys-Pro-Gly-Pro-Pro-Gly-Pro-Pro-Gly-Pro-Pro-Gly-Pro-Pro-Gly-Pro-
Pro-Gly;

(SEQ ID NO: 16)
Pro-Cys-Gly-Pro-Pro-Gly-Pro-Pro-Gly-Pro-Pro-Gly-Pro-Pro-Gly-Pro-
Pro-Gly;

(SEQ ID NO: 17)
Pro-Pro-Gly-Cys-Pro-Gly-Pro-Pro-Gly-Pro-Pro-Gly-Pro-Pro-Gly-Pro-
Pro-Gly;

(SEQ ID NO: 18)
Pro-Pro-Gly-Pro-Cys-Gly-Pro-Pro-Gly-Pro-Pro-Gly-Pro-Pro-Gly-Pro-
Pro-Gly;

(SEQ ID NO: 19)
Pro-Pro-Gly-Pro-Pro-Gly-Pro-Cys-Gly-Pro-Pro-Gly-Pro-Pro-Gly-Pro-
Pro-Gly;

(SEQ ID NO: 20)
Pro-Pro-Gly-Pro-Pro-Gly-Pro-Pro-Gly-Cys-Pro-Gly-Pro-Pro-Gly-Pro-
Pro-Gly;

(SEQ ID NO: 21)
Pro-Pro-Gly-Pro-Pro-Gly-Pro-Pro-Gly-Pro-Cys-Gly-Pro-Pro-Gly-Pro-
Pro-Gly;

(SEQ ID NO: 22)
Pro-Pro-Gly-Pro-Pro-Gly-Pro-Pro-Gly-Pro-Pro-Gly-Cys-Pro-Gly-Pro-
Pro-Gly;

(SEQ ID NO: 23)
Pro-Pro-Gly-Pro-Pro-Gly-Pro-Pro-Gly-Pro-Pro-Gly-Pro-Cys-Gly-Pro-
Pro-Gly;

(SEQ ID NO: 24)
Pro-Pro-Gly-Pro-Pro-Gly-Pro-Pro-Gly-Pro-Pro-Gly-Pro-Pro-Gly-Cys-Gly-Pro-
Pro-Gly;

(SEQ ID NO: 25)
Pro-Pro-Gly-Pro-Pro-Gly-Pro-Pro-Gly-Pro-Pro-Gly-Pro-Pro-Gly-Pro-Cys-Gly-Cys-
Pro-Gly;
```

-continued (SEQ ID NO: 26)
Pro-Pro-Gly-Pro-Pro-Gly-Pro-Pro-Gly-Pro-Pro-Gly-Pro-Pro-Gly-Pro-Pro-Gly-Cys-Pro-Gly;

(SEQ ID NO: 27)
Pro-Pro-Gly-Pro-Pro-Gly-Pro-Pro-Gly-Pro-Pro-Gly-Pro-Pro-Gly-Pro-Pro-Gly-Pro-Cys-Gly;

(SEQ ID NO: 28)
Cys-Pro-Gly-Hyp-Pro-Gly-Hyp-Pro-Gly-Hyp-Pro-Gly-Hyp-Pro-Gly-Hyp-Pro-Gly-Hyp-Pro-Gly;

(SEQ ID NO: 29)
Hyp-Cys-Gly-Hyp-Pro-Gly-Hyp-Pro-Gly-Hyp-Pro-Gly-Hyp-Pro-Gly-Hyp-Pro-Gly-Hyp-Pro-Gly;

(SEQ ID NO: 30)
Hyp-Pro-Gly-Cys-Pro-Gly-Hyp-Pro-Gly-Hyp-Pro-Gly-Hyp-Pro-Gly-Hyp-Pro-Gly-Hyp-Pro-Gly;

(SEQ ID NO: 31)
Hyp-Pro-Gly-Hyp-Cys-Gly-Hyp-Pro-Gly-Hyp-Pro-Gly-Hyp-Pro-Gly-Hyp-Pro-Gly-Hyp-Pro-Gly;

(SEQ ID NO: 32)
Hyp-Pro-Gly-Hyp-Pro-Gly-Hyp-Cys-Gly-Hyp-Pro-Gly-Hyp-Pro-Gly-Hyp-Pro-Gly-Hyp-Pro-Gly;

(SEQ ID NO: 33)
Hyp-Pro-Gly-Hyp-Pro-Gly-Hyp-Pro-Gly-Cys-Pro-Gly-Hyp-Pro-Gly-Hyp-Pro-Gly-Hyp-Pro-Gly;

(SEQ ID NO: 34)
Hyp-Pro-Gly-Hyp-Pro-Gly-Hyp-Pro-Gly-Hyp-Cys-Gly-Hyp-Pro-Gly-Hyp-Pro-Gly-Hyp-Pro-Gly;

(SEQ ID NO: 35)
Hyp-Pro-Gly-Hyp-Pro-Gly-Hyp-Pro-Gly-Hyp-Pro-Gly-Cys-Pro-Gly-Hyp-Pro-Gly-Hyp-Pro-Gly;

(SEQ ID NO: 36)
Hyp-Pro-Gly-Hyp-Pro-Gly-Hyp-Pro-Gly-Hyp-Pro-Gly-Hyp-Cys-Gly-Hyp-Pro-Gly-Hyp-Pro-Gly;

(SEQ ID NO: 37)
Hyp-Pro-Gly-Hyp-Pro-Gly-Hyp-Pro-Gly-Hyp-Pro-Gly-Hyp-Pro-Gly-Cys-Pro-Gly-Hyp-Pro-Gly;

(SEQ ID NO: 38)
Hyp-Pro-Gly-Hyp-Pro-Gly-Hyp-Pro-Gly-Hyp-Pro-Gly-Hyp-Pro-Gly-Hyp-Cys-Gly-Hyp-Pro-Gly;

(SEQ ID NO: 39)
Hyp-Pro-Gly-Hyp-Pro-Gly-Hyp-Pro-Gly-Hyp-Pro-Gly-Hyp-Pro-Gly-Hyp-Pro-Gly-Cys-Pro-Gly;

(SEQ ID NO: 40)
Hyp-Pro-Gly-Hyp-Pro-Gly-Hyp-Pro-Gly-Hyp-Pro-Gly-Hyp-Pro-Gly-Hyp-Pro-Gly-Hyp-Cys-Gly;

(SEQ ID NO: 41)
Cys-Hyp-Gly-Pro-Hyp-Gly-Pro-Hyp-Gly-Pro-Hyp-Gly-Pro-Hyp-Gly-Pro-Hyp-Gly-Pro-Hyp-Gly;

-continued (SEQ ID NO: 42)
Pro-Cys-Gly-Pro-Hyp-Gly-Pro-Hyp-Gly-Pro-Hyp-Gly-Pro-Hyp-Gly-
Pro-Hyp-Gly;

(SEQ ID NO: 43)
Pro-Hyp-Gly-Cys-Hyp-Gly-Pro-Hyp-Gly-Pro-Hyp-Gly-Pro-Hyp-Gly-
Pro-Hyp-Gly;

(SEQ ID NO: 44)
Pro-Hyp-Gly-Pro-Cys-Gly-Pro-Hyp-Gly-Pro-Hyp-Gly-Pro-Hyp-Gly-
Pro-Hyp-Gly;

(SEQ ID NO: 45)
Pro-Hyp-Gly-Pro-Hyp-Gly-Cys-Hyp-Gly-Pro-Hyp-Gly-Pro-Hyp-Gly-
Pro-Hyp-Gly;

(SEQ ID NO: 46)
Pro-Hyp-Gly-Pro-Hyp-Gly-Pro-Hyp-Gly-Cys-Hyp-Gly-Pro-Hyp-Gly-
Pro-Hyp-Gly;

(SEQ ID NO: 47)
Pro-Hyp-Gly-Pro-Hyp-Gly-Pro-Hyp-Gly-Pro-Cys-Gly-Pro-Hyp-Gly-
Pro-Hyp-Gly;

(SEQ ID NO: 48)
Pro-Hyp-Gly-Pro-Hyp-Gly-Pro-Hyp-Gly-Pro-Hyp-Gly-Cys-Hyp-Gly-Pro-Hyp-Gly
Pro-Hyp-Gly;

(SEQ ID NO: 49)
Pro-Hyp-Gly-Pro-Hyp-Gly-Pro-Hyp-Gly-Pro-Hyp-Gly-Pro-Cys-Gly-Pro-Hyp-Gly-
Pro-Hyp-Gly;

(SEQ ID NO: 50)
Pro-Hyp-Gly-Pro-Hyp-Gly-Pro-Hyp-Gly-Pro-Hyp-Gly-Pro-Hyp-Gly-Cys-Hyp-Gly
Pro-Hyp-Gly;

(SEQ ID NO: 51)
Pro-Hyp-Gly-Pro-Hyp-Gly-Pro-Hyp-Gly-Pro-Hyp-Gly-Pro-Hyp-Gly-Pro-Cys-Gly-
Pro-Hyp-Gly;

(SEQ ID NO: 52)
Pro-Hyp-Gly-Pro-Hyp-Gly-Pro-Hyp-Gly-Pro-Hyp-Gly-Pro-Hyp-Gly-Pro-Hyp-Gly-
Cys-Hyp-Gly;

(SEQ ID NO: 53)
Pro-Hyp-Gly-Pro-Hyp-Gly-Pro-Hyp-Gly-Pro-Hyp-Gly-Pro-Hyp-Gly-Pro-Hyp-Gly-
Pro-Cys-Gly;

(SEQ ID NO: 54)
Cys-Flp-Gly-Pro-Flp-Gly-Pro-Flp-Gly-Pro-Flp-Gly-Pro-Flp-Gly-Pro-Flp-Gly-Pro-
Flp-Gly;

(SEQ ID NO: 55)
Pro-Cys-Gly-Pro-Flp-Gly-Pro-Flp-Gly-Pro-Flp-Gly-Pro-Flp-Gly-Pro-Flp-Gly-Pro-
Flp-Gly;

(SEQ ID NO: 56)
Pro-Flp-Gly-Cys-Flp-Gly-Pro-Flp-Gly-Pro-Flp-Gly-Pro-Flp-Gly-Pro-Flp-Gly-Pro-
Flp-Gly;

(SEQ ID NO: 57)
Pro-Flp-Gly-Pro-Cys-Gly-Pro-Flp-Gly-Pro-Flp-Gly-Pro-Flp-Gly-Pro-Flp-Gly-Pro-
Flp-Gly;

-continued (SEQ ID NO: 58)
Pro-Flp-Gly-Pro-Flp-Gly-Cys-Flp-Gly-Pro-Flp-Gly-Pro-Flp-Gly-Pro-Flp-Gly;

(SEQ ID NO: 59)
Pro-Flp-Gly-Pro-Flp-Gly-Pro-Flp-Gly-Cys-Flp-Gly-Pro-Flp-Gly-Pro-Flp-Gly;

(SEQ ID NO: 60)
Pro-Flp-Gly-Pro-Flp-Gly-Pro-Flp-Gly-Pro-Cys-Gly-Pro-Flp-Gly-Pro-Flp-Gly;

(SEQ ID NO: 61)
Pro-Flp-Gly-Pro-Flp-Gly-Pro-Flp-Gly-Pro-Flp-Gly-Cys-Flp-Gly-Pro-Flp-Gly;

(SEQ ID NO: 62)
Pro-Flp-Gly-Pro-Flp-Gly-Pro-Flp-Gly-Pro-Flp-Gly-Pro-Cys-Gly-Pro-Flp-Gly-Flp-Gly;

(SEQ ID NO: 63)
Pro-Flp-Gly-Pro-Flp-Gly-Pro-Flp-Gly-Pro-Flp-Gly-Pro-Flp-Gly-Cys-Flp-Gly-Pro-Flp-Gly;

(SEQ ID NO: 64)
Pro-Flp-Gly-Pro-Flp-Gly-Pro-Flp-Gly-Pro-Flp-Gly-Pro-Flp-Gly-Pro-Cys-Gly-Pro-Flp-Gly;

(SEQ ID NO: 65)
Pro-Flp-Gly-Pro-Flp-Gly-Pro-Flp-Gly-Pro-Flp-Gly-Pro-Flp-Gly-Pro-Flp-Gly-Cys-Flp-Gly;

(SEQ ID NO: 66)
Pro-Flp-Gly-Pro-Flp-Gly-Pro-Flp-Gly-Pro-Flp-Gly-Pro-Flp-Gly-Pro-Flp-Gly-Pro-Cys-Gly;

(SEQ ID NO: 67)
Cys-Flp-Gly-Pro-Flp-Gly-Pro-Flp-Gly-Pro-Flp-Gly-Pro-Flp-Gly-Pro-Flp-Gly-Pro-Flp-Gly;

(SEQ ID NO: 68)
Pro-Cys-Gly-Pro-Flp-Gly-Pro-Flp-Gly-Pro-Flp-Gly-Pro-Flp-Gly-Pro-Flp-Gly-Pro-Flp-Gly;

(SEQ ID NO: 69)
Pro-Flp-Gly-Cys-Flp-Gly-Pro-Flp-Gly-Pro-Flp-Gly-Pro-Flp-Gly-Pro-Flp-Gly-Pro-Flp-Gly;

(SEQ ID NO: 70)
Pro-Flp-Gly-Pro-Cys-Gly-Pro-Flp-Gly-Pro-Flp-Gly-Pro-Flp-Gly-Pro-Flp-Gly-Pro-Flp-Gly;

(SEQ ID NO: 71)
Pro-Flp-Gly-Pro-Flp-Gly-Cys-Flp-Gly-Pro-Flp-Gly-Pro-Flp-Gly-Pro-Flp-Gly-Pro-Flp-Gly;

(SEQ ID NO: 72)
Pro-Flp-Gly-Pro-Flp-Gly-Pro-Cys-Gly-Pro-Flp-Gly-Pro-Flp-Gly-Pro-Flp-Gly-Pro-Flp-Gly;

(SEQ ID NO: 73)
Pro-Flp-Gly-Pro-Flp-Gly-Pro-Flp-Gly-Cys-Flp-Gly-Pro-Flp-Gly-Pro-Flp-Gly-Pro-Flp-Gly;

-continued (SEQ ID NO: 74)
Pro-Flp-Gly-Pro-Flp-Gly-Pro-Flp-Gly-Pro-Cys-Gly-Pro-Flp-Gly-Pro-Flp-Gly-Pro-Flp-Gly;

(SEQ ID NO: 75)
Pro-Flp-Gly-Pro-Flp-Gly-Pro-Flp-Gly-Pro-Flp-Gly-Cys-Flp-Gly-Pro-Flp-Gly-Pro-Flp-Gly;

(SEQ ID NO: 76)
Pro-Flp-Gly-Pro-Flp-Gly-Pro-Flp-Gly-Pro-Flp-Gly-Pro-Cys-Gly-Pro-Flp-Gly-Pro-Flp-Gly;

(SEQ ID NO: 77)
Pro-Flp-Gly-Pro-Flp-Gly-Pro-Flp-Gly-Pro-Flp-Gly-Pro-Flp-Gly-Cys-Flp-Gly-Pro-Flp-Gly;

(SEQ ID NO: 78)
Pro-Flp-Gly-Pro-Flp-Gly-Pro-Flp-Gly-Pro-Flp-Gly-Pro-Flp-Gly-Pro-Cys-Gly-Pro-Flp-Gly;

(SEQ ID NO: 79)
Pro-Flp-Gly-Pro-Flp-Gly-Pro-Flp-Gly-Pro-Flp-Gly-Pro-Flp-Gly-Pro-Flp-Gly-Cys-Flp-Gly;

(SEQ ID NO: 80)
Pro-Flp-Gly-Pro-Flp-Gly-Pro-Flp-Gly-Pro-Flp-Gly-Pro-Flp-Gly-Pro-Flp-Gly-Pro-Cys-Gly;

(SEQ ID NO: 81)
Cys-Hyp-Gly-Flp-Hyp-Gly-Flp-Hyp-Gly-Flp-Hyp-Gly-Flp-Hyp-Gly-Flp-Hyp-Gly-Flp-Hyp-Gly;

(SEQ ID NO: 82)
Flp-Cys-Gly-Flp-Hyp-Gly-Flp-Hyp-Gly-Flp-Hyp-Gly-Flp-Hyp-Gly-Flp-Hyp-Gly-Flp-Hyp-Gly;

(SEQ ID NO: 83)
Flp-Hyp-Gly-Cys-Hyp-Gly-Flp-Hyp-Gly-Flp-Hyp-Gly-Flp-Hyp-Gly-Flp-Hyp-Gly-Flp-Hyp-Gly;

(SEQ ID NO: 84)
Flp-Hyp-Gly-Flp-Cys-Gly-Flp-Hyp-Gly-Flp-Hyp-Gly-Flp-Hyp-Gly-Flp-Hyp-Gly-Flp-Hyp-Gly;

(SEQ ID NO: 85)
Flp-Hyp-Gly-Flp-Hyp-Gly-Cys-Hyp-Gly-Flp-Hyp-Gly-Flp-Hyp-Gly-Flp-Hyp-Gly-Flp-Hyp-Gly;

(SEQ ID NO: 86)
Flp-Hyp-Gly-Flp-Hyp-Gly-Flp-Cys-Gly-Flp-Hyp-Gly-Flp-Hyp-Gly-Flp-Hyp-Gly-Flp-Hyp-Gly;

(SEQ ID NO: 87)
Flp-Hyp-Gly-Flp-Hyp-Gly-Flp-Hyp-Gly-Cys-Hyp-Gly-Flp-Hyp-Gly-Flp-Hyp-Gly-Flp-Hyp-Gly;

(SEQ ID NO: 88)
Flp-Hyp-Gly-Flp-Hyp-Gly-Flp-Hyp-Gly-Flp-Cys-Gly-Flp-Hyp-Gly-Flp-Hyp-Gly-Flp-Hyp-Gly;

(SEQ ID NO: 89)
Flp-Hyp-Gly-Flp-Hyp-Gly-Flp-Hyp-Gly-Flp-Hyp-Gly-Cys-Hyp-Gly-Flp-Hyp-Gly-Flp-Hyp-Gly;

```
                                                       (SEQ ID NO: 90)
Flp-Hyp-Gly-Flp-Hyp-Gly-Flp-Hyp-Gly-Flp-Hyp-Gly-Flp-Cys-Gly-Flp-Hyp-Gly-

Flp-Hyp-Gly;

(SEQ ID NO: 91)
Flp-Hyp-Gly-Flp-Hyp-Gly-Flp-Hyp-Gly-Flp-Hyp-Gly-Flp-Hyp-Gly-Cys-Hyp-Gly-

Flp-Hyp-Gly;

(SEQ ID NO: 92)
Flp-Hyp-Gly-Flp-Hyp-Gly-Flp-Hyp-Gly-Flp-Hyp-Gly-Flp-Hyp-Gly-Flp-Cys-Gly-

Flp-Hyp-Gly;

(SEQ ID NO: 93)
Flp-Hyp-Gly-Flp-Hyp-Gly-Flp-Hyp-Gly-Flp-Hyp-Gly-Flp-Hyp-Gly-Flp-Hyp-Gly-

Cys-Hyp-Gly;

(SEQ ID NO: 94)
Flp-Hyp-Gly-Flp-Hyp-Gly-Flp-Hyp-Gly-Flp-Hyp-Gly-Flp-Hyp-Gly-Flp-Hyp-Gly-

Flp-Cys-Gly;

(SEQ ID NO: 95)
Cys-Clp-Gly-Pro-Clp-Gly-Pro-Clp-Gly-Pro-Clp-Gly-Pro-Clp-Gly-Pro-Clp-Gly-Pro-

Clp-Gly;

(SEQ ID NO: 96)
Pro-Cys-Gly-Pro-Clp-Gly-Pro-Clp-Gly-Pro-Clp-Gly-Pro-Clp-Gly-Pro-Clp-Gly-Pro-

Clp-Gly;

(SEQ ID NO: 97)
Pro-Clp-Gly-Cys-Clp-Gly-Pro-Clp-Gly-Pro-Clp-Gly-Pro-Clp-Gly-Pro-Clp-Gly-Pro-

Clp-Gly;

(SEQ ID NO: 98)
Pro-Clp-Gly-Pro-Cys-Gly-Pro-Clp-Gly-Pro-Clp-Gly-Pro-Clp-Gly-Pro-Clp-Gly-Pro-

Clp-Gly;

(SEQ ID NO: 99)
Pro-Clp-Gly-Pro-Clp-Gly-Cys-Clp-Gly-Pro-Clp-Gly-Pro-Clp-Gly-Pro-Clp-Gly-Pro-

Clp-Gly;

(SEQ ID NO: 100)
Pro-Clp-Gly-Pro-Clp-Gly-Pro-Clp-Gly-Cys-Clp-Gly-Pro-Clp-Gly-Pro-Clp-Gly-Pro-

Clp-Gly;

(SEQ ID NO: 101)
Pro-Clp-Gly-Pro-Clp-Gly-Pro-Clp-Gly-Pro-Cys-Gly-Pro-Clp-Gly-Pro-Clp-Gly-Pro-

Clp-Gly;

(SEQ ID NO: 102)
Pro-Clp-Gly-Pro-Clp-Gly-Pro-Clp-Gly-Pro-Clp-Gly-Cys-Clp-Gly-Pro-Clp-Gly-Pro-

Clp-Gly;

(SEQ ID NO: 103)
Pro-Clp-Gly-Pro-Clp-Gly-Pro-Clp-Gly-Pro-Clp-Gly-Pro-Cys-Gly-Pro-Clp-Gly-Pro-

Clp-Gly;

(SEQ ID NO: 104)
Pro-Clp-Gly-Pro-Clp-Gly-Pro-Clp-Gly-Pro-Clp-Gly-Pro-Clp-Gly-Cys-Clp-Gly-Pro-

Clp-Gly;

(SEQ ID NO: 105)
Pro-Clp-Gly-Pro-Clp-Gly-Pro-Clp-Gly-Pro-Clp-Gly-Pro-Clp-Gly-Pro-Cys-Gly-Pro-

Clp-Gly;
```

-continued (SEQ ID NO: 106)
Pro-Clp-Gly-Pro-Clp-Gly-Pro-Clp-Gly-Pro-Clp-Gly-Pro-Clp-Gly-Cys-Clp-Gly;

(SEQ ID NO: 107)
Pro-Clp-Gly-Pro-Clp-Gly-Pro-Clp-Gly-Pro-Clp-Gly-Pro-Clp-Gly-Pro-Cys-Gly;

(SEQ ID NO: 108)
Cys-Clp-Gly-Pro-Clp-Gly-Pro-Clp-Gly-Pro-Clp-Gly-Pro-Clp-Gly-Pro-Clp-Gly;

(SEQ ID NO: 109)
Pro-Cys-Gly-Pro-Clp-Gly-Pro-Clp-Gly-Pro-Clp-Gly-Pro-Clp-Gly-Pro-Clp-Gly;

(SEQ ID NO: 110)
Pro-Clp-Gly-Cys-Clp-Gly-Pro-Clp-Gly-Pro-Clp-Gly-Pro-Clp-Gly-Pro-Clp-Gly;

(SEQ ID NO: 111)
Pro-Clp-Gly-Pro-Cys-Gly-Pro-Clp-Gly-Pro-Clp-Gly-Pro-Clp-Gly-Pro-Clp-Gly;

(SEQ ID NO: 112)
Pro-Clp-Gly-Pro-Clp-Gly-Cys-Clp-Gly-Pro-Clp-Gly-Pro-Clp-Gly-Pro-Clp-Gly;

(SEQ ID NO: 113)
Pro-Clp-Gly-Pro-Clp-Gly-Pro-Cys-Gly-Pro-Clp-Gly-Pro-Clp-Gly-Pro-Clp-Gly;

(SEQ ID NO: 114)
Pro-Clp-Gly-Pro-Clp-Gly-Pro-Clp-Gly-Cys-Clp-Gly-Pro-Clp-Gly-Pro-Clp-Gly;

(SEQ ID NO: 115)
Pro-Clp-Gly-Pro-Clp-Gly-Pro-Clp-Gly-Pro-Cys-Gly-Pro-Clp-Gly-Pro-Clp-Gly;

(SEQ ID NO: 116)
Pro-Clp-Gly-Pro-Clp-Gly-Pro-Clp-Gly-Pro-Clp-Gly-Cys-Clp-Gly-Pro-Clp-Gly;

(SEQ ID NO: 117)
Pro-Clp-Gly-Pro-Clp-Gly-Pro-Clp-Gly-Pro-Clp-Gly-Pro-Cys-Gly-Pro-Clp-Gly;

(SEQ ID NO: 118)
Pro-Clp-Gly-Pro-Clp-Gly-Pro-Clp-Gly-Pro-Clp-Gly-Pro-Clp-Gly-Cys-Clp-Gly-Pro-Clp-Gly;

(SEQ ID NO: 119)
Pro-Clp-Gly-Pro-Clp-Gly-Pro-Clp-Gly-Pro-Clp-Gly-Pro-Clp-Gly-Pro-Cys-Gly-Pro-Clp-Gly;

(SEQ ID NO: 120)
Pro-Clp-Gly-Pro-Clp-Gly-Pro-Clp-Gly-Pro-Clp-Gly-Pro-Clp-Gly-Pro-Clp-Gly-Cys-Clp-Gly;

(SEQ ID NO: 121)
Pro-Clp-Gly-Pro-Clp-Gly-Pro-Clp-Gly-Pro-Clp-Gly-Pro-Clp-Gly-Pro-Clp-Gly-Pro-Cys-Gly;

-continued (SEQ ID NO: 122)
Cys-Hyp-Gly-Clp-Hyp-Gly-Clp-Hyp-Gly-Clp-Hyp-Gly-Clp-Hyp-Gly-Clp-Hyp-Gly-Clp-Hyp-Gly;

(SEQ ID NO: 123)
Clp-Cys-Gly-Clp-Hyp-Gly-Clp-Hyp-Gly-Clp-Hyp-Gly-Clp-Hyp-Gly-Clp-Hyp-Gly-Clp-Hyp-Gly;

(SEQ ID NO: 124)
Clp-Hyp-Gly-Cys-Hyp-Gly-Clp-Hyp-Gly-Clp-Hyp-Gly-Clp-Hyp-Gly-Clp-Hyp-Gly-Clp-Hyp-Gly;

(SEQ ID NO: 125)
Clp-Hyp-Gly-Clp-Cys-Gly-Clp-Hyp-Gly-Clp-Hyp-Gly-Clp-Hyp-Gly-Clp-Hyp-Gly-Clp-Hyp-Gly;

(SEQ ID NO: 126)
Clp-Hyp-Gly-Clp-Hyp-Gly-Cys-Hyp-Gly-Clp-Hyp-Gly-Clp-Hyp-Gly-Clp-Hyp-Gly-Clp-Hyp-Gly;

(SEQ ID NO: 127)
Clp-Hyp-Gly-Clp-Hyp-Gly-Clp-Cys-Gly-Clp-Hyp-Gly-Clp-Hyp-Gly-Clp-Hyp-Gly-Clp-Hyp-Gly;

(SEQ ID NO: 128)
Clp-Hyp-Gly-Clp-Hyp-Gly-Clp-Hyp-Gly-Cys-Hyp-Gly-Clp-Hyp-Gly-Clp-Hyp-Gly-Clp-Hyp-Gly;

(SEQ ID NO: 129)
Clp-Hyp-Gly-Clp-Hyp-Gly-Clp-Hyp-Gly-Clp-Cys-Gly-Clp-Hyp-Gly-Clp-Hyp-Gly-Clp-Hyp-Gly;

(SEQ ID NO: 130)
Clp-Hyp-Gly-Clp-Hyp-Gly-Clp-Hyp-Gly-Clp-Hyp-Gly-Cys-Hyp-Gly-Clp-Hyp-Gly-Clp-Hyp-Gly;

(SEQ ID NO: 131)
Clp-Hyp-Gly-Clp-Hyp-Gly-Clp-Hyp-Gly-Clp-Hyp-Gly-Clp-Cys-Gly-Clp-Hyp-Gly-Clp-Hyp-Gly;

(SEQ ID NO: 132)
Clp-Hyp-Gly-Clp-Hyp-Gly-Clp-Hyp-Gly-Clp-Hyp-Gly-Clp-Hyp-Gly-Cys-Hyp-Gly-Clp-Hyp-Gly;

(SEQ ID NO: 133)
Clp-Hyp-Gly-Clp-Hyp-Gly-Clp-Hyp-Gly-Clp-Hyp-Gly-Clp-Hyp-Gly-Clp-Cys-Gly-Clp-Hyp-Gly;

(SEQ ID NO: 134)
Clp-Hyp-Gly-Clp-Hyp-Gly-Clp-Hyp-Gly-Clp-Hyp-Gly-Clp-Hyp-Gly-Clp-Hyp-Gly-Cys-Hyp-Gly;
and (SEQ ID NO: 135)
Clp-Hyp-Gly-Clp-Hyp-Gly-Clp-Hyp-Gly-Clp-Hyp-Gly-Clp-Hyp-Gly-Clp-Hyp-Gly-Clp-Cys-Gly.

In certain other embodiments of the invention, the collagen mimetic peptide may comprise, consist of or have an amino acid sequence that is or corresponds to a 21-mer of any one of SEQ ID NOs:1-9, in which at least one methionine (Met) residue has been substituted for at least one of the proline residues in SEQ ID NO:1, at least one of the hydroxyproline residues in SEQ ID NOs:2-3 and 6, at least one of the fluoroproline residues in SEQ ID NOs:4-6, or at least one of the chloroproline residues in SEQ ID NOs:7-9, yielding, for example, the following sequences:

(SEQ ID NO: 136)
Pro-Pro-Gly-Pro-Pro-Gly-Met-Pro-Gly-Pro-Pro-Gly-Pro-Pro-Gly-Pro-Pro-Gly-Pro-;
Pro-Gly;

(SEQ ID NO: 137)
Hyp-Pro-Gly-Hyp-Pro-Gly-Met-Pro-Gly-Hyp-Pro-Gly-Hyp-Pro-Gly-Hyp-Pro-Gly-;
Hyp-Pro-Gly;

(SEQ ID NO: 138)
Pro-Hyp-Gly-Pro-Hyp-Gly-Pro-Met-Gly-Pro-Hyp-Gly-Pro-Hyp-Gly-Pro-Hyp-Gly-
Pro-Hyp-Gly;

(SEQ ID NO: 139)
Pro-Flp-Gly-Pro-Flp-Gly-Pro-Met-Gly-Pro-Flp-Gly-Pro-Flp-Gly-Pro-Flp-Gly-Pro-
Flp-Gly;

(SEQ ID NO: 140)
Pro-Clp-Gly-Pro-Clp-Gly-Pro-Met-Gly-Pro-Clp-Gly-Pro-Clp-Gly-Pro-Clp-Gly-Pro-
Clp-Gly;

(SEQ ID NO: 141)
Met-Pro-Gly-Pro-Pro-Gly-Pro-Pro-Gly-Pro-Pro-Gly-Pro-Pro-Gly-Pro-Pro-Gly-Pro-
Pro-Gly;

(SEQ ID NO: 142)
Pro-Met-Gly-Pro-Pro-Gly-Pro-Pro-Gly-Pro-Pro-Gly-Pro-Pro-Gly-Pro-Pro-Gly-Pro-
Pro-Gly;

(SEQ ID NO: 143)
Pro-Pro-Gly-Met-Pro-Gly-Pro-Pro-Gly-Pro-Pro-Gly-Pro-Pro-Gly-Pro-Pro-Gly-Pro-
Pro-Gly;

(SEQ ID NO: 144)
Pro-Pro-Gly-Pro-Met-Gly-Pro-Pro-Gly-Pro-Pro-Gly-Pro-Pro-Gly-Pro-Pro-Gly-Pro-
Pro-Gly;

(SEQ ID NO: 145)
Pro-Pro-Gly-Pro-Pro-Gly-Pro-Met-Gly-Pro-Pro-Gly-Pro-Pro-Gly-Pro-Pro-Gly-Pro-
Pro-Gly;

(SEQ ID NO: 146)
Pro-Pro-Gly-Pro-Pro-Gly-Pro-Pro-Gly-Met-Pro-Gly-Pro-Pro-Gly-Pro-Pro-Gly-Pro-
Pro-Gly;

(SEQ ID NO: 147)
Pro-Pro-Gly-Pro-Pro-Gly-Pro-Pro-Gly-Pro-Met-Gly-Pro-Pro-Gly-Pro-Pro-Gly-Pro-
Pro-Gly;

(SEQ ID NO: 148)
Pro-Pro-Gly-Pro-Pro-Gly-Pro-Pro-Gly-Pro-Pro-Gly-Met-Pro-Gly-Pro-Pro-Gly-Pro-
Pro-Gly;

(SEQ ID NO: 149)
Pro-Pro-Gly-Pro-Pro-Gly-Pro-Pro-Gly-Pro-Pro-Gly-Pro-Met-Gly-Pro-Pro-Gly-Pro-
Pro-Gly;

(SEQ ID NO: 150)
Pro-Pro-Gly-Pro-Pro-Gly-Pro-Pro-Gly-Pro-Pro-Gly-Pro-Pro-Gly-Met-Gly-Pro-
Pro-Gly;

(SEQ ID NO: 151)
Pro-Pro-Gly-Pro-Pro-Gly-Pro-Pro-Gly-Pro-Pro-Gly-Pro-Pro-Gly-Pro-Met-Gly-Pro-
Pro-Gly;

```
                                                    (SEQ ID NO: 152)
Pro-Pro-Gly-Pro-Pro-Gly-Pro-Pro-Gly-Pro-Pro-Gly-Pro-Pro-Gly-Met-

Pro-Gly;

(SEQ ID NO: 153)
Pro-Pro-Gly-Pro-Pro-Gly-Pro-Pro-Gly-Pro-Pro-Gly-Pro-Pro-Gly-Pro-

Met-Gly;

(SEQ ID NO: 154)
Met-Pro-Gly-Hyp-Pro-Gly-Hyp-Pro-Gly-Hyp-Pro-Gly-Hyp-Pro-Gly-

Hyp-Pro-Gly;

(SEQ ID NO: 155)
Hyp-Met-Gly-Hyp-Pro-Gly-Hyp-Pro-Gly-Hyp-Pro-Gly-Hyp-Pro-Gly-

Hyp-Pro-Gly;

(SEQ ID NO: 156)
Hyp-Pro-Gly-Met-Pro-Gly-Hyp-Pro-Gly-Hyp-Pro-Gly-Hyp-Pro-Gly-

Hyp-Pro-Gly;

(SEQ ID NO: 157)
Hyp-Pro-Gly-Hyp-Met-Gly-Hyp-Pro-Gly-Hyp-Pro-Gly-Hyp-Pro-Gly-

Hyp-Pro-Gly;

(SEQ ID NO: 158)
Hyp-Pro-Gly-Hyp-Pro-Gly-Hyp-Met-Gly-Hyp-Pro-Gly-Hyp-Pro-Gly-

Hyp-Pro-Gly;

(SEQ ID NO: 159)
Hyp-Pro-Gly-Hyp-Pro-Gly-Hyp-Pro-Gly-Met-Pro-Gly-Hyp-Pro-Gly-

Hyp-Pro-Gly;

(SEQ ID NO: 160)
Hyp-Pro-Gly-Hyp-Pro-Gly-Hyp-Pro-Gly-Hyp-Met-Gly-Hyp-Pro-Gly-

Hyp-Pro-Gly;

(SEQ ID NO: 161)
Hyp-Pro-Gly-Hyp-Pro-Gly-Hyp-Pro-Gly-Hyp-Pro-Gly-Met-Pro-Gly-

Hyp-Pro-Gly;

(SEQ ID NO: 162)
Hyp-Pro-Gly-Hyp-Pro-Gly-Hyp-Pro-Gly-Hyp-Pro-Gly-Hyp-Met-Gly-

Hyp-Pro-Gly;

(SEQ ID NO: 163)
Hyp-Pro-Gly-Hyp-Pro-Gly-Hyp-Pro-Gly-Hyp-Pro-Gly-Hyp-Pro-Gly-Met-Pro-Gly-

Hyp-Pro-Gly;

(SEQ ID NO: 164)
Hyp-Pro-Gly-Hyp-Pro-Gly-Hyp-Pro-Gly-Hyp-Pro-Gly-Hyp-Pro-Gly-Hyp-Met-Gly-

Hyp-Pro-Gly;

(SEQ ID NO: 165)
Hyp-Pro-Gly-Hyp-Pro-Gly-Hyp-Pro-Gly-Hyp-Pro-Gly-Hyp-Pro-Gly-Hyp-Pro-Gly-

Met-Pro-Gly;

(SEQ ID NO: 166)
Hyp-Pro-Gly-Hyp-Pro-Gly-Hyp-Pro-Gly-Hyp-Pro-Gly-Hyp-Pro-Gly-Hyp-Pro-Gly-

Hyp-Met-Gly;

(SEQ ID NO: 167)
Met-Hyp-Gly-Pro-Hyp-Gly-Pro-Hyp-Gly-Pro-Hyp-Gly-Pro-Hyp-Gly-

Pro-Hyp-Gly;
```

-continued

```
                                                (SEQ ID NO: 168)
Pro-Met-Gly-Pro-Hyp-Gly-Pro-Hyp-Gly-Pro-Hyp-Gly-Pro-Hyp-Gly-

Pro-Hyp-Gly;

(SEQ ID NO: 169)
Pro-Hyp-Gly-Met-Hyp-Gly-Pro-Hyp-Gly-Pro-Hyp-Gly-Pro-Hyp-Gly-

Pro-Hyp-Gly;

(SEQ ID NO: 170)
Pro-Hyp-Gly-Pro-Met-Gly-Pro-Hyp-Gly-Pro-Hyp-Gly-Pro-Hyp-Gly-

Pro-Hyp-Gly;

(SEQ ID NO: 171)
Pro-Hyp-Gly-Pro-Hyp-Gly-Met-Hyp-Gly-Pro-Hyp-Gly-Pro-Hyp-Gly-

Pro-Hyp-Gly;

(SEQ ID NO: 172)
Pro-Hyp-Gly-Pro-Hyp-Gly-Pro-Hyp-Gly-Met-Hyp-Gly-Pro-Hyp-Gly-

Pro-Hyp-Gly;

(SEQ ID NO: 173)
Pro-Hyp-Gly-Pro-Hyp-Gly-Pro-Hyp-Gly-Pro-Met-Gly-Pro-Hyp-Gly-

Pro-Hyp-Gly;

(SEQ ID NO: 174)
Pro-Hyp-Gly-Pro-Hyp-Gly-Pro-Hyp-Gly-Pro-Hyp-Gly-Met-Hyp-Gly-

Pro-Hyp-Gly;

(SEQ ID NO: 175)
Pro-Hyp-Gly-Pro-Hyp-Gly-Pro-Hyp-Gly-Pro-Hyp-Gly-Pro-Met-Gly-

Pro-Hyp-Gly;

(SEQ ID NO: 176)
Pro-Hyp-Gly-Pro-Hyp-Gly-Pro-Hyp-Gly-Pro-Hyp-Gly-Pro-Hyp-Gly-Met-Hyp-Gly-

Pro-Hyp-Gly;

(SEQ ID NO: 177)
Pro-Hyp-Gly-Pro-Hyp-Gly-Pro-Hyp-Gly-Pro-Hyp-Gly-Pro-Hyp-Gly-Pro-Met-Gly-

Pro-Hyp-Gly;

(SEQ ID NO: 178)
Pro-Hyp-Gly-Pro-Hyp-Gly-Pro-Hyp-Gly-Pro-Hyp-Gly-Pro-Hyp-Gly-Pro-Hyp-Gly-

Met-Hyp-Gly;

(SEQ ID NO: 179)
Pro-Hyp-Gly-Pro-Hyp-Gly-Pro-Hyp-Gly-Pro-Hyp-Gly-Pro-Hyp-Gly-Pro-Hyp-Gly-

Pro-Met-Gly;

(SEQ ID NO: 180)
Met-Flp-Gly-Pro-Flp-Gly-Pro-Flp-Gly-Pro-Flp-Gly-Pro-Flp-Gly-Pro-Flp-Gly-Pro-

Flp-Gly;

(SEQ ID NO: 181)
Pro-Met-Gly-Pro-Flp-Gly-Pro-Flp-Gly-Pro-Flp-Gly-Pro-Flp-Gly-Pro-Flp-Gly-Pro-

Flp-Gly;

(SEQ ID NO: 182)
Pro-Flp-Gly-Met-Flp-Gly-Pro-Flp-Gly-Pro-Flp-Gly-Pro-Flp-Gly-Pro-Flp-Gly-Pro-

Flp-Gly;

(SEQ ID NO: 183)
Pro-Flp-Gly-Pro-Met-Gly-Pro-Flp-Gly-Pro-Flp-Gly-Pro-Flp-Gly-Pro-Flp-Gly-Pro-

Flp-Gly;
```

(SEQ ID NO: 184)
Pro-Flp-Gly-Pro-Flp-Gly-Met-Flp-Gly-Pro-Flp-Gly-Pro-Flp-Gly-Pro-Flp-Gly;

(SEQ ID NO: 185)
Pro-Flp-Gly-Pro-Flp-Gly-Pro-Flp-Gly-Met-Flp-Gly-Pro-Flp-Gly-Pro-Flp-Gly;

(SEQ ID NO: 186)
Pro-Flp-Gly-Pro-Flp-Gly-Pro-Flp-Gly-Pro-Met-Gly-Pro-Flp-Gly-Pro-Flp-Gly;

(SEQ ID NO: 187)
Pro-Flp-Gly-Pro-Flp-Gly-Pro-Flp-Gly-Pro-Flp-Gly-Met-Flp-Gly-Pro-Flp-Gly;

(SEQ ID NO: 188)
Pro-Flp-Gly-Pro-Flp-Gly-Pro-Flp-Gly-Pro-Flp-Gly-Pro-Met-Gly-Pro-Flp-Gly;

(SEQ ID NO: 189)
Pro-Flp-Gly-Pro-Flp-Gly-Pro-Flp-Gly-Pro-Flp-Gly-Pro-Flp-Gly-Met-Flp-Gly-Pro-Flp-Gly;

(SEQ ID NO: 190)
Pro-Flp-Gly-Pro-Flp-Gly-Pro-Flp-Gly-Pro-Flp-Gly-Pro-Flp-Gly-Pro-Met-Gly-Pro-Flp-Gly;

(SEQ ID NO: 191)
Pro-Flp-Gly-Pro-Flp-Gly-Pro-Flp-Gly-Pro-Flp-Gly-Pro-Flp-Gly-Pro-Flp-Gly-Met-Flp-Gly;

(SEQ ID NO: 192)
Pro-Flp-Gly-Pro-Flp-Gly-Pro-Flp-Gly-Pro-Flp-Gly-Pro-Flp-Gly-Pro-Flp-Gly-Pro-Met-Gly;

(SEQ ID NO: 193)
Met-Flp-Gly-Pro-Flp-Gly-Pro-Flp-Gly-Pro-Flp-Gly-Pro-Flp-Gly-Pro-Flp-Gly-Pro-Flp-Gly;

(SEQ ID NO: 194)
Pro-Met-Gly-Pro-Flp-Gly-Pro-Flp-Gly-Pro-Flp-Gly-Pro-Flp-Gly-Pro-Flp-Gly-Pro-Flp-Gly;

(SEQ ID NO: 195)
Pro-Flp-Gly-Met-Flp-Gly-Pro-Flp-Gly-Pro-Flp-Gly-Pro-Flp-Gly-Pro-Flp-Gly-Pro-Flp-Gly;

(SEQ ID NO: 196)
Pro-Flp-Gly-Pro-Met-Gly-Pro-Flp-Gly-Pro-Flp-Gly-Pro-Flp-Gly-Pro-Flp-Gly-Pro-Flp-Gly;

(SEQ ID NO: 197)
Pro-Flp-Gly-Pro-Flp-Gly-Met-Flp-Gly-Pro-Flp-Gly-Pro-Flp-Gly-Pro-Flp-Gly-Pro-Flp-Gly;

(SEQ ID NO: 198)
Pro-Flp-Gly-Pro-Flp-Gly-Pro-Met-Gly-Pro-Flp-Gly-Pro-Flp-Gly-Pro-Flp-Gly-Pro-Flp-Gly;

(SEQ ID NO: 199)
Pro-Flp-Gly-Pro-Flp-Gly-Pro-Flp-Gly-Met-Flp-Gly-Pro-Flp-Gly-Pro-Flp-Gly-Pro-Flp-Gly;

-continued (SEQ ID NO: 200)
Pro-Flp-Gly-Pro-Flp-Gly-Pro-Flp-Gly-Pro-Met-Gly-Pro-Flp-Gly-Pro-Flp-Gly-Pro-Flp-Gly;

(SEQ ID NO: 201)
Pro-Flp-Gly-Pro-Flp-Gly-Pro-Flp-Gly-Pro-Flp-Gly-Met-Flp-Gly-Pro-Flp-Gly-Pro-Flp-Gly;

(SEQ ID NO: 202)
Pro-Flp-Gly-Pro-Flp-Gly-Pro-Flp-Gly-Pro-Flp-Gly-Pro-Met-Gly-Pro-Flp-Gly-Pro-Flp-Gly;

(SEQ ID NO: 203)
Pro-Flp-Gly-Pro-Flp-Gly-Pro-Flp-Gly-Pro-Flp-Gly-Pro-Flp-Gly-Met-Flp-Gly-Pro-Flp-Gly;

(SEQ ID NO: 204)
Pro-Flp-Gly-Pro-Flp-Gly-Pro-Flp-Gly-Pro-Flp-Gly-Pro-Flp-Gly-Pro-Met-Gly-Pro-Flp-Gly;

(SEQ ID NO: 205)
Pro-Flp-Gly-Pro-Flp-Gly-Pro-Flp-Gly-Pro-Flp-Gly-Pro-Flp-Gly-Pro-Flp-Gly-Met-Flp-Gly;

(SEQ ID NO: 206)
Pro-Flp-Gly-Pro-Flp-Gly-Pro-Flp-Gly-Pro-Flp-Gly-Pro-Flp-Gly-Pro-Flp-Gly-Pro-Met-Gly;

(SEQ ID NO: 207)
Met-Hyp-Gly-Flp-Hyp-Gly-Flp-Hyp-Gly-Flp-Hyp-Gly-Flp-Hyp-Gly-Flp-Hyp-Gly-Flp-Hyp-Gly;

(SEQ ID NO: 208)
Flp-Met-Gly-Flp-Hyp-Gly-Flp-Hyp-Gly-Flp-Hyp-Gly-Flp-Hyp-Gly-Flp-Hyp-Gly-Flp-Hyp-Gly;

(SEQ ID NO: 209)
Flp-Hyp-Gly-Met-Hyp-Gly-Flp-Hyp-Gly-Flp-Hyp-Gly-Flp-Hyp-Gly-Flp-Hyp-Gly-Flp-Hyp-Gly;

(SEQ ID NO: 210)
Flp-Hyp-Gly-Flp-Met-Gly-Flp-Hyp-Gly-Flp-Hyp-Gly-Flp-Hyp-Gly-Flp-Hyp-Gly-Flp-Hyp-Gly;

(SEQ ID NO: 211)
Flp-Hyp-Gly-Flp-Hyp-Gly-Met-Hyp-Gly-Flp-Hyp-Gly-Flp-Hyp-Gly-Flp-Hyp-Gly-Flp-Hyp-Gly;

(SEQ ID NO: 212)
Flp-Hyp-Gly-Flp-Hyp-Gly-Flp-Met-Gly-Flp-Hyp-Gly-Flp-Hyp-Gly-Flp-Hyp-Gly-Flp-Hyp-Gly;

(SEQ ID NO: 213)
Flp-Hyp-Gly-Flp-Hyp-Gly-Flp-Hyp-Gly-Met-Hyp-Gly-Flp-Hyp-Gly-Flp-Hyp-Gly-Flp-Hyp-Gly;

(SEQ ID NO: 214)
Flp-Hyp-Gly-Flp-Hyp-Gly-Flp-Hyp-Gly-Flp-Met-Gly-Flp-Hyp-Gly-Flp-Hyp-Gly-Flp-Hyp-Gly;

(SEQ ID NO: 215)
Flp-Hyp-Gly-Flp-Hyp-Gly-Flp-Hyp-Gly-Flp-Hyp-Gly-Met-Hyp-Gly-Flp-Hyp-Gly-Flp-Hyp-Gly;

-continued (SEQ ID NO: 216)
Flp-Hyp-Gly-Flp-Hyp-Gly-Flp-Hyp-Gly-Flp-Hyp-Gly-Flp-Met-Gly-Flp-Hyp-Gly-Flp-Hyp-Gly;

(SEQ ID NO: 217)
Flp-Hyp-Gly-Flp-Hyp-Gly-Flp-Hyp-Gly-Flp-Hyp-Gly-Flp-Hyp-Gly-Met-Hyp-Gly-Flp-Hyp-Gly;

(SEQ ID NO: 218)
Flp-Hyp-Gly-Flp-Hyp-Gly-Flp-Hyp-Gly-Flp-Hyp-Gly-Flp-Hyp-Gly-Flp-Met-Gly-Flp-Hyp-Gly;

(SEQ ID NO: 219)
Flp-Hyp-Gly-Flp-Hyp-Gly-Flp-Hyp-Gly-Flp-Hyp-Gly-Flp-Hyp-Gly-Flp-Hyp-Gly-Met-Hyp-Gly;

(SEQ ID NO: 220)
Flp-Hyp-Gly-Flp-Hyp-Gly-Flp-Hyp-Gly-Flp-Hyp-Gly-Flp-Hyp-Gly-Flp-Hyp-Gly-Flp-Met-Gly;

(SEQ ID NO: 221)
Met-Clp-Gly-Pro-Clp-Gly-Pro-Clp-Gly-Pro-Clp-Gly-Pro-Clp-Gly-Pro-Clp-Gly-Pro-Clp-Gly;

(SEQ ID NO: 222)
Pro-Met-Gly-Pro-Clp-Gly-Pro-Clp-Gly-Pro-Clp-Gly-Pro-Clp-Gly-Pro-Clp-Gly-Pro-Clp-Gly;

(SEQ ID NO: 223)
Pro-Clp-Gly-Met-Clp-Gly-Pro-Clp-Gly-Pro-Clp-Gly-Pro-Clp-Gly-Pro-Clp-Gly-Pro-Clp-Gly;

(SEQ ID NO: 224)
Pro-Clp-Gly-Pro-Met-Gly-Pro-Clp-Gly-Pro-Clp-Gly-Pro-Clp-Gly-Pro-Clp-Gly-Pro-Clp-Gly;

(SEQ ID NO: 225)
Pro-Clp-Gly-Pro-Clp-Gly-Met-Clp-Gly-Pro-Clp-Gly-Pro-Clp-Gly-Pro-Clp-Gly-Pro-Clp-Gly;

(SEQ ID NO: 226)
Pro-Clp-Gly-Pro-Clp-Gly-Pro-Clp-Gly-Met-Clp-Gly-Pro-Clp-Gly-Pro-Clp-Gly-Pro-Clp-Gly;

(SEQ ID NO: 227)
Pro-Clp-Gly-Pro-Clp-Gly-Pro-Clp-Gly-Pro-Met-Gly-Pro-Clp-Gly-Pro-Clp-Gly-Pro-Clp-Gly;

(SEQ ID NO: 228)
Pro-Clp-Gly-Pro-Clp-Gly-Pro-Clp-Gly-Pro-Clp-Gly-Met-Clp-Gly-Pro-Clp-Gly-Pro-Clp-Gly;

(SEQ ID NO: 229)
Pro-Clp-Gly-Pro-Clp-Gly-Pro-Clp-Gly-Pro-Clp-Gly-Pro-Met-Gly-Pro-Clp-Gly-Pro-Clp-Gly;

(SEQ ID NO: 230)
Pro-Clp-Gly-Pro-Clp-Gly-Pro-Clp-Gly-Pro-Clp-Gly-Pro-Clp-Gly-Met-Clp-Gly-Pro-Clp-Gly;

(SEQ ID NO: 231)
Pro-Clp-Gly-Pro-Clp-Gly-Pro-Clp-Gly-Pro-Clp-Gly-Pro-Clp-Gly-Pro-Met-Gly-Pro-Clp-Gly;

-continued (SEQ ID NO: 232)
Pro-Clp-Gly-Pro-Clp-Gly-Pro-Clp-Gly-Pro-Clp-Gly-Pro-Clp-Gly-Met-Clp-Gly;

(SEQ ID NO: 233)
Pro-Clp-Gly-Pro-Clp-Gly-Pro-Clp-Gly-Pro-Clp-Gly-Pro-Clp-Gly-Pro-Clp-Gly-Pro-Met-Gly;

(SEQ ID NO: 234)
Met-Clp-Gly-Pro-Clp-Gly-Pro-Clp-Gly-Pro-Clp-Gly-Pro-Clp-Gly-Pro-Clp-Gly-Pro-Clp-Gly;

(SEQ ID NO: 235)
Pro-Met-Gly-Pro-Clp-Gly-Pro-Clp-Gly-Pro-Clp-Gly-Pro-Clp-Gly-Pro-Clp-Gly;

(SEQ ID NO: 236)
Pro-Clp-Gly-Met-Clp-Gly-Pro-Clp-Gly-Pro-Clp-Gly-Pro-Clp-Gly-Pro-Clp-Gly-Pro-Clp-Gly;

(SEQ ID NO: 237)
Pro-Clp-Gly-Pro-Met-Gly-Pro-Clp-Gly-Pro-Clp-Gly-Pro-Clp-Gly-Pro-Clp-Gly-Pro-Clp-Gly;

(SEQ ID NO: 238)
Pro-Clp-Gly-Pro-Clp-Gly-Met-Clp-Gly-Pro-Clp-Gly-Pro-Clp-Gly-Pro-Clp-Gly-Pro-Clp-Gly;

(SEQ ID NO: 239)
Pro-Clp-Gly-Pro-Clp-Gly-Pro-Met-Gly-Pro-Clp-Gly-Pro-Clp-Gly-Pro-Clp-Gly-Pro-Clp-Gly;

(SEQ ID NO: 240)
Pro-Clp-Gly-Pro-Clp-Gly-Pro-Clp-Gly-Met-Clp-Gly-Pro-Clp-Gly-Pro-Clp-Gly-Pro-Clp-Gly;

(SEQ ID NO: 241)
Pro-Clp-Gly-Pro-Clp-Gly-Pro-Clp-Gly-Pro-Met-Gly-Pro-Clp-Gly-Pro-Clp-Gly-Pro-Clp-Gly;

(SEQ ID NO: 242)
Pro-Clp-Gly-Pro-Clp-Gly-Pro-Clp-Gly-Pro-Clp-Gly-Met-Clp-Gly-Pro-Clp-Gly-Pro-Clp-Gly;

(SEQ ID NO: 243)
Pro-Clp-Gly-Pro-Clp-Gly-Pro-Clp-Gly-Pro-Clp-Gly-Pro-Met-Gly-Pro-Clp-Gly-Pro-Clp-Gly;

(SEQ ID NO: 244)
Pro-Clp-Gly-Pro-Clp-Gly-Pro-Clp-Gly-Pro-Clp-Gly-Pro-Clp-Gly-Met-Clp-Gly-Pro-Clp-Gly;

(SEQ ID NO: 245)
Pro-Clp-Gly-Pro-Clp-Gly-Pro-Clp-Gly-Pro-Clp-Gly-Pro-Clp-Gly-Pro-Met-Gly-Pro-Clp-Gly;

(SEQ ID NO: 246)
Pro-Clp-Gly-Pro-Clp-Gly-Pro-Clp-Gly-Pro-Clp-Gly-Pro-Clp-Gly-Pro-Clp-Gly-Met-Clp-Gly;

(SEQ ID NO: 247)
Pro-Clp-Gly-Pro-Clp-Gly-Pro-Clp-Gly-Pro-Clp-Gly-Pro-Clp-Gly-Pro-Clp-Gly-Pro-Met-Gly;

-continued (SEQ ID NO: 248)
Met-Hyp-Gly-Clp-Hyp-Gly-Clp-Hyp-Gly-Clp-Hyp-Gly-Clp-Hyp-Gly-Clp-Hyp-Gly-Clp-Hyp-Gly;

(SEQ ID NO: 249)
Clp-Met-Gly-Clp-Hyp-Gly-Clp-Hyp-Gly-Clp-Hyp-Gly-Clp-Hyp-Gly-Clp-Hyp-Gly-Clp-Hyp-Gly;

(SEQ ID NO: 250)
Clp-Hyp-Gly-Met-Hyp-Gly-Clp-Hyp-Gly-Clp-Hyp-Gly-Clp-Hyp-Gly-Clp-Hyp-Gly-Clp-Hyp-Gly;

(SEQ ID NO: 251)
Clp-Hyp-Gly-Clp-Met-Gly-Clp-Hyp-Gly-Clp-Hyp-Gly-Clp-Hyp-Gly-Clp-Hyp-Gly-Clp-Hyp-Gly;

(SEQ ID NO: 252)
Clp-Hyp-Gly-Clp-Hyp-Gly-Met-Hyp-Gly-Clp-Hyp-Gly-Clp-Hyp-Gly-Clp-Hyp-Gly-Clp-Hyp-Gly;

(SEQ ID NO: 253)
Clp-Hyp-Gly-Clp-Hyp-Gly-Clp-Met-Gly-Clp-Hyp-Gly-Clp-Hyp-Gly-Clp-Hyp-Gly-Clp-Hyp-Gly;

(SEQ ID NO: 254)
Clp-Hyp-Gly-Clp-Hyp-Gly-Clp-Hyp-Gly-Met-Hyp-Gly-Clp-Hyp-Gly-Clp-Hyp-Gly-Clp-Hyp-Gly;

(SEQ ID NO: 255)
Clp-Hyp-Gly-Clp-Hyp-Gly-Clp-Hyp-Gly-Clp-Met-Gly-Clp-Hyp-Gly-Clp-Hyp-Gly-Clp-Hyp-Gly;

(SEQ ID NO: 256)
Clp-Hyp-Gly-Clp-Hyp-Gly-Clp-Hyp-Gly-Clp-Hyp-Gly-Met-Hyp-Gly-Clp-Hyp-Gly-Clp-Hyp-Gly;

(SEQ ID NO: 257)
Clp-Hyp-Gly-Clp-Hyp-Gly-Clp-Hyp-Gly-Clp-Hyp-Gly-Clp-Met-Gly-Clp-Hyp-Gly-Clp-Hyp-Gly;

(SEQ ID NO: 258)
Clp-Hyp-Gly-Clp-Hyp-Gly-Clp-Hyp-Gly-Clp-Hyp-Gly-Clp-Hyp-Gly-Met-Hyp-Gly-Clp-Hyp-Gly;

(SEQ ID NO: 259)
Clp-Hyp-Gly-Clp-Hyp-Gly-Clp-Hyp-Gly-Clp-Hyp-Gly-Clp-Hyp-Gly-Clp-Met-Gly-Clp-Hyp-Gly;

(SEQ ID NO: 260)
Clp-Hyp-Gly-Clp-Hyp-Gly-Clp-Hyp-Gly-Clp-Hyp-Gly-Clp-Hyp-Gly-Clp-Hyp-Gly-Met-Hyp-Gly;
and (SEQ ID NO: 261)
Clp-Hyp-Gly-Clp-Hyp-Gly-Clp-Hyp-Gly-Clp-Hyp-Gly-Clp-Hyp-Gly-Clp-Hyp-Gly-Clp-Met-Gly.

In certain other embodiments of the invention, the collagen mimetic peptide may comprise, consist of or have an amino acid sequence that is or corresponds to a 21-mer of any one of SEQ ID NOs:1-9, in which at least one lysine (Lys) residue has been substituted for at least one of the proline residues in SEQ ID NO:1, at least one of the hydroxyproline residues in SEQ ID NOs:2-3 and 6, at least one of the fluoroproline residues in SEQ ID NOs:4-6, or at least one of the chloroproline residues in SEQ ID NOs:7-9, yielding, for example, the following sequences:

```
                                                        (SEQ ID NO: 262)
Pro-Pro-Gly-Pro-Pro-Gly-Lys-Pro-Gly-Pro-Pro-Gly-Pro-Pro-Gly-Pro-
Pro-Gly;

(SEQ ID NO: 263)
Hyp-Pro-Gly-Hyp-Pro-Gly-Lys-Pro-Gly-Hyp-Pro-Gly-Hyp-Pro-Gly-Hyp-Pro-Gly-
Hyp-Pro-Gly;

(SEQ ID NO: 264)
Pro-Hyp-Gly-Pro-Hyp-Gly-Pro-Lys-Gly-Pro-Hyp-Gly-Pro-Hyp-Gly-Pro-Hyp-Gly-
Pro-Hyp-Gly;

(SEQ ID NO: 265)
Pro-Flp-Gly-Pro-Flp-Gly-Pro-Lys-Gly-Pro-Flp-Gly-Pro-Flp-Gly-Pro-Flp-Gly-Pro-
Flp-Gly;

(SEQ ID NO: 266)
Pro-Clp-Gly-Pro-Clp-Gly-Pro-Lys-Gly-Pro-Clp-Gly-Pro-Clp-Gly-Pro-Clp-Gly-Pro-
Clp-Gly;

(SEQ ID NO: 267)
Lys-Pro-Gly-Pro-Pro-Gly-Pro-Pro-Gly-Pro-Pro-Gly-Pro-Pro-Gly-Pro-Pro-Gly-Pro-
Pro-Gly;

(SEQ ID NO: 268)
Pro-Lys-Gly-Pro-Pro-Gly-Pro-Pro-Gly-Pro-Pro-Gly-Pro-Pro-Gly-Pro-Pro-Gly-Pro-
Pro-Gly;

(SEQ ID NO: 269)
Pro-Pro-Gly-Lys-Pro-Gly-Pro-Pro-Gly-Pro-Pro-Gly-Pro-Pro-Gly-Pro-Pro-Gly-Pro-
Pro-Gly;

(SEQ ID NO: 270)
Pro-Pro-Gly-Pro-Lys-Gly-Pro-Pro-Gly-Pro-Pro-Gly-Pro-Pro-Gly-Pro-Pro-Gly-Pro-
Pro-Gly;

(SEQ ID NO: 271)
Pro-Pro-Gly-Pro-Pro-Gly-Pro-Lys-Gly-Pro-Pro-Gly-Pro-Pro-Gly-Pro-Pro-Gly-Pro-
Pro-Gly;

(SEQ ID NO: 272)
Pro-Pro-Gly-Pro-Pro-Gly-Pro-Pro-Gly-Lys-Pro-Gly-Pro-Pro-Gly-Pro-Pro-Gly-Pro-
Pro-Gly;

(SEQ ID NO: 273)
Pro-Pro-Gly-Pro-Pro-Gly-Pro-Pro-Gly-Pro-Lys-Gly-Pro-Pro-Gly-Pro-Pro-Gly-Pro-
Pro-Gly;

(SEQ ID NO: 274)
Pro-Pro-Gly-Pro-Pro-Gly-Pro-Pro-Gly-Pro-Pro-Gly-Lys-Pro-Gly-Pro-Pro-Gly-Pro-
Pro-Gly;

(SEQ ID NO: 275)
Pro-Pro-Gly-Pro-Pro-Gly-Pro-Pro-Gly-Pro-Pro-Gly-Pro-Lys-Gly-Pro-Pro-Gly-Pro-
Pro-Gly;

(SEQ ID NO: 276)
Pro-Pro-Gly-Pro-Pro-Gly-Pro-Pro-Gly-Pro-Pro-Gly-Pro-Pro-Gly-Lys-Pro-Gly-Pro-
Pro-Gly;

(SEQ ID NO: 277)
Pro-Pro-Gly-Pro-Pro-Gly-Pro-Pro-Gly-Pro-Pro-Gly-Pro-Pro-Gly-Pro-Lys-Gly-Pro-
Pro-Gly;
```

-continued (SEQ ID NO: 278)
Pro-Pro-Gly-Pro-Pro-Gly-Pro-Pro-Gly-Pro-Pro-Gly-Pro-Pro-Gly-Pro-Pro-Gly-Lys-Pro-Gly;

(SEQ ID NO: 279)
Pro-Pro-Gly-Pro-Pro-Gly-Pro-Pro-Gly-Pro-Pro-Gly-Pro-Pro-Gly-Pro-Pro-Gly-Pro-Lys-Gly;

(SEQ ID NO: 280)
Lys-Pro-Gly-Hyp-Pro-Gly-Hyp-Pro-Gly-Hyp-Pro-Gly-Hyp-Pro-Gly-Hyp-Pro-Gly-Hyp-Pro-Gly;

(SEQ ID NO: 281)
Hyp-Lys-Gly-Hyp-Pro-Gly-Hyp-Pro-Gly-Hyp-Pro-Gly-Hyp-Pro-Gly-Hyp-Pro-Gly-Hyp-Pro-Gly;

(SEQ ID NO: 282)
Hyp-Pro-Gly-Lys-Pro-Gly-Hyp-Pro-Gly-Hyp-Pro-Gly-Hyp-Pro-Gly-Hyp-Pro-Gly-Hyp-Pro-Gly;

(SEQ ID NO: 283)
Hyp-Pro-Gly-Hyp-Lys-Gly-Hyp-Pro-Gly-Hyp-Pro-Gly-Hyp-Pro-Gly-Hyp-Pro-Gly-Hyp-Pro-Gly;

(SEQ ID NO: 284)
Hyp-Pro-Gly-Hyp-Pro-Gly-Hyp-Lys-Gly-Hyp-Pro-Gly-Hyp-Pro-Gly-Hyp-Pro-Gly-Hyp-Pro-Gly;

(SEQ ID NO: 285)
Hyp-Pro-Gly-Hyp-Pro-Gly-Hyp-Pro-Gly-Lys-Pro-Gly-Hyp-Pro-Gly-Hyp-Pro-Gly-Hyp-Pro-Gly;

(SEQ ID NO: 286)
Hyp-Pro-Gly-Hyp-Pro-Gly-Hyp-Pro-Gly-Hyp-Lys-Gly-Hyp-Pro-Gly-Hyp-Pro-Gly-Hyp-Pro-Gly;

(SEQ ID NO: 287)
Hyp-Pro-Gly-Hyp-Pro-Gly-Hyp-Pro-Gly-Hyp-Pro-Gly-Lys-Pro-Gly-Hyp-Pro-Gly-Hyp-Pro-Gly;

(SEQ ID NO: 288)
Hyp-Pro-Gly-Hyp-Pro-Gly-Hyp-Pro-Gly-Hyp-Pro-Gly-Hyp-Lys-Gly-Hyp-Pro-Gly-Hyp-Pro-Gly;

(SEQ ID NO: 289)
Hyp-Pro-Gly-Hyp-Pro-Gly-Hyp-Pro-Gly-Hyp-Pro-Gly-Hyp-Pro-Gly-Lys-Pro-Gly-Hyp-Pro-Gly;

(SEQ ID NO: 290)
Hyp-Pro-Gly-Hyp-Pro-Gly-Hyp-Pro-Gly-Hyp-Pro-Gly-Hyp-Pro-Gly-Hyp-Lys-Gly-Hyp-Pro-Gly;

(SEQ ID NO: 291)
Hyp-Pro-Gly-Hyp-Pro-Gly-Hyp-Pro-Gly-Hyp-Pro-Gly-Hyp-Pro-Gly-Hyp-Pro-Gly-Lys-Pro-Gly;

(SEQ ID NO: 292)
Hyp-Pro-Gly-Hyp-Pro-Gly-Hyp-Pro-Gly-Hyp-Pro-Gly-Hyp-Pro-Gly-Hyp-Pro-Gly-Hyp-Lys-Gly;

(SEQ ID NO: 293)
Lys-Hyp-Gly-Pro-Hyp-Gly-Pro-Hyp-Gly-Pro-Hyp-Gly-Pro-Hyp-Gly-Pro-Hyp-Gly-Pro-Hyp-Gly;

-continued (SEQ ID NO: 294)
Pro-Lys-Gly-Pro-Hyp-Gly-Pro-Hyp-Gly-Pro-Hyp-Gly-Pro-Hyp-Gly-
Pro-Hyp-Gly;

(SEQ ID NO: 295)
Pro-Hyp-Gly-Lys-Hyp-Gly-Pro-Hyp-Gly-Pro-Hyp-Gly-Pro-Hyp-Gly-
Pro-Hyp-Gly;

(SEQ ID NO: 296)
Pro-Hyp-Gly-Pro-Lys-Gly-Pro-Hyp-Gly-Pro-Hyp-Gly-Pro-Hyp-Gly-
Pro-Hyp-Gly;

(SEQ ID NO: 297)
Pro-Hyp-Gly-Pro-Hyp-Gly-Lys-Hyp-Gly-Pro-Hyp-Gly-Pro-Hyp-Gly-
Pro-Hyp-Gly;

(SEQ ID NO: 298)
Pro-Hyp-Gly-Pro-Hyp-Gly-Pro-Hyp-Gly-Lys-Hyp-Gly-Pro-Hyp-Gly-
Pro-Hyp-Gly;

(SEQ ID NO: 299)
Pro-Hyp-Gly-Pro-Hyp-Gly-Pro-Hyp-Gly-Pro-Lys-Gly-Pro-Hyp-Gly-
Pro-Hyp-Gly;

(SEQ ID NO: 300)
Pro-Hyp-Gly-Pro-Hyp-Gly-Pro-Hyp-Gly-Pro-Hyp-Gly-Lys-Hyp-Gly-
Pro-Hyp-Gly;

(SEQ ID NO: 301)
Pro-Hyp-Gly-Pro-Hyp-Gly-Pro-Hyp-Gly-Pro-Hyp-Gly-Pro-Lys-Gly-Pro-Hyp-Gly-
Pro-Hyp-Gly;

(SEQ ID NO: 302)
Pro-Hyp-Gly-Pro-Hyp-Gly-Pro-Hyp-Gly-Pro-Hyp-Gly-Pro-Hyp-Gly-Lys-Hyp-Gly-
Pro-Hyp-Gly;

(SEQ ID NO: 303)
Pro-Hyp-Gly-Pro-Hyp-Gly-Pro-Hyp-Gly-Pro-Hyp-Gly-Pro-Hyp-Gly-Pro-Lys-Gly-
Pro-Hyp-Gly;

(SEQ ID NO: 304)
Pro-Hyp-Gly-Pro-Hyp-Gly-Pro-Hyp-Gly-Pro-Hyp-Gly-Pro-Hyp-Gly-Pro-Hyp-Gly-
Lys-Hyp-Gly;

(SEQ ID NO: 305)
Pro-Hyp-Gly-Pro-Hyp-Gly-Pro-Hyp-Gly-Pro-Hyp-Gly-Pro-Hyp-Gly-Pro-Hyp-Gly-
Pro-Lys-Gly;

(SEQ ID NO: 306)
Lys-Flp-Gly-Pro-Flp-Gly-Pro-Flp-Gly-Pro-Flp-Gly-Pro-Flp-Gly-Pro-Flp-Gly-Pro-
Flp-Gly;

(SEQ ID NO: 307)
Pro-Lys-Gly-Pro-Flp-Gly-Pro-Flp-Gly-Pro-Flp-Gly-Pro-Flp-Gly-Pro-Flp-Gly-Pro-
Flp-Gly;

(SEQ ID NO: 308)
Pro-Flp-Gly-Lys-Flp-Gly-Pro-Flp-Gly-Pro-Flp-Gly-Pro-Flp-Gly-Pro-Flp-Gly-Pro-
Flp-Gly;

(SEQ ID NO: 309)
Pro-Flp-Gly-Pro-Lys-Gly-Pro-Flp-Gly-Pro-Flp-Gly-Pro-Flp-Gly-Pro-Flp-Gly-Pro-
Flp-Gly;

-continued (SEQ ID NO: 310)
Pro-Flp-Gly-Pro-Flp-Gly-Lys-Flp-Gly-Pro-Flp-Gly-Pro-Flp-Gly-Pro-Flp-Gly;

(SEQ ID NO: 311)
Pro-Flp-Gly-Pro-Flp-Gly-Pro-Flp-Gly-Lys-Flp-Gly-Pro-Flp-Gly-Pro-Flp-Gly;

(SEQ ID NO: 312)
Pro-Flp-Gly-Pro-Flp-Gly-Pro-Flp-Gly-Pro-Lys-Gly-Pro-Flp-Gly-Pro-Flp-Gly;

(SEQ ID NO: 313)
Pro-Flp-Gly-Pro-Flp-Gly-Pro-Flp-Gly-Pro-Flp-Gly-Lys-Flp-Gly-Pro-Flp-Gly;

(SEQ ID NO: 314)
Pro-Flp-Gly-Pro-Flp-Gly-Pro-Flp-Gly-Pro-Flp-Gly-Pro-Lys-Gly-Pro-Flp-Gly;

(SEQ ID NO: 315)
Pro-Flp-Gly-Pro-Flp-Gly-Pro-Flp-Gly-Pro-Flp-Gly-Pro-Flp-Gly-Lys-Flp-Gly-Pro-Flp-Gly;

(SEQ ID NO: 316)
Pro-Flp-Gly-Pro-Flp-Gly-Pro-Flp-Gly-Pro-Flp-Gly-Pro-Flp-Gly-Pro-Lys-Gly-Pro-Flp-Gly;

(SEQ ID NO: 317)
Pro-Flp-Gly-Pro-Flp-Gly-Pro-Flp-Gly-Pro-Flp-Gly-Pro-Flp-Gly-Pro-Flp-Gly-Lys-Flp-Gly;

(SEQ ID NO: 318)
Pro-Flp-Gly-Pro-Flp-Gly-Pro-Flp-Gly-Pro-Flp-Gly-Pro-Flp-Gly-Pro-Flp-Gly-Pro-Lys-Gly;

(SEQ ID NO: 319)
Lys-Flp-Gly-Pro-Flp-Gly-Pro-Flp-Gly-Pro-Flp-Gly-Pro-Flp-Gly-Pro-Flp-Gly-Pro-Flp-Gly;

(SEQ ID NO: 320)
Pro-Lys-Gly-Pro-Flp-Gly-Pro-Flp-Gly-Pro-Flp-Gly-Pro-Flp-Gly-Pro-Flp-Gly-Pro-Flp-Gly;

(SEQ ID NO: 321)
Pro-Flp-Gly-Lys-Flp-Gly-Pro-Flp-Gly-Pro-Flp-Gly-Pro-Flp-Gly-Pro-Flp-Gly-Pro-Flp-Gly;

(SEQ ID NO: 322)
Pro-Flp-Gly-Pro-Lys-Gly-Pro-Flp-Gly-Pro-Flp-Gly-Pro-Flp-Gly-Pro-Flp-Gly-Pro-Flp-Gly;

(SEQ ID NO: 323)
Pro-Flp-Gly-Pro-Flp-Gly-Lys-Flp-Gly-Pro-Flp-Gly-Pro-Flp-Gly-Pro-Flp-Gly-Pro-Flp-Gly;

(SEQ ID NO: 324)
Pro-Flp-Gly-Pro-Flp-Gly-Pro-Lys-Gly-Pro-Flp-Gly-Pro-Flp-Gly-Pro-Flp-Gly-Pro-Flp-Gly;

(SEQ ID NO: 325)
Pro-Flp-Gly-Pro-Flp-Gly-Pro-Flp-Gly-Lys-Flp-Gly-Pro-Flp-Gly-Pro-Flp-Gly-Pro-Flp-Gly;

-continued (SEQ ID NO: 326)
Pro-Flp-Gly-Pro-Flp-Gly-Pro-Flp-Gly-Pro-Lys-Gly-Pro-Flp-Gly-Pro-Flp-Gly-Pro-Flp-Gly;

(SEQ ID NO: 327)
Pro-Flp-Gly-Pro-Flp-Gly-Pro-Flp-Gly-Pro-Flp-Gly-Lys-Flp-Gly-Pro-Flp-Gly-Pro-Flp-Gly;

(SEQ ID NO: 328)
Pro-Flp-Gly-Pro-Flp-Gly-Pro-Flp-Gly-Pro-Flp-Gly-Pro-Lys-Gly-Pro-Flp-Gly-Pro-Flp-Gly;

(SEQ ID NO: 329)
Pro-Flp-Gly-Pro-Flp-Gly-Pro-Flp-Gly-Pro-Flp-Gly-Pro-Flp-Gly-Lys-Flp-Gly-Pro-Flp-Gly;

(SEQ ID NO: 330)
Pro-Flp-Gly-Pro-Flp-Gly-Pro-Flp-Gly-Pro-Flp-Gly-Pro-Flp-Gly-Pro-Lys-Gly-Pro-Flp-Gly;

(SEQ ID NO: 331)
Pro-Flp-Gly-Pro-Flp-Gly-Pro-Flp-Gly-Pro-Flp-Gly-Pro-Flp-Gly-Pro-Flp-Gly-Lys-Flp-Gly;

(SEQ ID NO: 332)
Pro-Flp-Gly-Pro-Flp-Gly-Pro-Flp-Gly-Pro-Flp-Gly-Pro-Flp-Gly-Pro-Flp-Gly-Pro-Lys-Gly;

(SEQ ID NO: 333)
Lys-Hyp-Gly-Flp-Hyp-Gly-Flp-Hyp-Gly-Flp-Hyp-Gly-Flp-Hyp-Gly-Flp-Hyp-Gly-Flp-Hyp-Gly;

(SEQ ID NO: 334)
Flp-Lys-Gly-Flp-Hyp-Gly-Flp-Hyp-Gly-Flp-Hyp-Gly-Flp-Hyp-Gly-Flp-Hyp-Gly-Flp-Hyp-Gly;

(SEQ ID NO: 335)
Flp-Hyp-Gly-Lys-Hyp-Gly-Flp-Hyp-Gly-Flp-Hyp-Gly-Flp-Hyp-Gly-Flp-Hyp-Gly-Flp-Hyp-Gly;

(SEQ ID NO: 336)
Flp-Hyp-Gly-Flp-Lys-Gly-Flp-Hyp-Gly-Flp-Hyp-Gly-Flp-Hyp-Gly-Flp-Hyp-Gly-Flp-Hyp-Gly;

(SEQ ID NO: 337)
Flp-Hyp-Gly-Flp-Hyp-Gly-Lys-Hyp-Gly-Flp-Hyp-Gly-Flp-Hyp-Gly-Flp-Hyp-Gly-Flp-Hyp-Gly;

(SEQ ID NO: 338)
Flp-Hyp-Gly-Flp-Hyp-Gly-Flp-Lys-Gly-Flp-Hyp-Gly-Flp-Hyp-Gly-Flp-Hyp-Gly-Flp-Hyp-Gly;

(SEQ ID NO: 339)
Flp-Hyp-Gly-Flp-Hyp-Gly-Flp-Hyp-Gly-Lys-Hyp-Gly-Flp-Hyp-Gly-Flp-Hyp-Gly-Flp-Hyp-Gly;

(SEQ ID NO: 340)
Flp-Hyp-Gly-Flp-Hyp-Gly-Flp-Hyp-Gly-Flp-Lys-Gly-Flp-Hyp-Gly-Flp-Hyp-Gly-Flp-Hyp-Gly;

(SEQ ID NO: 341)
Flp-Hyp-Gly-Flp-Hyp-Gly-Flp-Hyp-Gly-Flp-Hyp-Gly-Lys-Hyp-Gly-Flp-Hyp-Gly-Flp-Hyp-Gly;

(SEQ ID NO: 342)
Flp-Hyp-Gly-Flp-Hyp-Gly-Flp-Hyp-Gly-Flp-Hyp-Gly-Flp-Lys-Gly-Flp-Hyp-Gly-Flp-Hyp-Gly;

(SEQ ID NO: 343)
Flp-Hyp-Gly-Flp-Hyp-Gly-Flp-Hyp-Gly-Flp-Hyp-Gly-Flp-Hyp-Gly-Lys-Hyp-Gly-Flp-Hyp-Gly;

(SEQ ID NO: 344)
Flp-Hyp-Gly-Flp-Hyp-Gly-Flp-Hyp-Gly-Flp-Hyp-Gly-Flp-Hyp-Gly-Flp-Lys-Gly-Flp-Hyp-Gly;

(SEQ ID NO: 345)
Flp-Hyp-Gly-Flp-Hyp-Gly-Flp-Hyp-Gly-Flp-Hyp-Gly-Flp-Hyp-Gly-Flp-Hyp-Gly-Lys-Hyp-Gly;

(SEQ ID NO: 346)
Flp-Hyp-Gly-Flp-Hyp-Gly-Flp-Hyp-Gly-Flp-Hyp-Gly-Flp-Hyp-Gly-Flp-Hyp-Gly-Flp-Lys-Gly;

(SEQ ID NO: 347)
Lys-Clp-Gly-Pro-Clp-Gly-Pro-Clp-Gly-Pro-Clp-Gly-Pro-Clp-Gly-Pro-Clp-Gly-Pro-Clp-Gly;

(SEQ ID NO: 348)
Pro-Lys-Gly-Pro-Clp-Gly-Pro-Clp-Gly-Pro-Clp-Gly-Pro-Clp-Gly-Pro-Clp-Gly-Pro-Clp-Gly;

(SEQ ID NO: 349)
Pro-Clp-Gly-Lys-Clp-Gly-Pro-Clp-Gly-Pro-Clp-Gly-Pro-Clp-Gly-Pro-Clp-Gly-Pro-Clp-Gly;

(SEQ ID NO: 350)
Pro-Clp-Gly-Pro-Lys-Gly-Pro-Clp-Gly-Pro-Clp-Gly-Pro-Clp-Gly-Pro-Clp-Gly-Pro-Clp-Gly;

(SEQ ID NO: 351)
Pro-Clp-Gly-Pro-Clp-Gly-Lys-Clp-Gly-Pro-Clp-Gly-Pro-Clp-Gly-Pro-Clp-Gly-Pro-Clp-Gly;

(SEQ ID NO: 352)
Pro-Clp-Gly-Pro-Clp-Gly-Pro-Clp-Gly-Lys-Clp-Gly-Pro-Clp-Gly-Pro-Clp-Gly-Pro-Clp-Gly;

(SEQ ID NO: 353)
Pro-Clp-Gly-Pro-Clp-Gly-Pro-Clp-Gly-Pro-Lys-Gly-Pro-Clp-Gly-Pro-Clp-Gly-Pro-Clp-Gly;

(SEQ ID NO: 354)
Pro-Clp-Gly-Pro-Clp-Gly-Pro-Clp-Gly-Pro-Clp-Gly-Lys-Clp-Gly-Pro-Clp-Gly-Pro-Clp-Gly;

(SEQ ID NO: 355)
Pro-Clp-Gly-Pro-Clp-Gly-Pro-Clp-Gly-Pro-Clp-Gly-Pro-Lys-Gly-Pro-Clp-Gly-Pro-Clp-Gly;

(SEQ ID NO: 356)
Pro-Clp-Gly-Pro-Clp-Gly-Pro-Clp-Gly-Pro-Clp-Gly-Pro-Clp-Gly-Lys-Clp-Gly-Pro-Clp-Gly;

(SEQ ID NO: 357)
Pro-Clp-Gly-Pro-Clp-Gly-Pro-Clp-Gly-Pro-Clp-Gly-Pro-Clp-Gly-Pro-Clp-Gly-Lys-Gly-Pro-Clp-Gly;

```
                                                        (SEQ ID NO: 358)
Pro-Clp-Gly-Pro-Clp-Gly-Pro-Clp-Gly-Pro-Clp-Gly-Pro-Clp-Gly-Lys-
Clp-Gly;

(SEQ ID NO: 359)
Pro-Clp-Gly-Pro-Clp-Gly-Pro-Clp-Gly-Pro-Clp-Gly-Pro-Clp-Gly-Pro-
Lys-Gly;

(SEQ ID NO: 360)
Lys-Clp-Gly-Pro-Clp-Gly-Pro-Clp-Gly-Pro-Clp-Gly-Pro-Clp-Gly-Pro-
Clp-Gly;

(SEQ ID NO: 361)
Pro-Lys-Gly-Pro-Clp-Gly-Pro-Clp-Gly-Pro-Clp-Gly-Pro-Clp-Gly-Pro-
Clp-Gly;

(SEQ ID NO: 362)
Pro-Clp-Gly-Lys-Clp-Gly-Pro-Clp-Gly-Pro-Clp-Gly-Pro-Clp-Gly-Pro-
Clp-Gly;

(SEQ ID NO: 363)
Pro-Clp-Gly-Pro-Lys-Gly-Pro-Clp-Gly-Pro-Clp-Gly-Pro-Clp-Gly-Pro-
Clp-Gly;

(SEQ ID NO: 364)
Pro-Clp-Gly-Pro-Clp-Gly-Lys-Clp-Gly-Pro-Clp-Gly-Pro-Clp-Gly-Pro-
Clp-Gly;

(SEQ ID NO: 365)
Pro-Clp-Gly-Pro-Clp-Gly-Pro-Lys-Gly-Pro-Clp-Gly-Pro-Clp-Gly-Pro-
Clp-Gly;

(SEQ ID NO: 366)
Pro-Clp-Gly-Pro-Clp-Gly-Pro-Clp-Gly-Lys-Clp-Gly-Pro-Clp-Gly-Pro-
Clp-Gly;

(SEQ ID NO: 367)
Pro-Clp-Gly-Pro-Clp-Gly-Pro-Clp-Gly-Pro-Lys-Gly-Pro-Clp-Gly-Pro-
Clp-Gly;

(SEQ ID NO: 368)
Pro-Clp-Gly-Pro-Clp-Gly-Pro-Clp-Gly-Pro-Clp-Gly-Lys-Clp-Gly-Pro-
Clp-Gly;

(SEQ ID NO: 369)
Pro-Clp-Gly-Pro-Clp-Gly-Pro-Clp-Gly-Pro-Clp-Gly-Pro-Lys-Gly-Pro-
Clp-Gly;

(SEQ ID NO: 370)
Pro-Clp-Gly-Pro-Clp-Gly-Pro-Clp-Gly-Pro-Clp-Gly-Pro-Clp-Gly-Lys-Clp-Gly-Pro-
Clp-Gly;

(SEQ ID NO: 371)
Pro-Clp-Gly-Pro-Clp-Gly-Pro-Clp-Gly-Pro-Clp-Gly-Pro-Clp-Gly-Pro-Lys-Gly-Pro-
Clp-Gly;

(SEQ ID NO: 372)
Pro-Clp-Gly-Pro-Clp-Gly-Pro-Clp-Gly-Pro-Clp-Gly-Pro-Clp-Gly-Pro-Clp-Gly-Lys-
Clp-Gly;

(SEQ ID NO: 373)
Pro-Clp-Gly-Pro-Clp-Gly-Pro-Clp-Gly-Pro-Clp-Gly-Pro-Clp-Gly-Pro-Clp-Gly-Pro-
Lys-Gly;
```

-continued

```
                                                           (SEQ ID NO: 374)
Lys-Hyp-Gly-Clp-Hyp-Gly-Clp-Hyp-Gly-Clp-Hyp-Gly-Clp-Hyp-Gly-

Clp-Hyp-Gly;

(SEQ ID NO: 375)
Clp-Lys-Gly-Clp-Hyp-Gly-Clp-Hyp-Gly-Clp-Hyp-Gly-Clp-Hyp-Gly-

Clp-Hyp-Gly;

(SEQ ID NO: 376)
Clp-Hyp-Gly-Lys-Hyp-Gly-Clp-Hyp-Gly-Clp-Hyp-Gly-Clp-Hyp-Gly-

Clp-Hyp-Gly;

(SEQ ID NO: 377)
Clp-Hyp-Gly-Clp-Lys-Gly-Clp-Hyp-Gly-Clp-Hyp-Gly-Clp-Hyp-Gly-

Clp-Hyp-Gly;

(SEQ ID NO: 378)
Clp-Hyp-Gly-Clp-Hyp-Gly-Lys-Hyp-Gly-Clp-Hyp-Gly-Clp-Hyp-Gly-

Clp-Hyp-Gly;

(SEQ ID NO: 379)
Clp-Hyp-Gly-Clp-Hyp-Gly-Clp-Lys-Gly-Clp-Hyp-Gly-Clp-Hyp-Gly-

Clp-Hyp-Gly;

(SEQ ID NO: 380)
Clp-Hyp-Gly-Clp-Hyp-Gly-Clp-Hyp-Gly-Lys-Hyp-Gly-Clp-Hyp-Gly-

Clp-Hyp-Gly;

(SEQ ID NO: 381)
Clp-Hyp-Gly-Clp-Hyp-Gly-Clp-Hyp-Gly-Clp-Lys-Gly-Clp-Hyp-Gly-

Clp-Hyp-Gly;

(SEQ ID NO: 382)
Clp-Hyp-Gly-Clp-Hyp-Gly-Clp-Hyp-Gly-Clp-Hyp-Gly-Lys-Hyp-Gly-

Clp-Hyp-Gly;

(SEQ ID NO: 383)
Clp-Hyp-Gly-Clp-Hyp-Gly-Clp-Hyp-Gly-Clp-Hyp-Gly-Clp-Lys-Gly-

Clp-Hyp-Gly;

(SEQ ID NO: 384)
Clp-Hyp-Gly-Clp-Hyp-Gly-Clp-Hyp-Gly-Clp-Hyp-Gly-Clp-Hyp-Gly-Lys-Hyp-Gly-

Clp-Hyp-Gly;

(SEQ ID NO: 385)
Clp-Hyp-Gly-Clp-Hyp-Gly-Clp-Hyp-Gly-Clp-Hyp-Gly-Clp-Hyp-Gly-Clp-Lys-Gly-

Clp-Hyp-Gly;

(SEQ ID NO: 386)
Clp-Hyp-Gly-Clp-Hyp-Gly-Clp-Hyp-Gly-Clp-Hyp-Gly-Clp-Hyp-Gly-Clp-Hyp-Gly-

Lys-Hyp-Gly;
and (SEQ ID NO: 387)
Clp-Hyp-Gly-Clp-Hyp-Gly-Clp-Hyp-Gly-Clp-Hyp-Gly-Clp-Hyp-Gly-Clp-Hyp-Gly- Clp-Lys-Gly.
```

Another suitable CMP for use according to the invention is a CMP having or comprising the sequence Hyp-Flp-Gly-Hyp-Flp-Gly-Hyp-Flp-Gly-Hyp-Flp-Gly-Hyp-Flp-Gly-Flp-Gly-Hyp-Flp-Gly (SEQ ID NO:388).

Other suitable CMPs for use according to the invention is a CMP having or comprising the sequence $Gly_3$-(Pro-Hyp-Gly)$_6$ (SEQ ID NO:417), $Gly_3$-(Pro-Flp-Gly)$_6$ (SEQ ID NO:418), $Gly_3$-(Pro-Hyp-Gly)$_7$ (SEQ ID NO:399), $Gly_3$-(Pro-Flp-Gly)$_7$ (SEQ ID NO:400), $Gly_3$-(Pro-Hyp-Gly) (SEQ ID NO:401), $Gly_3$-(Pro-Flp-Gly)$_8$ (SEQ ID NO:402), $Gly_3$-(Pro-Hyp-Gly)$_9$ (SEQ ID NO:403), $Gly_3$-(Pro-Flp-Gly)$_9$ (SEQ ID NO:404), (Pro-Hyp-Gly)$_6$-Tyr (SEQ ID NO:405), (Pro-Flp-Gly)$_6$-Tyr (SEQ ID NO:406), (Pro-Hyp-Gly)$_7$-Tyr (SEQ ID NO:407), (Pro-Flp-Gly)$_7$-Tyr (SEQ ID NO:408), (Pro-Hyp-Gly)$_8$-Tyr (SEQ ID NO:409), (Pro-Flp-Gly)$_8$-Tyr (SEQ ID NO:410), Cys-(Pro-Hyp-Gly)$_3$ (SEQ ID NO:411), Cys-(Pro-Flp-Gly)$_3$ (SEQ ID NO:412), Cys-(Pro-Hyp-Gly)$_5$ (SEQ ID NO:413), Cys-(Pro-Flp-Gly)$_5$ (SEQ ID NO:414), Cys-(Pro-Hyp-Gly)$_7$ (SEQ ID NO:415), and Cys-(Pro-Flp-Gly)$_7$ (SEQ ID NO:416), and other analogous CMPs which may be suitable for use as agents for modification of collagen in vitro and in vivo for use in therapeutic and/or diagnostic methods (see, e.g., U.S. Pat. Nos. 8,283,414 and 8,883,964, which are incorporated herein by reference in their entireties).

Preferred CMPs according to this aspect of the invention include CMPs having amino acid sequences corresponding to SEQ ID NOs:1-14, 66-94, 107-135, 136-140, 192-220, 233-261, 260-264, 280, 281, 293, 294, 306, 307, 318-346, 347, 348, 359-388 and 399-418. Particularly preferred are CMPs having amino acid sequences corresponding to SEQ ID NOs:1, 2, 4, 5, 6, 9, 10-27, 81-94, 122-135, 207-220, 248-261, 333-346, 374-388 and 399-418. Even more particularly preferred are CMPs having amino acid sequences corresponding to SEQ ID NOs:1, 2, 4, 5, 6, 9, 388 and 397-416 (for CMPs that are not to be directly conjugated to one or more pharmaceutically active ingredients or biologics nor one or more diagnostic labels or agents), and CMPs having amino acid sequences corresponding to SEQ ID NOs: 10-27, 81-94, 122-135, 207-220, 248-261, 333-346, 374-388 and 399-418 (for CMPs that are to be directly conjugated to one or more pharmaceutically active ingredients or biologics or one or more diagnostic labels or agents). It will be understood by those of ordinary skill, of course, based on knowledge in the art and the teachings herein, that such CMPs may comprise two or more cysteine, methionine and/or lysine residues, in which at least one additional cysteine, methionine and/or lysine residue, or any combination thereof, may be substituted for at least one proline residue, at least one hydroxyproline residue, at least one fluoroproline residue and/or at least one chloroproline residue in any of the foregoing CMP sequences that comprise at least one proline, at least one hydroxyproline, at least one fluoroproline and/or at least one chloroproline residue. It also will be appreciated by those of ordinary skill in the art based on the teachings herein and information readily available in the art that other combinations of amino acid substitutions are also possible and within the scope of the present invention.

The CMPs described herein are suitable for a variety of purposes. For example, as described in further detail elsewhere herein, the CMPs may be used in a variety of therapeutic applications or preventative applications by being directly applied to or introduced into the body of a human or veterinary animal, particularly at sites of collagen disruption or potential collagen disruption, where the CMPs described herein will localize directly to the site of collagen disruption, anneal to disrupted collagen strands and stabilize the collagen structure such that it resists further disruption, and in some cases reform a native collagen triple helix in the site of collagen disruption. Such applications are useful in promoting the repair and strengthening of disrupted collagen in sites of injury or potential injury or disruption, for example in wounds, diseases, structural abnormalities or disorders (e.g., scarring, wrinkle formation, etc.) involving skin, tendon, ligament, cartilage, bone and other collagen-containing structures and organs. The CMPs described herein also are useful in providing biocompatible coatings for certain medical devices, to promote the healing of injuries and disorders in areas of the body where such devices are used in treating or preventing certain diseases, disorders and structural abnormalities or injuries in humans and veterinary animals, particularly those in which such diseases, disorders and structural abnormalities or injuries involve disruption of collagen and/or collagen-containing structures. The CMPs described herein also are useful in providing a unique delivery vehicle suitable for delivering a variety of therapeutic compounds, compositions and medicaments to sites of disease, disorder and structural abnormality or injury in humans and veterinary animals, particularly for use in treating, preventing or ameliorating diseases, disorders, medical conditions and structural abnormalities or injuries in which collagen disruption is either the cause of, is associated with, or is colocalized with the site of the disease, disorder and structural abnormality or injury. In additional embodiments, the CMPs described herein are useful in providing diagnostic agents suitable for diagnosing or detecting a disease, disorder, structural abnormality or injury in humans and veterinary animals. In certain such aspects, the CMPs may be either co-formulated with or conjugated directly or indirectly to one or more suitable diagnostic compounds, agents, labels and the like (see, e.g., U.S. Pat. Nos. 8,283,414 and 8,883,964, the disclosures of which are incorporated herein by reference in their entireties). Other suitable uses of the CMPs described herein and used in certain aspects of the present invention will be readily apparent to the ordinarily skilled artisan based on the disclosure herein and information that is readily available in the art.

In certain embodiments, the CMPs described herein are suitable for formation into a film, wafer, membrane or gel comprising one or more of the CMPs in a form suitable for introduction or implantation into a human or animal for therapeutic, preventative or diagnostic applications such as those described herein and others that will be familiar to those of ordinary skill in the relevant arts. For example, films, wafers, membranes, spheres, nanoparticles or gels can be formed from a solution of one or more of the CMPs described herein using methods such as those described in U.S. Pat. Nos. 6,197,934; 6,448,378; and 9,289,396; the disclosures of all of which are incorporated herein by reference in their entireties. Alternatively, films, wafers, membranes spheres, nanoparticles, or gels can be formed from other materials, such as atelocollagen (see U.S. Pat. Nos. 6,197,934; 6,448,378; and 9,289,396), copolymers of poly(lactic acid) and poly(glycoloic acid) (PLGA) (see Bala, I., et al., Crit. Rev. Ther. Drug Carrier Syst. 21(5):387-422 (2004)), and other materials that are known to those of ordinary skill in the art (see, e.g., Kumar, V., et al., eds., "Polymer Gels: Perspectives and Applications", ISBN 978-981-10-6079-3, Singapore: Springer (2018)), and one or more of the CMPs can be suitably incorporated into such films, wafers, membranes, spheres, nanoparticles, gels, etc., during the formation thereof by including the CMPs in the solution, at concentrations of about 1%-99%, about 2%-95%, about 3%-90%, about 4%-90%, about 5%-90%, about 10%-90%, about 15%-90%, about 20%-90%, about 25%-90%, about 25%-85%, about 25%-75%, about 25%-50%, about 35%-50%, and the like. Suitable other amounts or concentrations of the CMPs described herein that can be suitably included in the solutions during formation of the films, wafers, membranes, spheres, nanoparticles, gels, etc., will be readily apparent from the teachings herein and from information readily available in the art to the ordinarily skilled artisan. In certain such embodiments, one or more therapeutic compounds described herein, and/or one or more CMP-TC conjugates described herein, can be suitably incorporated into the solution from which the films, wafers, membranes, spheres, nanoparticles, gels, etc., are formed. Alternatively, in related aspects, one or more films, wafers, membranes, spheres, nanoparticles, gels, etc., once formed as described above, can be treated or coated with one or more CMPs and/or CMP-TC conjugates described herein, by immersing the films, wafers, membranes, spheres, nanoparticles, gels, etc., in a solution, particularly a buffered aqueous solution, containing a suitable amount or concentration (such as those described herein) of one or more CMPs or CMP-TC conjugates described herein, and then drying the films, wafers, membranes, etc., prior to use in therapeutic, preventative or diagnostic methods such as those described herein.

Attachment/Conjugation of CMPs

In certain embodiments of the invention, the CMPs described herein are suitably attached or conjugated to one or more therapeutic or diagnostic compounds, to produce CMP conjugate compounds. In such embodiments of the invention, the CMP-therapeutic compound or CMP-diagnostic compound conjugate compounds can then be introduced into the body of a human or veterinary animal, in methods of treating and/or preventing and/or diagnosing certain diseases, disorders and structural abnormalities in humans or veterinary animals suffering therefrom. Accordingly, in certain embodiments the present invention also provides the use of the CMPs described herein attached or conjugated to one or more therapeutic compounds to produce conjugated CMPs, compositions comprising such conjugated CMPs (which may optionally comprise one or more additional therapeutic or pharmaceutically active ingredients), methods of producing such conjugates and methods of using such conjugates and compositions in the treatment, prevention and diagnosis of a variety of diseases, disorders and medical conditions in humans and veterinary animals.

Conjugates of CMPs and at least one therapeutic compound (which may be described herein as "CMP-TC conjugates") according to this aspect of the invention will comprise at least one CMP described herein attached to at least one therapeutic compound to form a CMP-TC conjugate. CMPs suitably used in such aspects of the invention include any of those described herein, including CMPs having an amino acid sequence corresponding to any one of SEQ ID NOs:1-387 and particularly wherein the CMPs have an amino acid sequence corresponding to anyone of SEQ IDNOs:1-14, 66-94, 107-135, 136-140, 192-220, 233-261, 260-264, 280, 281, 293, 294, 306, 307, 318-346, 347, 348, 359-388, and 399-418, and more particularly CMPs having amino acid sequences corresponding to SEQ ID NOs:10-27, 81-94, 122-135, 207-220, 248-261, 333-346, 374-388 and 399-418. Other suitable CMP sequences will be immediately apparent to one of ordinary skill in the art based on the teachings contained herein. For example, a CMP having at least one, and in some cases more than one, cysteine, methionine or lysine residue substituted in place of at least one, and in some cases more than one, proline, hydroxyproline, fluoroproline or chloroproline residue in SEQ ID NOs:1-9, will be particularly suitable for use in producing the CMP-TC conjugates provided by and used in the present invention. Examples of such suitable CMPs include those having amino acid sequences corresponding to SEQ ID NOs: 10-27, 81-94, 122-135, 207-220, 248-261, 333-346, 374-388 and 399-418.

Methods of preparing the CMPs and CMP-TCs described herein and provided and used in the present invention will be familiar to those of ordinary skill in the art based on the teachings herein and information that is readily available in the art. For example, CMPs can be synthesized using standard protein/peptide synthesis techniques such as those described in U.S. Pat. Nos. 5,973,112; 7,122,521; and 7,858,741; as well as in U.S. Patent Publ. No. US 2007/0275897 A1, the disclosures of all of which are incorporated herein by reference in their entireties. Synthesis of CMPs can also be accomplished by purchasing custom-synthesized CMPs produced commercially, for example by Bachem (Torrance, Calif., USA) and RS Synthesis (Louisville, Ky., USA). In other embodiments, synthesis of CMPs can be accomplished using genetic engineering and recombinant expression of the CMPs from prokaryotic or eukaryotic expression systems (see, e.g., Buechter, D. D., et al., J. Biol. Chem. 278(1):645-650 (2003)).

In synthesizing the peptides described herein, in certain embodiments it is preferred that certain stereochemistries be used for the amino acid substitutions, particularly if hydroxyproline, fluoroproline or chloroproline are used:

(1) if hydroxyproline is substituted in place of proline in the Xaa position of the Xaa-Yaa-Gly trimer noted hereinabove, in certain embodiments the hydroxyproline has a (2R, 4S) stereochemistry, or a cis or trans, and preferably a cis, stereochemistry;

(2) if hydroxyproline is substituted in place of proline in the Yaa position of the Xaa-Yaa-Gly trimer noted hereinabove, in certain embodiments the hydroxyproline has a (2R, 4S) stereochemistry, or a cis or trans, and preferably a cis, stereochemistry;

(3) if fluoroproline is substituted in place of proline in the Yaa position of the Xaa-Yaa-Gly trimer noted hereinabove, in certain embodiments the hydroxyproline has a (2R, 4S) stereochemistry, or a cis or trans, and preferably a cis, stereochemistry; and (4) if chloroproline is substituted in place of proline in the Yaa position of the Xaa-Yaa-Gly trimer noted hereinabove, in certain embodiments the hydroxyproline has a (2R, 4S) stereochemistry, or a cis or trans, and preferably a cis, stereochemistry.

Other suitable stereochemistries can be determined empirically without having to resort to undue experimentation, and will be immediately apparent to those of ordinary skill in the art. As noted above, certain CMPs provided by and used in the present invention may contain one or more additional substitutions, for example one or more cysteine residues and/or one or more methionine residues, in place of one or more prolines in a given CMP multimer. Such substitutions are suitably accomplished by adding those residues to the growing CMP peptide chain during the synthetic process using standard peptide synthetic methods such as those described elsewhere herein and those that are known in the art.

Once the CMPs have been prepared, they are suitably used in producing the CMP-TCs of the invention, i.e., the therapeutic or diagnostic compositions of the invention, by attaching one or more therapeutic compounds to the CMPs. In certain embodiments, the CMP-TCs of the invention can be prepared a method comprising (a) providing a collagen mimetic peptide having an amino acid sequence corresponding to any one of SEQ ID NOs:1-387, particularly CMPs have an amino acid sequence corresponding to any one of SEQ ID NOs:1-14, 66-94, 107-135, 136-140, 192-220, 233-261, 260-264, 280, 281, 293, 294, 306, 307, 318-346, 347, 348, 359-388 and 399-418, and more particularly CMPs having amino acid sequences corresponding to SEQ ID NOs:10-27, 81-94, 122-135, 207-220, 248-261, 333-346, 374-388 and 399-418; (b) providing at least one therapeutic or diagnostic compound suitable to be conjugated to the CMP; and (c) attaching the therapeutic or diagnostic compound directly or indirectly to the CMP. In certain cases, particularly wherein the therapeutic compound is a small peptide biologic compound, the therapeutic compound can be directly attached to the CMP via a peptide bond, for example by simply extending the synthesis of the peptide beyond the carboxy terminus of the CMP and attaching the amino terminal amino acid of the therapeutic compound to the carboxy terminal amino acid of the CMP via a peptide bond. One example of such a CMP-TC is a peptide conjugate in which the wound healing peptide known as Substance P and having an amino acid sequence of Arg-Pro-Lys-Pro-Gln-Gln-Phe-Phe-Gly-Leu-Met (SEQ ID NO:389), is attached to a CMP described herein. Examples of such conjugates include, for example:

(SEQ ID NO: 390)
Pro-Pro-Gly-Pro-Pro-Gly-Pro-Pro-Gly-Pro-Pro-Gly-

Pro-Pro-Gly-Pro-Pro-Gly-Pro-Pro-Gly-Arg-Pro-Lys-

Pro-Gln-Gln-Phe-Phe-Gly-Leu-Met;

(SEQ ID NO: 391)
Hyp-Pro-Gly-Hyp-Pro-Gly-Hyp-Pro-Gly-Hyp-Pro-Gly-

Hyp-Pro-Gly-Hyp-Pro-Gly-Hyp-Pro-Gly-Arg-Pro-Lys-

Pro-Gln-Gln-Phe-Phe-Gly-Leu-Met;

(SEQ ID NO: 392)
Pro-Hyp-Gly-Pro-Hyp-Gly-Pro-Hyp-Gly-Pro-Hyp-Gly-

Pro-Hyp-Gly-Pro-Hyp-Gly-Pro-Hyp-Gly-Arg-Pro-Lys-

Pro-Gln-Gln-Phe-Phe-Gly-Leu-Met;

(SEQ ID NO: 393)
Flp-Hyp-Gly-Flp-Hyp-Gly-Flp-Hyp-Gly-Flp-Hyp-Gly-

Flp-Hyp-Gly-Flp-Hyp-Gly-Flp-Hyp-Gly-Arg-Pro-Lys-

Pro-Gln-Gln-Phe-Phe-Gly-Leu-Met;

(SEQ ID NO: 394)
Clp-Hyp-Gly-Clp-Hyp-Gly-Clp-Hyp-Gly-Clp-Hyp-Gly-

Clp-Hyp-Gly-Clp-Hyp-Gly-Clp-Hyp-Gly-Arg-Pro-Lys-

Pro-Gln-Gln-Phe-Phe-Gly-Leu-Met;

(SEQ ID NO: 395)
Pro-Flp-Gly-Pro-Flp-Gly-Pro-Flp-Gly-Pro-Flp-Gly-

Pro-Flp-Gly-Pro-Flp-Gly-Pro-Flp-Gly-Arg-Pro-Lys-

Pro-Gln-Gln-Phe-Phe-Gly-Leu-Met;
and (SEQ ID NO: 419)
Pro-Clp-Gly-Pro-Clp-Gly-Pro-Clp-Gly-Pro-Clp-Gly- Pro-Clp-Gly-Pro-Clp-Gly-Pro-Clp-Gly-Arg-Pro-Lys- Pro-Gln-Gln-Phe-Phe-Gly-Leu-Met.

In other methods of the invention, the one or more therapeutic or diagnostic compounds are suitably conjugated or attached to the CMPs via a covalent bond other than a peptide bond (see, e.g., U.S. Pat. Nos. 3,283,414 and 3,883,964, which are incorporated herein by reference in their entireties). For example, therapeutic compounds can be attached directly to a cysteine or methionine residue on a CMP described herein by covalently bonding a hydroxyl or amino group on an amino acid residue (e.g., a lysine residue) on the therapeutic or diagnostic compound (if it is a biologic molecule) to a sulfhydryl group on the cysteine or methionine residue of the CMP. Alternatively, if the CMP does not contain a cysteine or methionine residue, the one or more therapeutic or diagnostic compounds can be attached or conjugated to the CMP by a reaction between a hydroxyl group or amino group on the CMP and a sulfhydryl group on an amino acid residue (e.g., at a cysteine or methionine residue) on the therapeutic or diagnostic compound (if it is a biologic molecule). In yet another alternative method of conjugation, therapeutic compounds can be attached directly to a lysine residue on a CMP described herein by covalently bonding the therapeutic compound to an amino group on the lysine, for example using NHS ester conjugation (see, e.g., Mattson, G., et al., Molec. Biol. Rep. 17:167-183 (1993); Grabarek, Z. and Gergely, J., Anal. Biochem. 185:131-135 (1990); Staros, J. V. et al., Anal. Biochem. 156:220-2 (1986); Timkovich, R., Anal. Biochem. 79:135-43 (1977)). Such direct covalent attachments or conjugations between the CMP and the therapeutic/diagnostic compound can be accomplished using standard reaction techniques that will be familiar to those of ordinary skill in organic chemistry.

In other embodiments, particularly those wherein the therapeutic or diagnostic compound is not a biologic (and therefore does not have a peptide structure or amino acid residues having groups suitably attachable to cysteine, methionine, lysine or other residues on the CMP), such as small molecule organic or inorganic therapeutic or diagnostic compounds, the at least one therapeutic or diagnostic compound is indirectly attached to the collagen mimetic peptide via use of an attachment means. In such embodiments, the attachment means has two attachable ends, one of which attaches to an amino acid residue, and suitably a sulfhydryl group on a cysteine or methionine residue or an amino group on a lysine residue, of a CMP, and the other of which attaches to a hydroxyl or amino group on the therapeutic or diagnostic compound. For example, in certain such embodiments the attachment means comprises at least one polymeric chain having a first end and a second end, and the first end of the polymeric chain binds to the sulfhydryl group on a cysteine or methionine residue or an amino group on a lysine residue on the collagen mimetic peptide and the opposite or second end of the polymeric chain binds to an amino group or hydroxyl group on the therapeutic compound. In embodiments where the therapeutic or diagnostic compound is a biologic that is not suitable for direct attachment via peptide synthesis as described elsewhere herein, the second end of the attachment means can be attached to an amino group on an amino acid residue, such as a lysine residue, on the biologic therapeutic or diagnostic compound. Suitable such attachment means are well-known to those of ordinary skill in the art. For example, one attachment means suitable for use in accordance with this aspect of the invention includes a moiety which is a polymeric chain that on one end (the CMP-binding end in particular) comprises a sulfhydryl-binding group such as a maleimide, and on the other end (the therapeutic or diagnostic compounding-binding end in particular) comprises an amino-binding group such as N-hydroxysuccinimide. In certain such embodiments, the polymeric chain is a linear polyethyleneglycol chain comprising at least four ethyleneglycol monomers, e.g., from four to fifty ethyleneglycol monomers, from ten to forty ethyleneglycol monomers, from fifteen to thirty ethyleneglycol monomers, from fifteen to twenty-five ethyleneglycol monomers, from twenty to twenty-five ethyleneglycol monomers, and particularly four, six, eight, twelve, twenty, twenty-two, twenty-three, twenty-four or twenty-five ethyleneglycol monomers. Such attachment means suitable for attaching one or more therapeutic or diagnostic compounds to a CMP by the methods described herein are available commercially, e.g., from Thermo Fisher Scientific (Waltham, Mass.) (e.g., SM(PEG)$_6$, SM(PEG)$_8$, SM(PEG)$_{12}$ and SM(PEG)$_{24}$). By adjusting the length of the polymer chain, the bioavailability and sustainability of the therapeutic or diagnostic compound in vivo can be modulated—the use of longer polymer chains, e.g., a polymer comprising 24 ethyleneglycol monomers, will increase the rate of bioavailability of the compound once the CMP-TC has been introduced into the body of the human or veterinary animal, while the use of shorter polymer chains, e.g., a polymer comprising six ethyleneglycol monomers, will decrease the rate of bioavailability and thus increase the sustainability (or, in other words, will result in delayed release or sustained release) of the therapeutic or diagnostic compound. Other conjugates using linear or star-shaped PEG moieties which may be suitably prepared using the CMPs of the present invention, and used in the therapeutic and diagnostic methods of the invention, are disclosed in U.S. Pat. Nos. 8,283,414 and 8,883,964, which are incorporated herein by reference in their entireties. Hence, according to certain such aspects of the invention, the at least one therapeutic compound comprises at least one reactive hydroxyl group capable of being cross-linked to the collagen mimetic peptide using a polymeric linker.

Other indirect attachment methods for conjugating the one or more therapeutic or diagnostic compounds into or onto the CMPs also are suitably used according to the invention. For example, the at least one therapeutic or diagnostic compound can be enclosed within at least one nanoparticle that is attached via an attachment means, such as those described herein, to the collagen mimetic peptide. Alternatively, the collagen mimetic peptide can suitably comprise at least one biotin moiety and the therapeutic molecule can suitably comprise at least one avidin or streptavidin moiety, and the biotin moiety on the collagen mimetic peptide will bind to the avidin or streptavidin moiety on the therapeutic or diagnostic compound, thereby attaching the collagen mimetic peptide to the therapeutic or diagnostic compound. Of course, the alternative is also suitable for use, in which the collagen mimetic peptide can suitably comprise at least one avidin or streptavidin moiety and the therapeutic or diagnostic compound can suitably comprise at least one biotin moiety, and the biotin moiety on the at least one therapeutic or diagnostic compound will bind to the avidin or streptavidin moiety on the collagen mimetic peptide, thereby attaching the collagen mimetic peptide to the therapeutic compound.

Thus, according to certain embodiments of the invention, the therapeutic or diagnostic compounds can be suitably attached directly to the CMPs described herein. In other embodiments of the invention, the one or more therapeutic or diagnostic compounds can be attached indirectly to the CMPs described herein, for example via the use of a spacer, linker or bridge moiety. It is to be understood that whether the one or more therapeutic compounds are attached directly or indirectly to the CMPs, such attachment results in the production of conjugates of the CMPs and the one or more therapeutic compounds, which may be defined herein as CMP-TC conjugates.

Suitable therapeutic or diagnostic compounds for attachment or conjugation to the CMPs to produce the CMP-TCs of the present invention include any compound that has been shown to have particular therapeutic or preventative properties against one or more diseases, disorders, physical conditions or afflictions when introduced into a human or veterinary animal suffering from or predisposed to such diseases, disorders, physical conditions or afflictions. Provided that the therapeutic or diagnostic compound is capable of being conjugated or attached to at least one CMP according to the teachings herein, any therapeutic or diagnostic compound can be used in the conjugates, compositions and methods of the present invention. Suitable such therapeutic compounds may be biologic or non-biologic (e.g., so-called "small molecule") therapeutic compounds. Compounds suitable for use include, but are not limited to, a steroidal anti-inflammatory drug, (e.g., prednisolone or a pharmaceutically acceptable salt thereof, such as prednisolone acetate), a nonsteroidal anti-inflammatory drug (e.g., acetylsalicylic acid, acetaminophen, ibuprofen, naproxen, nepafenac, bromfenac, diclofenac, flurbiprofen, ketoprofen, ketorolac, and an indene derivative (e.g., indomethacin, sulindac (Clinoril) and the like; see, e.g., U.S. Pat. No. 7,601,874, which is incorporated herein by reference in its entirety, for other indene derivatives suitably used as active pharmaceutical ingredients), and pharmaceutically acceptable salts, esters and derivatives thereof), a topical anesthetic (e.g., tetracaine, lidocaine, oxybuprocaine, proparacaine, and the like), a vitamin or a vitamin derivative or vitamin precursor (e.g., retinol, tretinoin, retinal, carotene and other retinoids and retinoid derivatives or precursors; folate; α-tocopherol; calciferol; phylloquinone, menadione and other vitamin K forms, precursors or derivatives, ascorbate; and the like), a therapeutic enzyme or a therapeutic fragment thereof (e.g., a collagenase and a serine protease, or a therapeutically effective fragment thereof), an antibiotic (e.g., an aminoglycoside antibiotic (such as gentamycin, tobramycin, paromomycin, kanamycin, neomycin and amikacin, and a pharmaceutically acceptable salt or ester thereof, e.g., tobramycin sulfate), a fluoroquinolone antibiotic (such as moxifloxacin, gatifloxacin, levofloxacin, gemifloxacin, ciprofloxacin, norfloxacin and ofloxacin, and a pharmaceutically acceptable salt, ester or derivative thereof, e.g., moxifloxacin hydrochloride, ciprofloxacin hydrochloride and gatifloxacin hydrochloride), a sulfonamide antibiotic (such as sulfacetamide, sulfadiazine, sulfadimidine, sulfafurazole (sulfisoxazole), sulfisomidine (sulfaisodimidine), sulfadoxine, sulfamethoxazole, sulfamoxole, sulfanitran, sulfadimethoxine, sulfamethoxypyridazine, sulfametoxydiazine, sulfametopyrazine and terephtyl, and a pharmaceutically acceptable salt, ester or derivative thereof), a β-lactam antibiotic (such as a penicillin or a derivative thereof (for example penicilline G, penicillin V, a benzylpenicillin and phenoxymethylpenicillin), dicloxacillin, flucloxacillin, oxacillin, nafcillin, amoxicillin, an ampicillin, ticarcillin, piperacillin, ritipenem, a carbapenem (e.g., ertapenem, doripenem, imipenem and meropenem, and a pharmaceutically acceptable salt, ester or derivative thereof), a cephem (such as cefazolin, cefalexin, cefadroxil, cefapirin, cefaclor, cefotetan, cephamycin (cefoxitin), cefprozil, cefuroxime axetil, ceftriaxone, ceftazidime, cefoperazone, cefdinir, cefcapene, cefdaloxime, ceftizoxime, cefmenoxime, cefotaxime, cefpiramide, cefpodoxime, ceftibuten, cefditoren, cefepime, ceftaroline fosamil, ceftolozane, ceftobiprole, ceftiofur, cefquinome and cefovecin, and a pharmaceutically acceptable salt, ester or derivative thereof), a monobactam (such as aztreonam or a pharmaceutically acceptable salt, ester or derivative thereof) and a β-lactamase inhibitor (such as sulbactam, tazobactam, clavulanic acid and avibactam, and a pharmaceutically acceptable sat, ester or derivative thereof)) or a cyclic peptide antibiotic (such as cyclosporine), a therapeutic monoclonal antibody or a therapeutic fragment thereof (such as adalimumab, altumomab, atezolizumab, atlizumab, bevacizumab, canakinumab, catumaxomab, certolizumab, cetuximab, clivatuzumab, edrecolomab, efalizumab, fontolizumab, girentuximab, golimumab, infliximab, labetuzumab, MABpl (Xilonix™) natalizumab, nimotuzumab, nivolumab, oregovomab, panitumumab, pembrolizumab, pemtumomab, pertuzumab, ramucirumab, ranibizumab, rituximab, ruplizumab, tracatuzumab, tocilizumab, trastuzumab, ustekinumab, vedolizumab, visilizumab, votumumab, zalutumumab and zanolimumab, and active fragments, combinations or conjugates thereof), a therapeutic fusion protein (in certain embodiments, a recombinant fusion protein such as aflibercept (Regeneron), etanercept (Amgen), alefacept (Astellas Pharma), abatacept (Bristol-Myers Squibb), rilonacept (Regeneron), romiplostim (Amgen) and belatacept (Bristol-Myers Squibb)), a prostaglandin analogue (such as latanoprost, travoprost, tafluprost, unoprostone, netarsudil, tatanoprostene bunod, netarsudil and bimatoprost, and pharmaceutically acceptable salts, esters and derivatives thereof), a growth factor (such as EGF, PDGF, TGF-β, IGF-1, VEGF, FGF-β, IGF-1) or a therapeutic or growth-promoting (particularly skin growth-promoting) fragment thereof, a neuropeptide (such as Substance P (SEQ ID NO:389), an α-adrenergic antagonist (such as brimonidine, clonidine and apraclonidine, and pharmaceutically acceptable salts, esters or derivatives thereof), a β-adrenergic antagonist (such as timolol, propranolol, atenolol, levobunolol, carteolol, betaxolol, and pharmaceutically acceptable salts, esters and derivatives thereof, e.g., timolol maleate), a cell surface receptor antagonist (such as lifitegrast or etanercept), a carbonic anhydrase inhibitor (such as dorzolamide, brinzolamide, methazolamide and acetazolamide, and pharmaceutically acceptable salts, esters and derivatives thereof, e.g., dorzolamide hydrochloride), and pharmaceutically acceptable salts, esters and derivatives thereof. With certain such therapeutic compounds, administration simultaneously with the CMPs described herein, whether as a CMP-TC conjugate or simply with one or more CMPs and one or more TCs in an admixture or applied separately, may prevent, attenuate or lessen one or more adverse side effects of the therapeutic compound. For example, it is known that the therapeutic administration of certain fluoroquinolone antibiotics may cause damage to collagen and collagen-containing structures (e.g., tendons) in humans or veterinary animals who have been treated with fluoroquinolones (see, e.g., "FDA Drug Safety Communication: FDA updates warnings for oral and injectable fluoroquinolone antibiotics due to disabling side effects," accessed Nov. 6, 2017, at https://www.fda.gov/Drugs/DrugSafety/ucm511530.htm). As a result, simultaneous or co-administration of one or more of the CMPs described herein with one or more fluoroquinolone antibiotics to a human or veterinary animal in need of treatment with fluoroquinolones may allow the patient to receive the therapeutic benefits of the fluoroquinolone while mitigating, ameliorating or avoiding the collagen disruption resulting from such therapy, as the CMP can localize to and repair areas of damaged collagen in vivo.

Other suitable therapeutic compounds for use in the CMP-TC compounds, compositions and conjugates of the present invention include other non-biologic small molecule therapeutic compounds, including but not limited to alkylating agents, anti-tumor antibiotics, antimetabolites, hormonal agents, plant alkaloids, angiogenesis inhibitor, GnRH agonists, tyrosine kinase inhibitors, and the like. Examples of such non-biologic small molecule therapeutic compounds suitably used in accordance with the invention include but are not limited to a nitrosourea, a lenalidomide, imatinib, penatrexed, bortexomib, abiraterone acetate, everolimus, taxol, docetaxel, paclitaxel, carbazitaxel, mitoxantrone, carboplatin, cisplatin, gemcitabine, doxorubicin, casodex, flutamide, enzalutamide, abiraterone, sipuleucel-T and ketoconazole. Other suitable non-biologic small molecule therapeutic compounds that are advantageously used in forming the CMP-TC conjugates of the present invention, particularly for producing CMP-TC conjugates that are useful in treating certain cancers and preventing tumor metastasis, include inhibitors of lysyl oxidase (LOX), lysyl oxidase-like 1 (LOXL1) and lysyl oxidase-like 2 (LOXL2) enzymes. Such inhibitors have been suggested to have potential therapeutic application in treating and/or preventing certain cancers and the metastasis of solid tumors (see, e.g., U.S. Pat. Nos. 5,201,456; 5,120,764; 5,252,608; 8,461,303; 8,658,167; 8,680,246; 9,176,139; 9,255,086; and 9,289,447; see also Erler, J. T., et al., Nature 440:1222-1226 (2006); Erler, J. T., et al., Cancer Cell 15(1):35-44 (2009); Bondareva, A., et al., PLoS ONE 4(5):e5620 (2009); Granchi, C., et al., ChemMedChem 4(10:1590-1594 (2009); and Fang, M., et al., Tumor Biol. 35:2871-2882 (2014); the disclosures of all of which are incorporated herein by reference in their entireties). In related aspects of the invention, CMP-TC conjugates comprising one or more inhibitors of LOX or LOX-like enzymes are suitably used in treating and/or preventing certain fibrotic diseases and disorders that are mediated by oxidoreductase enzymes such as LOX and the LOX-like enzymes (e.g., LOXL1 and LOXL2) in humans and veterinary animals. Fibrotic diseases and disorders suitably treated and/or prevented according to this aspect of the invention include but are not limited to pulmonary fibrosis, liver cirrhosis, myocardial fibrosis, surgical scarring, systemic sclerosis, scleroderma, keloid formation, proliferative vitreo retinopathy, and other fibrotic diseases and disorders that will be familiar to those of ordinary skill in the relevant arts. Particularly useful inhibitors of LOX and the Lox-like proteins include β-aminopropionitrile and certain derivatives and prodrugs thereof (see, e.g., U.S. Pat. Nos. 5,201,456; 5,120,764; 5,252,608; 8,461,303; 8,680,246; 9,176,139; and 9,255,086; the disclosures of all of which are incorporated herein in their entireties), as well as antibodies (which may be polyclonal or, preferably monoclonal) and fragments or portions thereof which bind to and inhibit the activity or function of LOX and LOX-like enzymes (see, e.g., U.S. Pat. No. 8,461,303; the disclosure of which is incorporated herein in its entirety).

In additional embodiments, compounds or compositions can be prepared comprising one or more CMPs and one or more antigens, either in admixture or co-formulation of one or more CMPs with one or more antigens (and optionally with one or more pharmaceutically suitable carriers or excipients), or in other compounds or compositions in which the one or more antigens are linked or conjugated directly or indirectly to the one or more CMPs. According to certain such aspects, the antigen may be a complete antigen or antigenic determinant or a fragment thereof (e.g., a hapten) that is capable of inducing an immune response in a human or veterinary animal when presented in the appropriate physiological context to the immune system of the human or veterinary animal, such as in the form of administration of the compound, conjugate or composition in the form of a vaccine or immunization to the human or veterinary animal. Compounds, conjugates and compositions useful in such embodiments can be prepared via co-formulation or direct or indirect conjugation according to the methods described elsewhere herein for co-formulation and conjugation of therapeutic compounds with or to CMPs. Antigens or portions thereof suitable for use in such compounds, conjugates and compositions, and therefore in methods of use thereof, include any molecule or particle, or portion thereof, that is capable of inducing an immune response in the human or veterinary animal, including but not limited to antigens (e.g., proteins, toxins, lipids, and other antigenic moieties, molecules or complexes) arising from or produced by bacteria (in which the antigen may comprise the entire bacterium or a portion thereof, such as a cell wall or cell membrane component, a nuclear component or a toxin produced by the bacterium), viruses (in which the antigen may comprise the entire viral particle or a portion thereof, such as a coat component (e.g., a protein or lipid or portion thereof), a nuclear component, or an enzyme encoded by or which is a part of the viral particle), protists, fungi, plants (which may include plant irritants or allergens such as pollen particles), animals (from which the antigen or portion thereof may be an allogeneic antigen or autogeneic antigen, or a portion thereof), and the like; examples of such antigens or portions thereof will be readily familiar to those in the relevant arts. Such compounds, compositions or conjugates are suitably used in methods for treating and/or preventing one or more disorders, diseases and afflictions in humans and veterinary animals, for example through the use of the compounds, compositions or conjugates in creating an immune response in the animal or veterinary human. In certain such methods, a disease or disorder is treated and/or prevented in the animal or veterinary animal by administration of one or more of the compounds, compositions or conjugates of this aspect of the invention into the human or veterinary animal, such as in the form of a vaccine or immunization. Such vaccines or immunizations are suitably formulated according to methods that are well-known in the relevant arts, and are administered in any mode that will result in the development of an immune response by the human or veterinary animal to the antigen or portion thereof, thereby treating and/or preventing the disease or disorder caused directly or indirectly by the antigen or portion thereof. Such vaccines or immunizations can be administered to the human or veterinary animal by any suitable route, such as orally, parenterally (including subcutaneously, intradermally, transdermally, intrathecally or intravenously), via ocular administration (e.g., in the form of drops, gels, wafers, or via injection, as described elsewhere herein for CMP-TC administration to the eye), intranasally, and other routes of administration that will be familiar to those of ordinary skill. In such embodiments, the compounds, conjugates or compositions of the invention are suitably administered to the human or veterinary animal until an immune response is developed by the human or veterinary animal that is sufficient to treat and/or prevent the target disease or disorder, and may be readministered as necessary to boost the immune response and/or to ensure continued immunity to the target antigen or portion thereof. Diseases and disorders suitably treated by such methods of the invention include any disease or disorder involving or resulting from the activity of any foreign agent acting upon the cells, organs, organ systems, bodily structures or bodies of humans and veterinary animals, including but not limited to infectious diseases, cancers, allergies and other immune overreactions (e.g., graft-versus-host or host-versus-graft diseases), Stevens-Johnson Syndrome, mucus membrane pemphigoid, toxic epidermal necrolysis, Behcet disease uveitis, birdshot retinochoroidopathy, juvenile idiopathic arthritis (JIA)-associated uveitis, multifocal choroiditis with panuveitis, necrotizing scleritis, serpiginous choroidopathy, sympathetic ophthalmia, Vogt-Koyanagi-Harada (VKH) disease, non-infectious panuveitis, and the like.

Suitable diagnostic compounds for attachment or conjugation to CMPs to produce the conjugates and compositions of the invention include, but are not limited to, labeled probes, such as fluorescent dyes (e.g., quantum dots, indocyanine green, fluorescein, rhodamine, a merocyanine dye, a near-infrared fluorescent dye, and the like); a radioisotope, a nuclide used for PET, a nuclide used for SPECT, particularly wherein each of the radioisotope, the nuclide used for PET or SPECT is selected from the group consisting of $^{11}$C, $^{13}$N, $^{15}$O, $^{18}$F, $^{66}$Ga, $^{67}$Ga, $^{68}$Ga, $^{60}$Cu, $^{61}$Cu, $^{62}$Cu, $^{67}$Cu, $^{64}$Cu, $^{48}$V, Tc-99m, $^{241}$Am, $^{55}$Co, $^{57}$Co, $^{153}$Gd, $^{111}$In, $^{133}$Ba, $^{82}$Rb, $^{139}$Ce, Te-123m, $^{137}$Cs, $^{86}$Y, $^{90}$Y, $^{185/187}$Re, $^{186/188}$Re, $^{125}$I, a complex thereof, and a combination thereof; and an MRI contrast medium, a CT contrast medium, and a magnetic material, particularly wherein each of the MRI contrast medium, the CT contrast medium, and the magnetic material is selected from the group consisting of gadolinium, Gd-DTPA, Gd-DTPA-BMA, Gd-HP-D03A, iodine, iron, iron oxide, chromium, manganese, a complex or chelate complex thereof, and a combination thereof. According to such aspects of the invention, the CMP and the labeled probe are suitably physically or chemically bound directly to each other, for example via a direct conjugation through a coordinate bond, a covalent bond, a hydrogen bond, a hydrophobic interaction or a physical adsorption, or indirectly via use of at least one attachment means such as those described herein and others that are known in the art. Methods of conjugating or attaching diagnostic compounds to proteins, such as CMPs, are known in the art (see, e.g., U.S. Publ. Patent Appl. No. US 2012/0195828 A1, the disclosure of which is incorporated herein in its entirety).

Use of CMPs and CMP-TC Conjugates

Thus, the invention provides methods of preparing compositions that are useful in treating, preventing, diagnosing or ameliorating a disease, disorder or medical condition in humans or veterinary animals. In yet another aspect, the invention provides methods of treating, preventing, diagnosing or ameliorating a disease, disorder or medical or physical condition in humans or veterinary animals using the compositions of the invention. Particularly preferred CMPs for use in such aspects of the invention include CMPs comprising, consisting essentially of, or consisting of, CMPs having an amino acid sequence of (Pro-Pro-Gly)$_7$ (SEQ ID NO:1), (Flp-Pro-Gly)$_7$ (SEQ ID NO:4), (Pro-Flp-Gly)$_7$ (SEQ ID NO:5), (Flp-Hyp-Gly)$_7$ (SEQ ID NO:6), (Clp-Hyp-Gly)$_7$ (SEQ ID NO:9), (Hyp-Flp-Gly)$_7$ (SEQ ID NO:388), Gly$_3$-(Pro-Hyp-Gly)$_6$ (SEQ ID NO:[[397]]417), Gly$_3$-(Pro-Flp-Gly)$_6$ (SEQ ID NO: [[398]]418), Gly$_3$-(Pro-Hyp-Gly)$_7$ (SEQ ID NO:399), Gly$_3$-(Pro-Flp-Gly)$_7$ (SEQ ID NO:400), Gly$_3$-(Pro-Hyp-Gly)$_8$ (SEQ ID NO:401), Gly$_3$-(Pro-Flp-Gly)$_8$ (SEQ ID NO:402), Gly$_3$-(Pro-Hyp-Gly)$_9$ (SEQ ID NO:403), Gly$_3$-(Pro-Flp-Gly)$_9$ (SEQ ID NO:404), (Pro-Hyp-Gly)$_6$-Tyr (SEQ ID NO:405), (Pro-Flp-Gly)$_6$-Tyr (SEQ ID NO:406), (Pro-Hyp-Gly)$_7$-Tyr (SEQ ID NO:407), (Pro-Flp-Gly)$_7$-Tyr (SEQ ID NO:408), (Pro-Hyp-Gly)$_8$-Tyr (SEQ ID NO:409), (Pro-Flp-Gly)$_8$-Tyr (SEQ ID NO:410), Cys-(Pro-Hyp-Gly)$_3$ (SEQ ID NO:411), Cys-(Pro-Flp-Gly)$_3$ (SEQ ID NO:412), Cys-(Pro-Hyp-Gly)$_5$ (SEQ ID NO:413), Cys-(Pro-Flp-Gly)$_5$ (SEQ ID NO:414), Cys-(Pro-Hyp-Gly)$_7$ (SEQ ID NO:415), or Cys-(Pro-Flp-Gly)$_7$ (SEQ ID NO:416), and derivatives thereof comprising one or more cysteine, methionine or lysine residues such as those described elsewhere herein.

The CMPs and CMP-TC conjugates of the present invention, including solutions, gels, films, wafers, membranes, spheres, nanoparticles and suspensions comprising, consisting essentially of or consisting of the CMPs and/or CMP-TC conjugates of the present invention, are suitably used as or included in compositions for use in, or as, a medicament for treating, preventing or ameliorating a variety of diseases or disorders in humans or veterinary animals in need of treatment or prevention thereof. Other compositions provided by this aspect of the invention provide the use of CMPs conjugated to one or more diagnostic compounds or molecules, such as one or more labeled probes, which then are used as diagnostic reagents in a variety of tests and assays, particularly in vivo or in situ, to diagnose a disease, disorder, or physical condition in a human or veterinary animal. Such medicament compositions or diagnostic compositions may comprise, in addition to the CMPs, CMP-TC conjugates or CMPs conjugated to one or more diagnostic compounds or molecules, one or more additional therapeutic compounds or pharmaceutically active ingredients (e.g., one or more antibiotics, one or more growth factors, autologous plasma rich in growth factors (PRGF), one or more cytokines, one or more antibodies fragments thereof, one or more non-biologic small molecule therapeutic compounds, and pharmaceutically active salts, esters and derivatives thereof, and the like, including those described herein and others that are known in the art. The compositions of the invention may additionally or alternatively comprise one or more pharmaceutically acceptable carriers or excipients. Pharmaceutically acceptable carriers or excipients suitable for use in the compositions and methods of the invention include, for example, one or more solvents (which may include water, an organic solvent or an inorganic solvent), one or more buffers, one or more polymers, one or more salts, one or more sugars, one or more sugar alcohols, one or more disintegrating agents, one or more aerosolizing agents or carriers, one or more dessicants, and the like. Other pharmaceutically acceptable carriers or excipients suitable for use in the compositions of the present invention will be readily familiar to those of ordinary skill in the relevant arts.

Without wishing to be bound by theory, it is thought that the CMPs provided by the invention and used in the methods of the invention are useful in particular in repairing damaged collagen that results from or that is involved in a variety of diseases, disorders, structural abnormalities, physical conditions and medical conditions in humans and veterinary animals. For example, when collagen is damaged structurally it is fragmented and fractured into many smaller pieces which remain in the extracellular milieu or which find their way into the blood or lymphatic circulatory systems. Such fragments are ultimately either phagocytized or bound by scavenger cells, or bind to cell surface receptors on somatic cells in the human or veterinary animal. Such receptors (which may include, for example, integrins, discoidin-domain receptors, glycoprotein VI and leucocyte-associated immunoglobulin-like receptor-1 (LAIR-1)) control cellular functions such as growth, differentiation, morphogenesis, tissue repair, adhesion, migration, homeostasis, immune function and wound healing, are often disrupted, or their functions or signaling systems are up- or down-regulated, via the binding of such free collagen fragments. According to this theory, when CMPs encounter damaged collagen or fragments thereof they dynamically anneal to or bind the fractured collagen triple helix and structurally repair it, resulting in (among other things) the restoration of cellular receptors to their proper function and levels of signaling activity. Thus, in this way the aggregate result of the application of CMPs to a human or veterinary animal having a disease, disorder, structural abnormality or injury involving or resulting from damaged collagen is to unleash an accelerated wound healing process which in some physiological contexts includes rapid epithelial cell, endothelial cell or neural cell growth, migration and adhesion over the now repaired collagen matrix, resulting in the restoration of normal or near-normal structure and function of such cells, and tissues, organs and organ systems comprising such cells.

Diseases, disorders, physical conditions and medical conditions suitably treated, prevented, ameliorated or diagnosed using the compositions and methods of the invention include, but are not limited to ocular diseases or disorders, skin diseases or disorders, cancers, gastrointestinal diseases or disorders, genitourinary tract diseases or disorders, fibrotic diseases or disorders, cardiovascular diseases or disorders, bone diseases or disorders, rheumatic diseases or disorders and nerve or nervous system diseases or disorders.

Ocular diseases or disorders that can be treated, prevented, ameliorated or diagnosed using the compositions and methods of the invention include but are not limited to anterior segment diseases and disorders including but not limited to glaucoma, cataracts, vitreous adhesions or floaters, macular degeneration, dry eye syndrome (also known as dry eye disease), corneal keratitis, non-infectious corneal ulceration, non-infectious corneal melting, infectious corneal ulceration, infectious corneal melting, conjunctivitis, Stevens-Johnson Syndrome, scleritis, episcleritis, iritis, uveitis, vitritis, Behcet disease uveitis, birdshot retinochoroidopathy, juvenile idiopathic arthritis (JIA)-associated uveitis, multifocal choroiditis with panuveitis, necrotizing scleritis, serpiginous choroidopathy, sympathetic ophthalmia, Vogt-Koyanagi-Harada (VKH) disease, non-infectious panuveitis, ectasia, keratoconus, corneal lacerations, corneal erosion, corneal abrasions, acute or chronic corneal pain (particularly that resulting from damage or injury to the corneal nerves or denervation; see, e.g., Rosenthal, P. and Borsook, D., Br J Ophthalmol. 2016; 100(1):128-134; Theophanous, C., et al., Optom. Vis. Sci. 2015; 92(9):e233-240; Belmonte, C., et al., Ocul. Surf. 2004; 2(4):248-253; Belmonte, C., et al., Exp. Eye Res. 2004; 78(3):513-525; Belmonte, C., et al., Curr. Ophthalmol Rep. 2015; 3(2):111-121), including but not limited to paraocular pain, extraocular pain and post-herpetic neuralgia, and post-operative afflictions of the eye resulting from eye surgery. Such post-operative afflictions of the eye resulting from eye surgery can be, for example, afflictions arising post-operatively from cataract surgery or glaucoma surgery, particularly wherein those afflictions result in or are a post-operative state of the eye requiring medication. Other ocular diseases or disorders that can be treated, prevented, ameliorated or diagnosed using the compositions and methods of the invention include but are not limited to posterior segment diseases and disorders, particularly those involving the retina, including but not limited to macular degeneration (wet, dry and age-related), retinitis pigmentosa, retinal tears or detachment, retinopathy (e.g., diabetic retinopathy), arterial or venous occlusion (e.g., BRAO (Branch Retinal Artery Occlusion), CRAO (Central Retinal Artery Occlusion), BRVO (Branch Retinal Vein Occlusion) and CRVO (Central Retinal Vein Occlusion), optic neuritis, optic neuropathy (including, for example, AON (Anterior Ischemic Optic Neuropathy), and traumatic optic neuropathy), optic atrophy (e.g., glaucomatous optic atrophy), one or more neuropathies impacting the eye or area around the eye, including paraocular diseases, disorders or conditions and extraocular diseases, disorders or conditions, such as cranial nerve palsies including but not limited to Cranial III Nerve Palsy, Cranial Nerve IV Palsy, Cranial Nerve V Palsy (e.g., trigeminal neuralgia and post-herpes zoster neuralgia), Cranial Nerve VI Palsy and Cranial Nerve VII Palsy (e.g., Bell's Palsy)), and the like, and other retinal and posterior segment related disorders and diseases involving the retinal epithelium, particularly the retinal pigment epithelium, retinal blood vessels and/or retinal, cranial or optic nerves.

According to this aspect of the invention, methods of treating or preventing an ocular disease, disorder or wound in a human or veterinary animal suffering from or predisposed to an ocular disease, disorder or wound, comprise administering the compositions described herein, particularly the CMPs or CMP-TC conjugates and/or compositions comprising such conjugates, to an eye of a human or veterinary animal. Without wishing to be bound by theory, the inventors surmise that in areas of eye disease or disorder there is sufficient disruption of type I collagen such that the CMP will target the site of the eye disease or disorder specifically and intercalate into the collagen structure, thereby directly reforming a functioning collagen matrix or, in cases where the CMP is conjugated to a therapeutic compound, delivering the therapeutic compound to the site where it must act to treat, prevent or ameliorate the eye disease or disorder. In certain such anterior segment ocular diseases or disorders, such as acute or chronic corneal pain (including, but not limited to paraocular pain, extraocular pain, and post-herpetic neuralgia), denervated corneas suffer from poor healing capability and as such a topical therapy which can impact neuroregeneration would be a welcomed therapy in this area. Pain, both acute as well as chronic, is mediated by damaged corneal nerves (see, e.g., Rosenthal, P. and Borsook, D., Br J Ophthalmol. 2016; 100(1):128-134; Theophanous, C., et al., Optom. Vis. Sci. 2015; 92(9):e233-240; Belmonte, C., et al., Ocul. Surf 2004; 2(4):248-253; Belmonte, C., et al., Exp. Eye Res. 2004; 78(3):513-525; Belmonte, C., et al., Curr. Ophthalmol Rep. 2015; 3(2):111-121), and thus a therapeutic which could be beneficial to nerve health would be clinically valuable for such patients. Based on the findings described herein relating to the behavior of dorsal root ganglion cells when exposed to a CMP of the invention (SEQ ID NO:1) after damage to a collagen support layer (see Example 4 hereinbelow), it can be expected that any cranial nerve would behave in a similar way. Corneal nerves, as branches of the trigeminal nerve, will therefore benefit from a therapy which includes the administration of one or more of the CMPs or CMP-TC conjugates described herein topically to the cornea. With a repaired and regenerated nerve, corneal recovery and pain relief would then follow, resulting in the amelioration of the acute or chronic corneal pain.

The conjugates or compositions are suitably applied to the eye in a dosage sufficient to treat or prevent the ocular disease, disorder or wound, and the condition of the eye in said human or veterinary animal is then monitored over time for improvement in the disease state or physical condition. Suitable dosages for such uses are concentrations of about 10 ng/ml to about 500 ng/ml, about 15 ng/ml to about 400 ng/ml, about 20 ng/ml to about 300 ng/ml, about 25 ng/ml to about 250 ng/ml, about 30 ng/ml to about 200 ng/ml, about 35 ng/ml to about 200 ng/ml, about 40 ng/ml to about 200 ng/ml, about 50 ng/ml to about 200 ng/ml, about 75 ng/ml to about 200 ng/ml, and about 100 ng/ml to about 200 ng/ml. In certain such embodiments, the conjugates or compositions are suitably applied to the eye in dosages of about 25 ng/ml to about 500 ng/ml, e.g., about 25 ng/ml, about 30 ng/ml, about 35 ng/ml, about 40 ng/ml, about 45 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 300 ng/ml, about 350 ng/ml, about 400 ng/ml, about 450 ng/ml or about 500 ng/ml. In particular such embodiments, concentrations of between about 25 ng/ml and 250 ng/ml are used. Additional concentrations and amounts of the conjugates or compositions of the invention that are suitably used in such methods can be easily determined by one of ordinary skill, based on the information contained herein and that is available in the art, without the need to resort to undue experimentation. If necessary, the conjugate or composition of the invention is then periodically readministered to the eye, according to dosing and treatment schedules and protocols described herein and others that will be familiar to the ordinarily skilled artisan, until the ocular disease, disorder or wound is cured, prevented or ameliorated. In such embodiments, the conjugates or compositions of the invention for treatment of anterior segment diseases and disorders can be suitably administered to the eye to the surface of the eye, conjunctivally, or subconjunctivally, particularly by administering the conjugate or composition dropwise onto the surface of the eye or into the subconjunctival fornix. In other embodiments involving treatment, prevention, cure or diagnosis of posterior segment diseases and disorders, the conjugates and compositions of the invention can be administered to the posterior segment, e.g., at or near the retina, via mechanical introduction such as via injection using a needle or other suitable apparatus, or by administration of the conjugate or composition to the surface of the eye in the form of drops, in which the conjugate or composition (or component thereof, e.g., a CMP or CMP-TC conjugate) is transported or migrates to the posterior segment of the eye (e.g., at or near the retina) (see, e.g., Example 5 hereinbelow). Administration of the conjugates or compositions to the eye can be accomplished by any well-known means, including applying the conjugates or compositions to the eye in the form of one or more drops or aliquots of a solution, a gel or a suspension that contains the composition or conjugates; via injection; in the form of a solid material such as a wafer or film (such as those described herein) that is implanted into an eye structure; in the form of a mesh or patch; by attaching the conjugate or composition to, or enclosing it within, one or more gels, spheres or nanoparticles that are then delivered into an eye structure. Other suitable methods of applying the conjugates or compositions to the eye to accomplish the therapeutic and diagnostic methods of the invention will be readily apparent to the ordinarily skilled artisan.

Skin diseases or disorders that can be treated, prevented, ameliorated or diagnosed using the compositions and methods of the invention include but are not limited to skin wounds, scarring, wrinkles, "crepey skin", skin cancer (e.g., melanomas, skin carcinomas, skin sarcomas, histiocytomas) and skin burns, including sunburn. Other skin diseases or disorders suitably treated, prevented, ameliorated or diagnosed according to the invention include psoriasis and eczema, shingles, irritant contact dermatitis and allergic contact dermatitis (such as poison ivy, poison oak or poison sumac).

According to this aspect of the invention, methods of treating or preventing a skin disease, disorder or wound in a human or veterinary animal suffering from or predisposed to a skin disease, disorder or wound, comprise administering the compositions described herein, particularly the CMPs and CMP-TC conjugates, and compositions comprising such CMPs and CMP-TC conjugates, to the skin of a human or veterinary animal at a site proximal to the location of a lesion associated with or causing the skin disease, wound or disorder. Without wishing to be bound by theory, the inventors surmise that in areas of skin disease or disorder there is sufficient disruption of type I collagen such that the CMP will target the site of the skin disease or disorder specifically and intercalate into the collagen structure, thereby directly reforming a functioning collagen matrix or, in cases where the CMP is conjugated to a therapeutic compound, thereby delivering the CMP and/or therapeutic compound to the site where it must act to treat, prevent or ameliorate the skin disease or disorder. Alternatively, the disease or disorder afflicting the skin can be excised or resected from the skin (e.g., via surgical removal, for example of a skin cancer); and the skin wound resulting from such excision or resection can be treated with one or more compositions of the invention according to the methods described herein. In certain embodiments, one or more of the CMPs themselves, or one or more CMP-TC conjugates, or any combination thereof, can be introduced into the skin, particularly intraepidermally, intradermally or subcutaneously, in the form of a so-called "cosmeceutical" (see, e.g., Epstein, H., Clin. Dermatol. 27(5):453-460 (2009)). Particularly preferred CMP-TC conjugates or compositions for use in such aspects of the invention include those wherein the therapeutic compound is Substance P (SEQ ID NO:389), particularly those wherein the CMP-TC conjugate has an amino acid sequence corresponding to any one of SEQ ID NOs: 390-396. Additional particularly preferred CMP-TC conjugates or compositions for use in such aspects of the invention include those wherein the therapeutic compound is retinol or a derivative or precursor thereof. Additional preferred compositions comprise such compositions that comprise or further comprise at least one growth factor, at least one antibiotic, at least one antifungal compound or at least one antiviral compound. Suitable growth factors, antibiotics, antifungal compounds and antiviral compounds include those described herein and others that are well-known in the dermatological and other relevant arts. According to this aspect of the invention, the conjugates or compositions are suitably applied to or into the skin in a dosage sufficient to treat or prevent the skin disease, disorder or wound, and the condition of the skin in said human or veterinary animal is then monitored over time for improvement in the disease state or physical condition. Suitable dosages for such uses are concentrations of about 10 ng/ml to about 500 ng/ml, about 15 ng/ml to about 400 ng/ml, about 20 ng/ml to about 300 ng/ml, about 25 ng/ml to about 250 ng/ml, about 30 ng/ml to about 200 ng/ml, about 35 ng/ml to about 200 ng/ml, about 40 ng/ml to about 200 ng/ml, about 50 ng/ml to about 200 ng/ml, about 75 ng/ml to about 200 ng/ml, and about 100 ng/ml to about 200 ng/ml. In certain such embodiments, the conjugates or compositions are suitably applied to the eye in dosages of about 25 ng/ml to about 500 ng/ml, e.g., about 25 ng/ml, about 30 ng/ml, about 35 ng/ml, about 40 ng/ml, about 45 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 300 ng/ml, about 350 ng/ml, about 400 ng/ml, about 450 ng/ml or about 500 ng/ml. Additional concentrations and amounts of the conjugates or compositions of the invention that are suitably used in such methods can be easily determined by one of ordinary skill, based on the information contained herein and that is available in the art, without the need to resort to undue experimentation. If necessary, the conjugate or composition of the invention is then periodically readministered to or into the skin, according to dosing and treatment schedules and protocols described herein and others that will be familiar to the ordinarily skilled artisan, until the skin disease, disorder or wound is cured, prevented or ameliorated. In such embodiments, the conjugates or compositions of the invention are suitably administered to or into the skin topically, intraepidermally, intradermally or subdermally. Administration of the conjugates or compositions to or into the skin can be accomplished by any well-known means, including in the form of a solution, an ointment, a salve, a patch, a cream, a topical solution and a drug eluting wafer. For example, the conjugates or compositions can be applied to or introduced into the skin in the form of one or more drops of solution or a suspension that contains the composition or conjugates; via injection; in the form of a coating on a solid material that is implanted into the skin; in the form of a mesh or patch; by attaching the conjugate or composition to, or enclosing it within, one or more nanoparticles that are then delivered into the skin. Other suitable methods of applying the conjugates or compositions to or into the skin to accomplish the therapeutic and diagnostic methods of the invention will be readily apparent to the ordinarily skilled artisan.

Cancers that can be treated, prevented, ameliorated or diagnosed using the compositions and methods of the invention include but are not limited to skin cancers (e.g., those described elsewhere herein), intraluminal cancers and brain cancers. Intraluminal cancers suitably treated, prevented, diagnosed or ameliorated using the conjugates, compositions and methods of the invention include but are not limited to colorectal cancer, intestinal cancer, duodenal cancer, stomach cancer, pancreatic cancer, esophageal cancer, a bladder cancer (e.g., non-muscle-invasive bladder cancer or carcinoma in situ of the bladder), a cancer of the upper urinary tract, alternatively referred to and also known to those of ordinary skill as the renal pelvis (e.g., upper tract urothelial carcinoma, Wilms tumor and renal cancer), vaginal cancer, cervical cancer, uterine cancer, ovarian cancer, luminal breast cancer and lung cancer. Brain cancers suitably treated, prevented, diagnosed or ameliorated using the conjugates, compositions and methods of the invention include but are not limited to gliomas, glioblastomas, meningiomas, pituitary tumors, craniopharyngioma and hemangioblastomas. Other non-luminal cancers are also suitably treated, prevented, diagnosed or ameliorated using the conjugates, compositions and methods of the invention, including but not limited to prostate cancer, testicular cancer, non-luminal breast cancer, bone cancer, head and neck cancer, thyroid cancer, liver cancer, sarcomas (e.g., Kaposi sarcoma, Ewing sarcoma, osteosarcoma, soft tissue sarcoma and rhabdomyosarcoma), and the like.

According to this aspect of the invention, methods of treating or preventing a cancer in a human or veterinary animal suffering from or predisposed to a cancer, comprise administering the compositions described herein, particularly the CMPs and CMPs and/or conjugates, into the organ lumen, or into the cranium or into or on the brain, of a human or veterinary animal, at a site proximal to the location of the cancer or tumor. Without wishing to be bound by theory, the inventors surmise that in areas of cancer there is sufficient disruption of type I collagen, or upregulation of type I collagen in the case of brain cancer, such that the CMP will target the site of the cancer specifically and intercalate into the collagen structure, thereby directly reforming a functioning collagen matrix or, in cases where the CMP is conjugated to a therapeutic compound, thereby delivering the CMP and/or therapeutic compound to the site where it must act to treat, prevent or ameliorate the cancer. Particularly preferred conjugates or compositions for use in this aspect of the invention include those wherein the therapeutic compound is a biologic therapeutic compound, particularly one or more monoclonal antibodies or fragments thereof or one or more therapeutic fusion proteins, particularly recombinant fusion proteins, including those described herein. Additional preferred compositions comprise such compositions that further comprise at least one growth factor, at least one antibiotic, at least one antifungal compound or at least one antiviral compound. Suitable growth factors, antibiotics, antifungal compounds and antiviral compounds include those described herein and others that are well-known in the dermatological and other relevant arts. According to this aspect of the invention, the conjugates or compositions are suitably applied to or into the organ lumen, or the cranium or brain, in a dosage sufficient to treat, prevent or ameliorate the cancer, and the progression, remission or stasis of the cancer in the human or veterinary animal is then monitored over time for improvement in the cancer disease state (e.g., shrinkage of the tumor or at least non-progression or remission of the cancer). Suitable dosages for such uses are concentrations of about 10 ng/ml to about 500 ng/ml, about 15 ng/ml to about 400 ng/ml, about 20 ng/ml to about 300 ng/ml, about 25 ng/ml to about 250 ng/ml, about 30 ng/ml to about 200 ng/ml, about 35 ng/ml to about 200 ng/ml, about 40 ng/ml to about 200 ng/ml, about 50 ng/ml to about 200 ng/ml, about 75 ng/ml to about 200 ng/ml, and about 100 ng/ml to about 200 ng/ml. In certain such embodiments, the conjugates or compositions are suitably applied to the eye in dosages of about 25 ng/ml to about 500 ng/ml, e.g., about 25 ng/ml, about 30 ng/ml, about 35 ng/ml, about 40 ng/ml, about 45 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 300 ng/ml, about 350 ng/ml, about 400 ng/ml, about 450 ng/ml or about 500 ng/ml. Additional concentrations and amounts of the conjugates or compositions of the invention that are suitably used in such methods can be easily determined by one of ordinary skill, based on the information contained herein and that is available in the art, without the need to resort to undue experimentation. If necessary, the conjugate or composition of the invention is then periodically readministered into the organ lumen, or into the cranium or into or on the brain, according to dosing and treatment schedules and protocols described herein and others that will be familiar to the ordinarily skilled artisan, until the cancer is cured, prevented or ameliorated, or goes into permanent remission. In such embodiments, the conjugates or compositions of the invention are suitably administered to or into the organ lumen or the brain parenterally or via direct application to the tumor site or, in the case of excision or resection of the tumor, via direct application to the tumor bed or the wound remaining following excision or resection of the tumor. Parenteral administration of the conjugates or compositions of the invention can be accomplished via a route selected from the group consisting of subcutaneous injection, intravenous infusion, intraarterial infusion, transdermal diffusion, implantation of a drug eluting wafer or film, sublingually, orally, via aerosol inhalation, intravaginally, rectally, or intracranially. In certain such embodiments the conjugate or composition can be administered parenterally to the human or veterinary animal in the form of a mesh, film, wafer, sphere, nanoparticle, gel or patch that is implanted into the human or veterinary animal at or proximal to the site of the cancer. In other such embodiments, particularly those in which the cancer is an intraluminal cancer, the conjugates or compositions of the invention can be administered to the lumen of the cancerous organ in the human or veterinary animal using a medical instrument suitable for such purpose, such as an endoscope, a bronchoscope (for example, via bronchial lavage for treating, preventing or diagnosing a cancer of the pulmonary tract such as bronchial cancer or lung cancer), a proctoscope, a colonoscope, a cystoscope (e.g., into the bladder or upper urinary tract via cystoscopic irrigation), a gastroscope and a laparoscope, or other suitable surgical/medical instruments capable of delivering a dose of a medicament such as the conjugates and compositions of the invention to the human or veterinary animal at the site of the cancer. In certain such embodiments, the conjugate or composition can be administered following surgical excision or resection of a solid tumor, or removal or aspiration of a tumor ascites using, e.g., a trochar introduced into the abdomen for removal of abdominal ascites fluid. In such embodiments, the conjugate or composition of the invention (along with, optionally, one or more additional therapeutic agents) can be introduced directly into the surgical excision or into the ascites area, for example through any of the instruments or devices described above.

In other embodiments, administration of the conjugates or compositions to or into the organ lumen or the brain can be accomplished by any well-known means, including in the form of a solution, an ointment, a salve, a patch, a cream, a topical solution and a drug eluting wafer. For example, the conjugates or compositions can be applied to or introduced into the lumen of the organ or into or on the brain in the form of one or more drops of solution or a suspension that contains the composition or conjugates; via injection; in the form of a coating on a solid material that is implanted into the organ lumen or the brain; in the form of a mesh or patch; by attaching the conjugate or composition to, or enclosing it within, one or more nanoparticles that are then delivered into the organ lumen or the brain. Other suitable methods of applying the conjugates or compositions to or into the organ lumen or the brain to accomplish the therapeutic and diagnostic methods of the invention will be readily apparent to the ordinarily skilled artisan.

Gastrointestinal diseases or disorders that can be treated, prevented, ameliorated or diagnosed using the compositions and methods of the invention include but are not limited to irritable bowel syndrome, Crohn's Disease, an ulcer, ulcerative colitis, esophagitis, Barrett's esophagitis, gastritis and proctitis.

According to this aspect of the invention, methods of treating or preventing a gastrointestinal disease or disorder in a human or veterinary animal suffering from or predisposed to a gastrointestinal disease or disorder comprise administering the compositions described herein, particularly the CMPs and CMP-TC conjugates and compositions comprising such CMPs and/or conjugates, into the gastrointestinal tract of a human or veterinary animal, at a site proximal to the location of a lesion associated with or causing the gastrointestinal disease or disorder. Without wishing to be bound by theory, the inventors surmise that in areas of certain gastrointestinal diseases and disorders there is sufficient disruption of type I collagen such that the CMP will target the site of the gastrointestinal disease or disorder specifically and intercalate into the collagen structure, thereby directly reforming a functioning collagen matrix or, in cases where the CMP is conjugated to a therapeutic compound, thereby delivering the CMP and/or therapeutic compound to the site where it must act to treat, prevent or ameliorate the gastrointestinal disease or disorder. Particularly preferred conjugates or compositions for use in this aspect of the invention include those wherein the therapeutic compound is a biologic therapeutic compound, particularly one or more monoclonal antibodies or fragments thereof or one or more therapeutic fusion proteins, particularly recombinant fusion proteins, including those described herein. According to this aspect of the invention, the conjugates or compositions are suitably applied to or into the gastrointestinal tract in a dosage sufficient to treat, prevent or ameliorate the gastrointestinal disease or disorder, and the progression, remission or stasis of the gastrointestinal disease or disorder in the human or veterinary animal is then monitored over time for improvement in the disease or disorder state. Suitable dosages for such uses are concentrations of about 10 ng/ml to about 500 ng/ml, about 15 ng/ml to about 400 ng/ml, about 20 ng/ml to about 300 ng/ml, about 25 ng/ml to about 250 ng/ml, about 30 ng/ml to about 200 ng/ml, about 35 ng/ml to about 200 ng/ml, about 40 ng/ml to about 200 ng/ml, about 50 ng/ml to about 200 ng/ml, about 75 ng/ml to about 200 ng/ml, and about 100 ng/ml to about 200 ng/ml. In certain such embodiments, the conjugates or compositions are suitably applied to the eye in dosages of about 25 ng/ml to about 500 ng/ml, e.g., about 25 ng/ml, about 30 ng/ml, about 35 ng/ml, about 40 ng/ml, about 45 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 300 ng/ml, about 350 ng/ml, about 400 ng/ml, about 450 ng/ml or about 500 ng/ml. Additional concentrations and amounts of the conjugates or compositions of the invention that are suitably used in such methods can be easily determined by one of ordinary skill, based on the information contained herein and that is available in the art, without the need to resort to undue experimentation. If necessary, the conjugate or composition of the invention is then periodically readministered into the gastrointestinal tract according to dosing and treatment schedules and protocols described herein and others that will be familiar to the ordinarily skilled artisan, until the gastrointestinal disease or disorder is cured, prevented or ameliorated. In such embodiments, the conjugates or compositions of the invention are suitably administered to or into the gastrointestinal tract parenterally or topically. Parenteral administration is accomplished by any art-known route of administration of a therapy to the gastrointestinal tract, for example via a route selected from the group consisting of subcutaneous injection, intravenous infusion, intraarterial infusion, transdermal diffusion, implantation of a drug eluting wafer, sublingually, orally or rectally. In such methods, the composition is suitably administered parenterally to the human or veterinary animal in the form of a pill, capsule, solution, suspension or powder that is ingested by the human or veterinary animal, or in the form of a mesh or patch that is implanted within the gastrointestinal tract at or proximal to the site of the disease or disorder. In other such embodiments, particularly those in which the disease or disorder is intraluminal in the gastrointestinal tract, the conjugates or compositions of the invention can be administered to the lumen of the gastrointestinal organ in the human or veterinary animal using a medical instrument suitable for such purpose, such as a proctoscope, a colonoscope, a cystoscope (e.g., into the bladder or upper urinary tract cystoscopically), a gastroscope and a laparoscope, or other suitable surgical/medical instruments capable of delivering a dose of a medicament such as the conjugates and compositions of the invention to the human or veterinary animal at the site of the gastrointestinal disease or disorder.

In other embodiments, administration of the conjugates or compositions to or into the gastrointestinal tract can be accomplished by any well-known means, including in the form of a solution, an ointment, a salve, a patch, a cream, a topical solution and a drug eluting wafer. For example, the conjugates or compositions can be applied to or introduced into the gastrointestinal tract in the form of one or more drops of solution or a suspension that contains the composition or conjugates; via injection; in the form of a coating on a solid material that is implanted into the gastrointestinal tract; in the form of a mesh or patch; by attaching the conjugate or composition to, or enclosing it within, one or more nanoparticles that are then delivered into the gastrointestinal tract. Other suitable methods of applying the conjugates or compositions to or into the gastrointestinal tract to accomplish the therapeutic and diagnostic methods of the invention will be readily apparent to the ordinarily skilled artisan.

Genitourinary diseases or disorders that can be treated, prevented, ameliorated or diagnosed using the compositions and methods of the invention include but are not limited to female urinary incontinence, cystitis, interstitial cystitis, irritable bladder syndrome, ureteritis and vaginitis.

According to this aspect of the invention, methods of treating or preventing a genitourinary disease or disorder in a human or veterinary animal suffering from or predisposed to a genitourinary disease or disorder comprise administering the compositions described herein, particularly the CMPs and CMP-TC conjugates and compositions comprising such CMPs and/or conjugates, into the genitourinary tract of a human or veterinary animal, at a site proximal to the location of a lesion associated with or causing the genitourinary tract disease or disorder. Without wishing to be bound by theory, the inventors surmise that in areas of certain genitourinary diseases and disorders there is sufficient disruption of type I collagen such that the CMP will target the site of the genitourinary disease or disorder specifically and intercalate into the collagen structure, thereby directly reforming a functioning collagen matrix or, in cases where the CMP is conjugated to a therapeutic compound, thereby delivering the CMP and/or therapeutic compound to the site where it must act to treat, prevent or ameliorate the genitourinary disease or disorder. According to this aspect of the invention, the conjugates or compositions are suitably applied to or into the genitourinary tract in a dosage sufficient to treat, prevent or ameliorate the genitourinary disease or disorder, and the progression, remission or stasis of the genitourinary disease or disorder in the human or veterinary animal is then monitored over time for improvement in the disease or disorder state. Suitable dosages for such uses are concentrations of about 10 ng/ml to about 500 ng/ml, about 15 ng/ml to about 400 ng/ml, about 20 ng/ml to about 300 ng/ml, about 25 ng/ml to about 250 ng/ml, about 30 ng/ml to about 200 ng/ml, about 35 ng/ml to about 200 ng/ml, about 40 ng/ml to about 200 ng/ml, about 50 ng/ml to about 200 ng/ml, about 75 ng/ml to about 200 ng/ml, and about 100 ng/ml to about 200 ng/ml. In certain such embodiments, the conjugates or compositions are suitably applied to the eye in dosages of about 25 ng/ml to about 500 ng/ml, e.g., about 25 ng/ml, about 30 ng/ml, about 35 ng/ml, about 40 ng/ml, about 45 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 300 ng/ml, about 350 ng/ml, about 400 ng/ml, about 450 ng/ml or about 500 ng/ml. Additional concentrations and amounts of the conjugates or compositions of the invention that are suitably used in such methods can be easily determined by one of ordinary skill, based on the information contained herein and that is available in the art, without the need to resort to undue experimentation. If necessary, the conjugate or composition of the invention is then periodically readministered into the genitourinary tract according to dosing and treatment schedules and protocols described herein and others that will be familiar to the ordinarily skilled artisan, until the genitourinary disease or disorder is cured, prevented or ameliorated. In such embodiments, the conjugates or compositions of the invention are suitably administered to or into the genitourinary tract parenterally or topically. Parenteral administration is accomplished by any art-known route of administration of a therapy to the gastrointestinal tract, for example via a route selected from the group consisting of subcutaneous injection, intravenous infusion, intraarterial infusion, transdermal diffusion, implantation of a drug eluting wafer, sublingually, orally, vaginally or rectally. In such methods, the composition is suitably administered parenterally to the human or veterinary animal in the form of a pill, capsule, solution, suspension or powder that is ingested by the human or veterinary animal, or in the form of a mesh or patch that is implanted within the genitourinary tract at or proximal to the site of the disease or disorder. In other such embodiments, particularly those in which the disease or disorder is intraluminal in the gastrointestinal tract, the conjugates or compositions of the invention can be administered to the lumen of the genitourinary organ in the human or veterinary animal using a medical instrument suitable for such purpose, such as an endoscope, a vaginoscope, and a laparoscope, or other suitable surgical/medical instruments capable of delivering a dose of a medicament such as the conjugates and compositions of the invention to the human or veterinary animal at the site of the genitourinary disease or disorder.

In other embodiments, administration of the conjugates or compositions to or into the genitourinary tract can be accomplished by any well-known means, including in the form of a solution, an ointment, a salve, a patch, a wafer, a film, a gel, spheres, nanoparticles, a cream, a topical solution and a drug eluting wafer. For example, the conjugates or compositions can be applied to or introduced into the genitourinary tract in the form of one or more drops of solution or a suspension that contains the composition or conjugates; via injection; in the form of a coating on a solid material that is implanted into the genitourinary tract; in the form of a mesh or patch; by attaching the conjugate or composition to, or enclosing it within, one or more nanoparticles that are then delivered into the genitourinary tract. Other suitable methods of applying the conjugates or compositions to or into the genitourinary tract to accomplish the therapeutic and diagnostic methods of the invention will be readily apparent to the ordinarily skilled artisan.

Fibrotic diseases or disorders that can be treated, prevented, ameliorated or diagnosed using the compositions and methods of the invention include but are not limited to pulmonary fibrosis, liver cirrhosis, myocardial fibrosis, surgical scarring, systemic sclerosis, scleroderma, keloid formation, proliferative vitreo retinopathy, and the like.

According to this aspect of the invention, methods of treating or preventing a fibrotic disease or disorder in a human or veterinary animal suffering from or predisposed to a fibrotic disease or disorder comprise administering the compositions described herein, particularly the CMPs and CMP-TC conjugates and compositions comprising such CMPs and/or conjugates, into or near one or more tissues, organs or organ systems of a human or veterinary animal, at a site proximal to the location of a fibrotic lesion associated with or causing the fibrotic disease or disorder. Without wishing to be bound by theory, the inventors surmise that in areas of certain fibrotic diseases and disorders there is sufficient disruption of type I collagen such that the CMP will target the site of the fibrotic disease or disorder specifically and intercalate into the collagen structure, thereby directly reforming a functioning collagen matrix or, in cases where the CMP is conjugated to a therapeutic compound, thereby delivering the therapeutic compound to the site where it must act to treat, prevent or ameliorate the fibrotic disease or disorder. According to this aspect of the invention, the conjugates or compositions are suitably applied to, near or into the tissue, organ or organ system in a dosage sufficient to treat, prevent or ameliorate the fibrotic disease or disorder, and the progression, remission or stasis of the fibrotic disease or disorder in the human or veterinary animal is then monitored over time for improvement in the disease or disorder state. Suitable dosages for such uses are concentrations of about 10 ng/ml to about 500 ng/ml, about 15 ng/ml to about 400 ng/ml, about 20 ng/ml to about 300 ng/ml, about 25 ng/ml to about 250 ng/ml, about 30 ng/ml to about 200 ng/ml, about 35 ng/ml to about 200 ng/ml, about 40 ng/ml to about 200 ng/ml, about 50 ng/ml to about 200 ng/ml, about 75 ng/ml to about 200 ng/ml, and about 100 ng/ml to about 200 ng/ml. In certain such embodiments, the conjugates or compositions are suitably applied to the eye in dosages of about 25 ng/ml to about 500 ng/ml, e.g., about 25 ng/ml, about 30 ng/ml, about 35 ng/ml, about 40 ng/ml, about 45 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 300 ng/ml, about 350 ng/ml, about 400 ng/ml, about 450 ng/ml or about 500 ng/ml. Additional concentrations and amounts of the conjugates or compositions of the invention that are suitably used in such methods can be easily determined by one of ordinary skill, based on the information contained herein and that is available in the art, without the need to resort to undue experimentation. If necessary, the conjugate or composition of the invention is then periodically readministered into, near or onto one or more tissues, organs or organ systems according to dosing and treatment schedules and protocols described herein and that will be familiar to the ordinarily skilled artisan, until the fibrotic disease or disorder is cured, prevented or ameliorated. In such embodiments, the conjugates or compositions of the invention are suitably administered to, near, on or into the tissues, organs or organ systems parenterally or topically. Parenteral administration is accomplished by any art-known route of administration of a therapy to the tissues, organ or organ systems, for example via a route selected from the group consisting of subcutaneous injection, intravenous infusion, intraarterial infusion, endoscopic application, transdermal diffusion, implantation of a drug eluting wafer, film, gel or putty, sublingually, orally or rectally. In such methods, the composition is suitably administered parenterally to the human or veterinary animal in the form of a pill, capsule, solution, suspension or powder that is ingested by the human or veterinary animal, or in the form of a mesh, film, wafer, gel, sphere, nanoparticle, putty or patch that is implanted near, on or into the fibrotic tissue, organ or organ system at or proximal to the site of the disease or disorder.

In other embodiments, administration of the conjugates or compositions to, near or into the tissues, organs or organ systems can be accomplished by any well-known means, including in the form of a solution, an ointment, a salve, a patch, a film, a gel, spheres, nanoparticles, putty, a cream, a topical solution and a drug eluting wafer. For example, the conjugates or compositions can be applied to or near, or introduced into, the tissues, organs or organ systems in the form of one or more drops of solution or a suspension that contains the composition or conjugates; via injection; in the form of a coating on a solid material that is implanted into, near or onto the tissues, organs or organ systems; in the form of a mesh or patch; by attaching the conjugate or composition to, or enclosing it within, one or more nanoparticles that are then delivered into, near or on the tissues, organs or organ systems. Other suitable methods of applying the conjugates or compositions to, on, near or into the tissues, organs or organ systems to accomplish the therapeutic and diagnostic methods of the invention will be readily apparent to the ordinarily skilled artisan.

Cardiovascular diseases or disorders that can be treated, prevented, ameliorated or diagnosed using the compositions and methods of the invention include but are not limited to myocardial infarction, cardiac insufficiency, cardiac valve disorders, atherosclerosis, cardiomyophathy, arrhythmias, congenital heart disease, coronary artery disease, pericardial disease, vascular occlusive disease (e.g., affecting the carotid artery, the aorta, the renal artery, the femoral artery, the pulmonary artery, and other large vessels and small vessels which may be arteries, arterioles, veins, venules and the like), Marfan syndrome, and the like.

According to this aspect of the invention, methods of treating or preventing a cardiovascular disease or disorder in a human or veterinary animal suffering from or predisposed to a cardiovascular disease or disorder comprise administering the compositions described herein, particularly the CMPs and/or CMP-TC conjugates and compositions comprising such CMPs and/or conjugates, into the vascular system of a human or veterinary animal suffering from or predisposed to such a disease or disorder. Without wishing to be bound by theory, the inventors surmise that in areas of certain cardiovascular diseases and disorders there is sufficient disruption of type I collagen such that the CMP introduced into the vascular system of the subject will target the site of the cardiovascular disease or disorder specifically and intercalate into the collagen structure, thereby directly reforming a functioning collagen matrix or, in cases where the CMP is conjugated to a therapeutic compound, thereby delivering the CMP and/or therapeutic compound to the site where it must act to treat, prevent or ameliorate the cardiovascular disease or disorder. According to this aspect of the invention, the conjugates or compositions are suitably applied to or into the vascular system in a dosage sufficient to treat, prevent or ameliorate the cardiovascular disease or disorder, and the progression, remission or stasis of the cardiovascular disease or disorder in the human or veterinary animal is then monitored over time for improvement in the disease or disorder state. Suitable dosages for such uses are concentrations of about 10 ng/ml to about 500 ng/ml, about 15 ng/ml to about 400 ng/ml, about 20 ng/ml to about 300 ng/ml, about 25 ng/ml to about 250 ng/ml, about 30 ng/ml to about 200 ng/ml, about 35 ng/ml to about 200 ng/ml, about 40 ng/ml to about 200 ng/ml, about 50 ng/ml to about 200 ng/ml, about 75 ng/ml to about 200 ng/ml, and about 100 ng/ml to about 200 ng/ml. In certain such embodiments, the conjugates or compositions are suitably applied to the eye in dosages of about 25 ng/ml to about 500 ng/ml, e.g., about 25 ng/ml, about 30 ng/ml, about 35 ng/ml, about 40 ng/ml, about 45 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 300 ng/ml, about 350 ng/ml, about 400 ng/ml, about 450 ng/ml or about 500 ng/ml. Additional concentrations and amounts of the conjugates or compositions of the invention that are suitably used in such methods can be easily determined by one of ordinary skill, based on the information contained herein and that is available in the art, without the need to resort to undue experimentation. If necessary, the conjugate or composition of the invention is then periodically readministered into the vascular system according to dosing and treatment schedules and protocols described herein and others that will be familiar to the ordinarily skilled artisan, until the cardiovascular disease or disorder is cured, prevented or ameliorated. In such embodiments, the conjugates or compositions of the invention are suitably administered to or into the heart, pericardium, vessel or other relevant component of the vascular system parenterally or topically. Parenteral administration is accomplished by any art-known route of administration of a therapy to the vascular system, for example via a route selected from the group consisting of subcutaneous injection, intravenous infusion, intraarterial infusion, transdermal diffusion, via catheterization, embolization, implantation of a drug eluting wafer or film, sublingually, orally, rectally. In such methods, the composition is suitably administered parenterally to the human or veterinary animal in the form of a pill, capsule, solution, suspension or powder that is ingested by the human or veterinary animal, or in the form of a mesh, wafer, film, gel, putty, sphere, nanoparticle or patch that is implanted within the heart, pericardium, vessel or other relevant component of the vascular system at or proximal to the site involved in the cardiovascular disease or disorder.

In other embodiments, administration of the conjugates or compositions to or into the vascular system can be accomplished by any well-known means, including in the form of a solution, an ointment, a salve, a patch, a film, a gel, spheres, nanoparticles, a cream, a topical solution and a drug eluting wafer. For example, the conjugates or compositions can be applied to or introduced into the heart, pericardium, vessel or other relevant component of the vascular system in the form of one or more drops of solution or a suspension that contains the composition or conjugates; via injection; in the form of a coating on a solid material that is implanted into the heart, pericardium, vessel or other relevant component of the vascular system; in the form of a mesh or patch; by attaching the conjugate or composition to, or enclosing it within, one or more nanoparticles that are then delivered into the heart, pericardium, vessel or other relevant component of the vascular system. Other suitable methods of applying the conjugates or compositions to or into the vascular system to accomplish the therapeutic and diagnostic methods of the invention will be readily apparent to the ordinarily skilled artisan.

Bone diseases or disorders that can be treated, prevented, ameliorated or diagnosed using the compositions and methods of the invention include but are not limited to osteoporosis, bone fracture, osteomyelitis, osteogenesis imperfecta, Paget disease of bone, osteonecrosis, rickets, osteomalacia, acromegaly and the like.

According to this aspect of the invention, methods of treating or preventing a bone disease or disorder in a human or veterinary animal suffering from or predisposed to a bone disease or disorder comprise administering the compositions described herein, particularly the CMPs and CMP-TC conjugates and compositions comprising such CMPs and/or conjugates, into or near one or more bones of a human or veterinary animal, at a site proximal to the location of a lesion associated with or causing the bone disease or disorder. Without wishing to be bound by theory, the inventors surmise that in areas of certain bone diseases and disorders there is sufficient disruption of type I collagen such that the CMP will target the site of the bone disease or disorder specifically and intercalate into the collagen structure, thereby directly reforming a functioning collagen matrix or, in cases where the CMP is conjugated to a therapeutic compound, thereby delivering the therapeutic compound to the site where it must act to treat, prevent or ameliorate the bone disease or disorder. According to this aspect of the invention, the conjugates or compositions are suitably applied to, near or into the bone in a dosage sufficient to treat, prevent or ameliorate the bone disease or disorder, and the progression, remission or stasis of the bone disease or disorder in the human or veterinary animal is then monitored over time for improvement in the disease or disorder state. Suitable dosages for such uses are concentrations of about 10 ng/ml to about 500 ng/ml, about 15 ng/ml to about 400 ng/ml, about 20 ng/ml to about 300 ng/ml, about 25 ng/ml to about 250 ng/ml, about 30 ng/ml to about 200 ng/ml, about 35 ng/ml to about 200 ng/ml, about 40 ng/ml to about 200 ng/ml, about 50 ng/ml to about 200 ng/ml, about 75 ng/ml to about 200 ng/ml, and about 100 ng/ml to about 200 ng/ml. In certain such embodiments, the conjugates or compositions are suitably applied to the eye in dosages of about 25 ng/ml to about 500 ng/ml, e.g., about 25 ng/ml, about 30 ng/ml, about 35 ng/ml, about 40 ng/ml, about 45 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 300 ng/ml, about 350 ng/ml, about 400 ng/ml, about 450 ng/ml or about 500 ng/ml. Additional concentrations and amounts of the conjugates or compositions of the invention that are suitably used in such methods can be easily determined by one of ordinary skill, based on the information contained herein and that is available in the art, without the need to resort to undue experimentation. If necessary, the conjugate or composition of the invention is then periodically readministered into, near or onto one or more bones according to dosing and treatment schedules and protocols described herein and others that will be familiar to the ordinarily skilled artisan, until the bone disease or disorder is cured, prevented or ameliorated. In such embodiments, the conjugates or compositions of the invention are suitably administered to, near, on or into the bones parenterally or topically. Parenteral administration is accomplished by any art-known route of administration of a therapy to the bones, for example via a route selected from the group consisting of subcutaneous injection, intravenous infusion, intraarterial infusion, endoscopic application, transdermal diffusion, implantation of a drug eluting wafer, film, gel or putty, sublingually, orally or rectally. In such methods, the composition is suitably administered parenterally to the human or veterinary animal in the form of a pill, capsule, solution, suspension or powder that is ingested by the human or veterinary animal, or in the form of a mesh, film, wafer, gel, sphere, nanoparticle, putty or patch that is implanted near, on or into the bone at or proximal to the site of the disease or disorder.

In other embodiments, administration of the conjugates or compositions to, near or into the bones can be accomplished by any well-known means, including in the form of a solution, an ointment, a salve, a patch, a film, a gel, spheres, nanoparticles, putty, a cream, a topical solution and a drug eluting wafer. For example, the conjugates or compositions can be applied to or near, or introduced into, the bones in the form of one or more drops of solution or a suspension that contains the composition or conjugates; via injection; in the form of a coating on a solid material that is implanted into, near or onto the bones; in the form of a mesh or patch; by attaching the conjugate or composition to, or enclosing it within, one or more nanoparticles that are then delivered into, near or on the bones. Other suitable methods of applying the conjugates or compositions to, on, near or into the bones to accomplish the therapeutic and diagnostic methods of the invention will be readily apparent to the ordinarily skilled artisan.

Rheumatic diseases or disorders that can be treated, prevented, ameliorated or diagnosed using the compositions and methods of the invention include but are not limited to arthritis (particularly rheumatoid arthritis, osteoarthritis and psoriatic arthritis), bursitis, crepitus, spondylosis, scleroderma, polymyalgia rheumatica and anarthritic syndrome.

According to this aspect of the invention, methods of treating or preventing a rheumatic disease or disorder in a human or veterinary animal suffering from or predisposed to a rheumatic disease or disorder comprise administering the compositions described herein, particularly the CMPs or CMP-TC conjugates and compositions comprising such CMPs and/or conjugates, to the human or veterinary animal at a site proximal to the location of a lesion associated with or causing the rheumatic disease or disorder. Without wishing to be bound by theory, the inventors surmise that in areas of certain rheumatic diseases and disorders there is sufficient disruption of type I collagen such that the CMP will target the site of the rheumatic disease or disorder specifically and intercalate into the collagen structure, thereby directly reforming a functioning collagen matrix or, in cases where the CMP is conjugated to a therapeutic compound, thereby delivering the therapeutic compound to the site where it must act to treat, prevent or ameliorate the rheumatic disease or disorder. According to this aspect of the invention, the conjugates or compositions are suitably applied to or into the human or veterinary animal in a dosage sufficient to treat, prevent or ameliorate the rheumatic disease or disorder, and the progression, remission or stasis of the rheumatic disease or disorder in the human or veterinary animal is then monitored over time for improvement in the disease or disorder state. Suitable dosages for such uses are concentrations of about 10 ng/ml to about 500 ng/ml, about 15 ng/ml to about 400 ng/ml, about 20 ng/ml to about 300 ng/ml, about 25 ng/ml to about 250 ng/ml, about 30 ng/ml to about 200 ng/ml, about 35 ng/ml to about 200 ng/ml, about 40 ng/ml to about 200 ng/ml, about 50 ng/ml to about 200 ng/ml, about 75 ng/ml to about 200 ng/ml, and about 100 ng/ml to about 200 ng/ml. In certain such embodiments, the conjugates or compositions are suitably applied to the eye in dosages of about 25 ng/ml to about 500 ng/ml, e.g., about 25 ng/ml, about 30 ng/ml, about 35 ng/ml, about 40 ng/ml, about 45 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 300 ng/ml, about 350 ng/ml, about 400 ng/ml, about 450 ng/ml or about 500 ng/ml. Additional concentrations and amounts of the conjugates or compositions of the invention that are suitably used in such methods can be easily determined by one of ordinary skill, based on the information contained herein and that is available in the art, without the need to resort to undue experimentation. If necessary, the conjugate or composition of the invention is then periodically readministered to the human or veterinary animal according to dosing and treatment schedules and protocols described herein and others that will be familiar to the ordinarily skilled artisan, until the rheumatic disease or disorder is cured, prevented or ameliorated. In such embodiments, the conjugates or compositions of the invention are suitably administered to or into the human or veterinary animal parenterally or topically. Parenteral administration is accomplished by any art-known route of administration of a therapy designed to treat, prevent or ameliorate a rheumatic disease or disorder, for example via a route selected from the group consisting of subcutaneous injection, intravenous infusion, intraarterial infusion, transdermal diffusion, implantation of a drug eluting wafer, sublingually, orally, vaginally or rectally. In such methods, the composition is suitably administered parenterally to the human or veterinary animal in the form of a pill, capsule, solution, suspension or powder that is ingested by the human or veterinary animal, or in the form of a mesh or patch that is implanted within the human or veterinary animal at or proximal to the site of the disease or disorder. In other such embodiments, particularly those in which the rheumatic disease or disorder is located in or near a bone, tendon, cartilage, ligament, bursa, joint or associated structure, the compositions or conjugates of the invention are suitably administered to the human or veterinary animal using a medical instrument suitable for such purpose, such as an laparoscope, or other suitable surgical/medical instruments capable of delivering a dose of a medicament such as the conjugates and compositions of the invention to the human or veterinary animal at the site of the genitourinary disease or disorder.

In other embodiments, administration of the conjugates or compositions to or into the human or veterinary animal can be accomplished by any well-known means, including in the form of a solution, an ointment, a salve, a patch, a cream, a topical solution and a drug eluting wafer. For example, the conjugates or compositions can be applied to or introduced into the human or veterinary animal in the form of one or more drops of solution or a suspension that contains the composition or conjugates; via injection; in the form of a coating on a solid material that is implanted into the human or veterinary animal; in the form of a mesh or patch; by attaching the conjugate or composition to, or enclosing it within, one or more nanoparticles that are then delivered into the human or veterinary animal. Other suitable methods of applying the conjugates or compositions to or into the human or veterinary animal to accomplish the therapeutic and diagnostic methods of the invention will be readily apparent to the ordinarily skilled artisan.

Nerve or nervous system (including the central nervous system ("CNS") and peripheral nervous system ("PNS") diseases or disorders that can be treated, prevented, ameliorated or diagnosed using the compositions and methods of the invention include but are not limited to injuries to one or more nerves or nerve processes (including axons, dendrites and neurons or neuronal bodies, ganglia, nerve bundles and the like), neurodegeneration (in many different physiological or disease contexts such as multiple sclerosis, amyotrophic lateral sclerosis, Parkinson's disease, Alzheimer's disease, Huntington's disease, a traumatic encephalopathy, a non-Alzheimer's dementia, encephalitis, meningitis, and the like), disorders involving peripheral nerves (such as diabetic peripheral neuropathy, nutritional neuropathy and alcohol-induced neuropathy), or certain neuroocular diseases and disorders including those involving or affecting the corneal nerves, retinal nerves and optic nerve, including but not limited to glaucoma, macular degeneration (wet and/or dry, which may or may not be age-related), neurotrophic keratitis, retinopathies (which may include diabetic retinopathy, ischemic retinopathy, a proliferative retinopathy, and other genetic-based retinopathies and genetic retinal diseases or disorders known in the art), damage to or inflammation of one or more corneal nerves (which may arise via damage to or inflammation of the eye via external diseases or trauma/wounding, including a transection of, or crush injury or torsional injury to, a nerve or nerve process), corneal pain (which may be acute or chronic, and which may result from damage or injury to the corneal nerves or corneal denervation, e.g., paraocular pain, extraocular pain, and post-herpetic neuralgia), an encephalopathy (e.g., traumatic encephalopathy such as concussion, encephalitis, meningitis), and the like. In certain such embodiments, the compositions and methods of the invention can be used to induce nerve repair or regrowth (e.g., via neuroregeneration), particularly in the cranial nerves including but not limited to the optic nerve, the retinal nerves, the acoustic nerve or the spinal nerve. In other such embodiments, the compositions and methods of the invention can be used to protect certain nerves from degeneration, or from further or continued degeneration (i.e., provide a neuroprotective function), which may, for example, be useful in preventing, reducing or slowing the progression of degeneration of the peripheral nerves for the prevention and/or treatment of diabetic peripheral neuropathy, nutritional neuropathy and alcohol-induced peripheral neuropathy, as well as of the corneal nerves, optic nerve and/or the retinal nerves for the prevention and/or treatment of corneal pain (e.g., acute corneal pain or chronic corneal pain, including but not limited to paraocular pain, extraocular pain, and post-herpetic neuralgia), glaucoma, genetic retinal diseases or disorders and genetic-based retinopathies (e.g., diabetic retinopathy). Other beneficial uses of the compositions and methods of the invention in treating, preventing, ameliorating or diagnosing nerve and nervous system diseases or disorders will be familiar to the ordinarily skilled artisan based on the guidance provided herein in view of information readily available in the relevant arts.

According to this aspect of the invention, methods of treating or preventing a nerve or nervous system disease or disorder in a human or veterinary animal suffering from or predisposed to a nerve or nervous system disease or disorder comprise administering the compositions described herein, particularly the CMPs and CMP-TC conjugates and compositions comprising such CMPs and/or conjugates, into or near one or more tissues, organs or organ systems of a human or veterinary animal, at a site proximal to the location of a nerve or nervous system lesion associated with or causing the nerve or nervous system disease or disorder. Without wishing to be bound by theory, the inventors surmise that in areas of certain nerve or nervous system diseases and disorders there is sufficient disruption of type I collagen (perhaps among other components of the local extracellular matrix) such that the CMP will target the site of the nerve or nervous system disease or disorder specifically and intercalate into the collagen structure, thereby inducing neuroregeneration and/or neuroprotection directly via reformation of a functioning collagen matrix, or in cases where the CMP carries a therapeutic compound delivering the therapeutic compound to the site where it must act to treat, prevent or ameliorate the nerve or nervous system disease or disorder. According to this aspect of the invention, the conjugates or compositions are suitably applied to, near or into the tissue, organ or organ system in a dosage sufficient to treat, prevent or ameliorate the nerve or nervous system disease or disorder, and the progression, remission or stasis of the nerve or nervous system disease or disorder in the human or veterinary animal is then monitored over time for improvement in the disease or disorder state. Suitable dosages for such uses are concentrations of about 10 ng/ml to about 500 ng/ml, about 15 ng/ml to about 400 ng/ml, about 20 ng/ml to about 300 ng/ml, about 25 ng/ml to about 250 ng/ml, about 30 ng/ml to about 200 ng/ml, about 35 ng/ml to about 200 ng/ml, about 40 ng/ml to about 200 ng/ml, about 50 ng/ml to about 200 ng/ml, about 75 ng/ml to about 200 ng/ml, and about 100 ng/ml to about 200 ng/ml. In certain such embodiments, the conjugates or compositions are suitably applied to the eye in dosages of about 25 ng/ml to about 500 ng/ml, e.g., about 25 ng/ml, about 30 ng/ml, about 35 ng/ml, about 40 ng/ml, about 45 ng/ml, about 50 ng/ml, about 75 ng/ml, about 100 ng/ml, about 125 ng/ml, about 150 ng/ml, about 175 ng/ml, about 200 ng/ml, about 225 ng/ml, about 250 ng/ml, about 300 ng/ml, about 350 ng/ml, about 400 ng/ml, about 450 ng/ml or about 500 ng/ml. Additional concentrations and amounts of the conjugates or compositions of the invention that are suitably used in such methods can be easily determined by one of ordinary skill, based on the information contained herein and that is available in the art, without the need to resort to undue experimentation. If necessary, the conjugate or composition of the invention is then periodically readministered into, near or onto one or more tissues, organs or organ systems according to dosing and treatment schedules and protocols described herein and that will be familiar to the ordinarily skilled artisan, until the nerve or nervous system disease or disorder is cured, prevented or ameliorated. In such embodiments, the conjugates or compositions of the invention are suitably administered to, near, on or into the tissues, organs or organ systems parenterally or topically. Parenteral administration is accomplished by any art-known route of administration of a therapy to the tissues, organ or organ systems, for example via a route selected from the group consisting of subcutaneous injection, intradermal injection, intramuscular injection, intracranial injection, intraspinal injection, or injection into any tissue, organ or organ system where a nerve or nervous system disease or disorder is being manifested; intravenous infusion; intraarterial infusion; endoscopic application; transdermal diffusion; implantation of a drug eluting wafer, film, gel or putty; sublingually; orally; or rectally. In certain such methods, the composition is suitably administered parenterally to the human or veterinary animal in the form of an injected solution or paste, a pill, a capsule, a solution, a suspension or a powder that is inhaled or ingested by the human or veterinary animal, or in the form of a mesh, film, wafer, gel, sphere, nanoparticle, paste, putty or patch that is implanted near, on or into the tissue, organ or organ system at or proximal to the site of the nerve or nervous system disease or disorder. In certain such embodiments, one or more of the compounds, compositions or conjugates of the invention may be coated onto or into a mesh or "sleeve" material such that the mesh or sleeve material is impregnated with one or more of the compounds, compositions or compositions of the invention, and the mesh or sleeve then applied to an injured (e.g., transected) or damaged nerve, nerve process or nerve bundle.

In other embodiments, administration of the conjugates or compositions to, near or into the tissues, organs or organ systems can be accomplished by any well-known means, including in the form of a solution, an ointment, a salve, a patch, a film, a gel, a paste, spheres, nanoparticles, putty, a cream, a topical solution and a drug eluting wafer. For example, the conjugates or compositions can be applied to or near, or introduced into, the tissues, organs or organ systems in the form of one or more drops of solution or a suspension that contains the composition or conjugates (for example, for use in the back of the eye, in the form of a topical transocular eyedrop); via injection; in the form of a coating on a solid material that is implanted into, near or onto the tissues, organs or organ systems; in the form of a mesh or patch; by attaching the conjugate or composition to, or enclosing it within, one or more nanoparticles that are then delivered into, near or on the tissues, organs or organ systems. Other suitable methods of applying the conjugates or compositions to, on, near or into the tissues, organs or organ systems to accomplish the therapeutic and diagnostic methods of the invention will be readily apparent to the ordinarily skilled artisan.

In related embodiments, the invention provides devices, particularly medical devices, suitable for treating or preventing a disease, disorder or medical condition in a human or veterinary animal suffering from or predisposed to said disease, disorder or medical condition. Such devices suitably will comprise at least one of the compositions of the present invention, in the form of a coating on the device or a composition that is embedded within the device such that it is released from or elutes from the device once implanted within the body of the human or veterinary animal. Suitable such devices include, but are not limited to, artificial joints, stents, catheters, sutures, bone screws, bone plates, prosthetics (e.g., artificial limbs, body structures, organs, etc.), absorbable or non-absorbable meshes, absorbable or non-absorbable patches, drug-releasing wafers, brain neurostimulators (e.g., deep brain neurostimulators), gastric stimulators, cochlear implants, cardiac defibrillators, cardiac pacemakers, insulin pumps, internal infusion pumps, and the like. Suitable other devices useful in accordance with this aspect of the invention will be readily apparent to the ordinarily skilled artisan.

The devices provided by this aspect of the invention are useful for treating, preventing, ameliorating or diagnosing diseases, disorders and medical conditions in humans or veterinary animals suffering from or predisposed to such diseases, disorders or medical conditions. In methods according to this aspect, one or more medical devices of the invention is implanted into the human or veterinary animal, and medical condition of the human or veterinary animal is monitored until the disease, disorder or medical condition is cured, ameliorated or prevented in the human or veterinary animal. Suitable diseases, disorders and medical conditions that may be cured, treated, ameliorated or prevented using the devices and methods of the invention include cancers (such as those described elsewhere herein), and diseases or disorders affecting an organ system of the human or veterinary animal including the integumentary system (particularly diseases or disorders of the skin such as those described in detail herein), the muscular system, the skeletal system (particularly diseases or disorder of the bones, joints, cartilage, tendons or ligaments such as those described in detail herein), the nervous system (particularly those of the brain or the eye (such as anterior segment eye diseases and disorders including but not limited to those involving the corneal nerves (such as corneal pain (which may be acute or chronic), including but not limited to that resulting from damage or injury to the corneal nerves or denervation, e.g., paraocular pain, extraocular pain, and post-herpetic neuralgia), glaucoma, cataracts, vitreous adhesions or floaters, macular degeneration, dry eye syndrome, corneal keratitis, non-infectious corneal ulceration, non-infectious corneal melting, infectious corneal ulceration, infectious corneal melting, conjunctivitis, Stevens-Johnson Syndrome, scleritis, episcleritis, iritis, uveitis, vitritis, Behcet disease uveitis, birdshot retinochoroidopathy, juvenile idiopathic arthritis (JIA)-associated uveitis, multifocal choroiditis with panuveitis, necrotizing scleritis, serpiginous choroidopathy, sympathetic ophthalmia, Vogt-Koyanagi-Harada (VKH) disease, non-infectious panuveitis, ectasia, keratoconus, corneal laceration, corneal erosion, corneal abrasion, and a post-operative affliction of the eye resulting from eye surgery such as a post-operative cataract surgery state requiring medication or a post-operative glaucoma surgery state requiring medication, or posterior segment eye disorders such as those involving the retina, retinal epithelium (particularly the retinal pigment epithelium), retinal blood vessels, retinal nerves or optic nerve, including but not limited to macular degeneration (wet, dry and age-related), retinitis pigmentosa, retinal tears and detachment, retinopathy (e.g., diabetic retinopathy), retinal arterial or venous occlusion (e.g., BRAO (Branch Retinal Artery Occlusion), CRAO (Central Retinal Artery Occlusion), BRVO (Branch Retinal Vein Occlusion) and CRVO (Central Retinal Vein Occlusion), optic neuritis, optic neuropathy (including, for example, AION (Anterior Ischemic Optic Neuropathy), traumatic optic neuropathy and optic atrophy (e.g., glaucomatous optic atrophy)), and other neuropathies impacting the eye or area around the eye, including paraocular diseases, disorders and medical conditions and extraocular diseases, disorders and medical conditions, such as cranial nerve palsies including but not limited to Cranial III Nerve Palsy, Cranial Nerve IV Palsy, Cranial Nerve V Palsy (e.g., trigeminal neuralgia and post-herpes zoster neuralgia), Cranial Nerve VI Palsy and Cranial Nerve VII Palsy (e.g., Bell's Palsy), the circulatory system, the lymphatic system, the respiratory system (including those diseases or disorders affecting the epiglottis, the trachea, a bronchus, a bronchiole or a lung in the human or veterinary animal, particularly those diseases and disorders described in detail herein), the endocrine system, the urinary/excretory system (including those diseases or disorders affecting the kidney, the ureter, the urinary bladder, the upper urinary tract (i.e., the renal pelvis), the ureter or the urethra of the human or veterinary animal, particularly those diseases and disorders described in detail herein), the reproductive system (including diseases and disorders affecting the testicle, the prostate, the penis, the vagina, the cervix, the uterus, a fallopian tube or an ovary in said human or veterinary animal, particularly those diseases and disorders described in detail herein), the digestive system (including those diseases or disorders affecting the esophagus, stomach, small intestine, colon or rectum in said human or veterinary animal, particularly those diseases and disorders described in detail herein), and nerves or the nervous system (including the peripheral nervous system and the central nervous system, particularly those nerve or nervous system disorders, diseases and injuries described in detail herein). Suitable methods for implanting one or more of the devices provided by this aspect of the invention into a human or veterinary animal, to accomplish the treatment, prevention, amelioration or diagnosis of a disease, disorder or medical or physical condition in the human or veterinary animal will be familiar to the person of ordinary skill in the relevant medical and surgical arts.

Concentrations of the CMPs, or of the CMP-TC conjugates, useful in treating, preventing, ameliorating or diagnosing one or more diseases or disorders according to the methods of the present invention will be readily apparent to the artisan ordinarily skilled in the pharmaceutical and medical arts. For unconjugated CMPs, suitable amounts or concentrations of CMPs to be administered to a subject, particularly a human or veterinary animal, suitable amounts or concentrations of CMPs to be used include those described hereinabove. Based on the guidance provided herein, one of ordinary skill in the medical, pharmaceutical and/or pharmacological arts can determine the appropriate amount of the conjugates and compositions of the invention to be used per kilogram (kg) of body mass of the human or veterinary animal. For conjugated CMP-TCs, the same amounts or concentrations of CMPs described herein, whether in concentration (e.g., ng/ml or µg/ml) or in amount (e.g., mg per kg of body mass), are suitably administered to the subject, and the amount of active pharmaceutical ingredient or biologic is calculated during the conjugation process to deliver therapeutically effective amounts of the desired active pharmaceutical ingredient or biologic, depending upon the disease or disorder that is to be treated, prevented, ameliorated or diagnosed in the human or veterinary animal. Suitable amounts or concentrations of active pharmaceutical ingredients or biologics to be used according to this aspect of the invention will be familiar to the ordinarily skilled artisan, and can be readily determined from information contained herein and other information that is available in the relevant arts.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1: Effect of CMPs and CMP-TC Conjugates on in Vivo Healing of Mouse Corneal Epithelium To examine the possible therapeutic effects of CMPs and CMP-TC conjugates of the invention, studies were designed to test certain CMPs and CMP-TC conjugates in an in vivo setting—the healing of the corneal epithelium in wounded mouse eyes. Female mice (8-week-old C57BL/6; seven mice per sample tested) were anesthetized, and corneas of the mouse eyes were wounded with a 1.5 mm superficial epithelial wound of sufficient depth to expose the anterior stroma thereby damaging and exposing the collagen matrix. Wounds were created via trephine, followed by an Algerbrush scouring technique (see Carlson, E., et al., "Impact of Hyaluronic Acid-Containing Artificial Tear Products on Reepithelialization in an in Vivo Corneal Wound Model," J. Ocular Pharmacol. Ther., published online Feb. 2, 2018, accessed at https://doi.org/10.1089/jop.2017.0080). Following wounding, corneas were treated with 25 nM (about 3 mg/kg) CMPs or CMP-TC conjugates, in aqueous PBS. Negative control mice were treated with vehicle only (PBS), and positive control mice were treated with 100 ng/mL epidermal growth factor (EGF). Wound size at various time points over 48 hours was examined by fluorescein staining (see Carlson et al., id.), and documented via fluorescent photomicrography, and quantified using Image J software (see Rush, J. S. et al., Investig. Ophthalmol. Visual Sci. 57(14):5864-5871 (2016); Rush, J. S. et al., Investig. Ophthalmol. Visual Sci. 55(8):4691-4699 (2014)). Results are depicted in FIG. 1.

FIG. 1 shows that the CMPs and CMP-TC conjugates of the invention significantly accelerated the reepithelialization and healing of the subepithelial stroma in the cornea of mouse eyes, vs. both EGF and vehicle. FIGS. 1a-1d show the size of the wound (visualized as the circle of fluorescein fluorescence in each photomicrograph) immediately after induction of the wound, while FIGS. 1e-1h show the size of the wound 16 hours post-wounding and post-treatment with various test substances. FIGS. 1a, 1e: PBS (negative control); FIGS. 1b, 1f: EGF (positive control); FIGS. 1c, 1g: "Compound 3", a (Pro-Pro-Gly)$_7$ CMP of the invention (SEQ ID NO:1); FIGS. 1d, 1h: "Compound 10", a (Hyp-Pro-Gly)$_7$ CMP—Substance P conjugate of the invention (SEQ ID NO:391). The results demonstrate that both CMPs of the invention (Compounds 3 and 10) demonstrated significant acceleration of wound healing in mouse cornea and corneal stroma (indicated by a reduction in the diameter and diminution in intensity of the fluorescence) within 16 hours post-treatment, compared to both PBS and EGF controls which showed a lower level of healing.

To examine the healing of corneal wounds at the histological level, mice were sacrificed 24 hours after wounding and treatment with either PBS or Compound 3 as above, eyes were removed and fixed in formalin and thin-sectioned, and sections stained with H&E and examined via light microscopy. The results of these experiments confirmed that within 24 hours of wounding and treatment with Compound 3 (FIG. 1j), the corneal epithelium demonstrated substantial healing (formation of an intact epithelial layer, and significantly lower edema and disorganization of the subepithelial stroma) compared to corneal epithelial sections taken from mouse eyes treated only with PBS (FIG. 1i). These results were confirmed at higher magnification (FIG. 2), where corneal sections from mouse eyes treated with PBS (FIG. 2a) showed substantial disruption of the subepithelial matrix and lacked a basement membrane (arrow). In contrast, corneal sections from mouse eyes treated with a Compound 3 CMP of the invention (FIG. 2b) showed healing of the cornea as indicated by an intact epithelial layer complete with a reformed basement membrane (arrow), as well as significantly reduced edema and disorganization of the subepithelial matrix. To determine the extent of healing, sections prepared as in FIG. 2 were examined microscopically and the average length of adhesion of the epithelial layer to the basement membrane and subepithelial stroma was measured. Results of these analyses are shown in FIG. 3, which showed that within 24 hours of treatment with 250 nM Compound 3, a CMP of the invention, corneal wounds had healed nearly completely (compare to naïve, i.e., unwounded, eye sections). In contrast, lower concentrations of Compound 3 were not as effective at inducing healing, but still performed better from a healing standpoint than did Compound 10 which gave results similar to what was seen with EGF and PBS.

Figure 2:
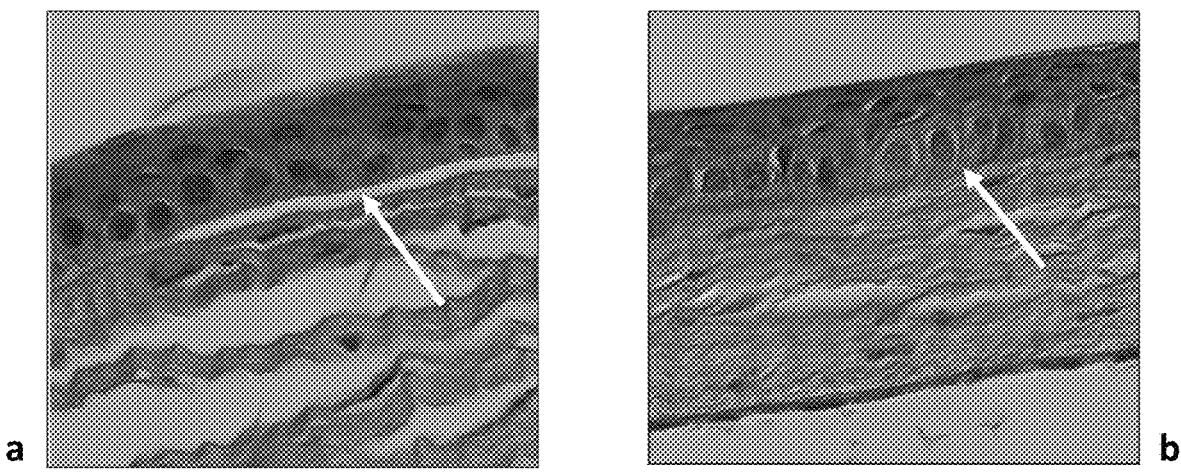
FIG. 2 is a high-power photomicrograph of H&E-stained sections of cornea from FIGS. 1i and 1j above.
Figure 3:
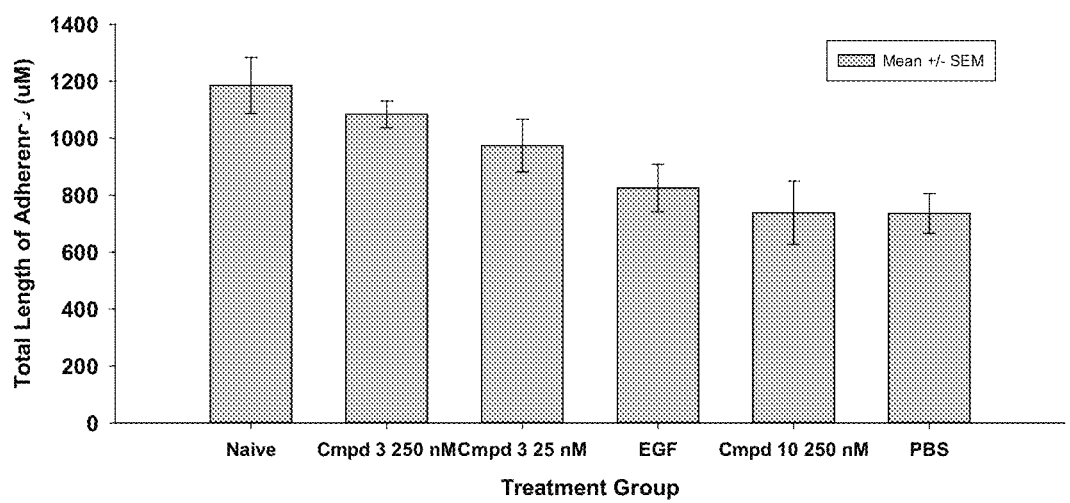
FIG. 3 is a bar graph of the length of adherence of the epithelial layer in wounded corneal tissue treated with PBS, EGF, Compound 3 or Compound 10, 24-hours post-treatment, vs. unwounded (naïve) cornea. Error bars are mean SEM, n=3.

Taken together, the results of FIGS. 1-3 support the use of the CMPs and CMP-TC conjugates of the present invention in promoting corneal wound healing and stromal collagen repair in wounded mouse eye, a model of a variety of human and veterinary animal ocular conditions including dry eye and corneal laceration or ulceration of a variety of etiologies.

Example 2: Effect of CMPs on Proliferation and Migration of Retinal Pigment Epithelial Cells To examine the possible therapeutic effects of CMPs and CMP-TC conjugates of the invention in back-of-eye indications, studies were designed to test certain CMPs and CMP-TC conjugates in an in vitro setting—the proliferation and migration of retinal pigment epithelial (RPE) cells. ARPE19 cells, a human RPE cell line expressing markers of differentiated RPE cells (see Dunn, K. C., et al., Exp. Eye Res. 62(2):155-170 (1996)), were obtained from ATCC (Manassas, Va.). Cells were plated (100,000 cells/ml at 2 ml per well) onto 100 mm collagen-coated tissue culture plates (coated with 100 µg/ml type I collagen (Advanced BioMatrix) for 2 hours at 37° C.) that had been pretreated with collagenase (Worthington Biochemical Corporation; 100 U/ml in TMC buffer for 1.5 hours at 37° C.) and then treated either with 100 µM Compound 3 (a (Pro-Pro-Gly)$_7$ CMP of the invention; SEQ ID NO:1) in TNC buffer, or with vehicle as negative control. Plates were incubated at 37° C. overnight and then evaluated via phase contrast microscopy for density, morphology and network formation. Representative results are shown in FIG. 4.

Figure 4:
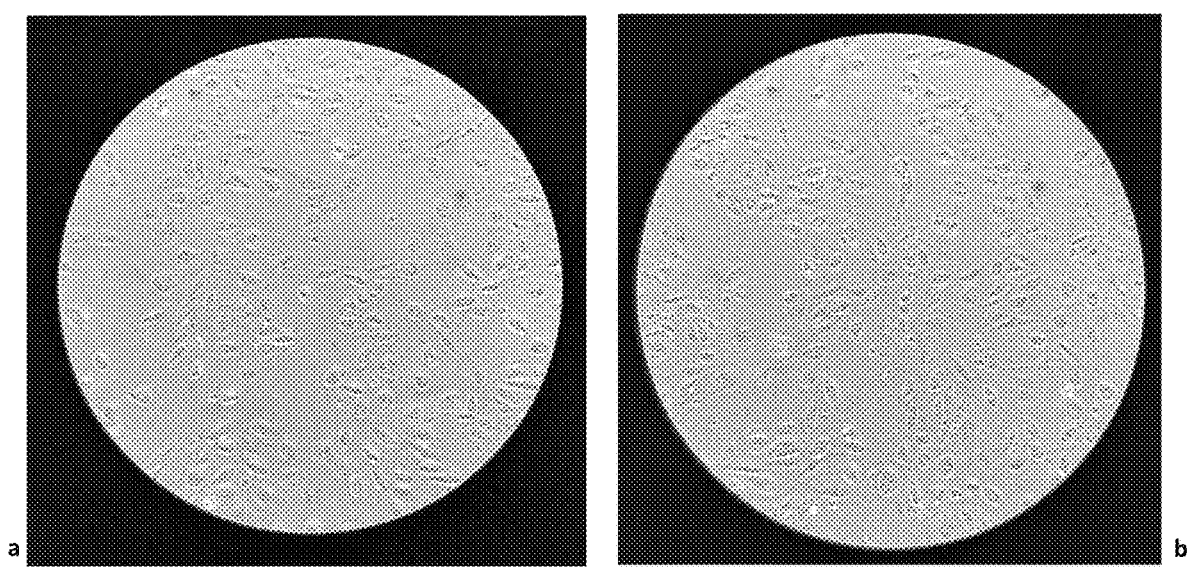
FIG. 4 is a phase contrast photomicrograph of retinal pigment epithelial (RPE) cells plated onto collagen-coated and collagenase-treated tissue culture plates incubated overnight after plating. Following collagenase treatment, plates were treated with vehicle (PBS.

FIG. 4 shows that the CMPs and CMP-TC conjugates of the invention significantly accelerated the proliferation and network formation of RPE cells, vs. vehicle. FIG. 4a shows RPE cells plated onto collagen-coated plates that had been treated with collagenase and then with only vehicle (negative control), while FIG. 4b shows results with cells plated onto plates that had been treated with a CMP of the invention (Compound 3). The results demonstrate that Compound 3 induced significant acceleration of proliferation (i.e., greater cell density in the monolayer), and spreading, migration and network formation between adjacent RPE cells (FIG. 4b), vs. cells on vehicle-treated plates in which cells were less numerous, less spread on the plate, and showed a lower network formation between adjacent cells (FIG. 4a). These results suggest that the CMPs of the invention (e.g., Compound 3) promote the proliferation, migration and network formation in RPE cells in vitro.

Figure 5:
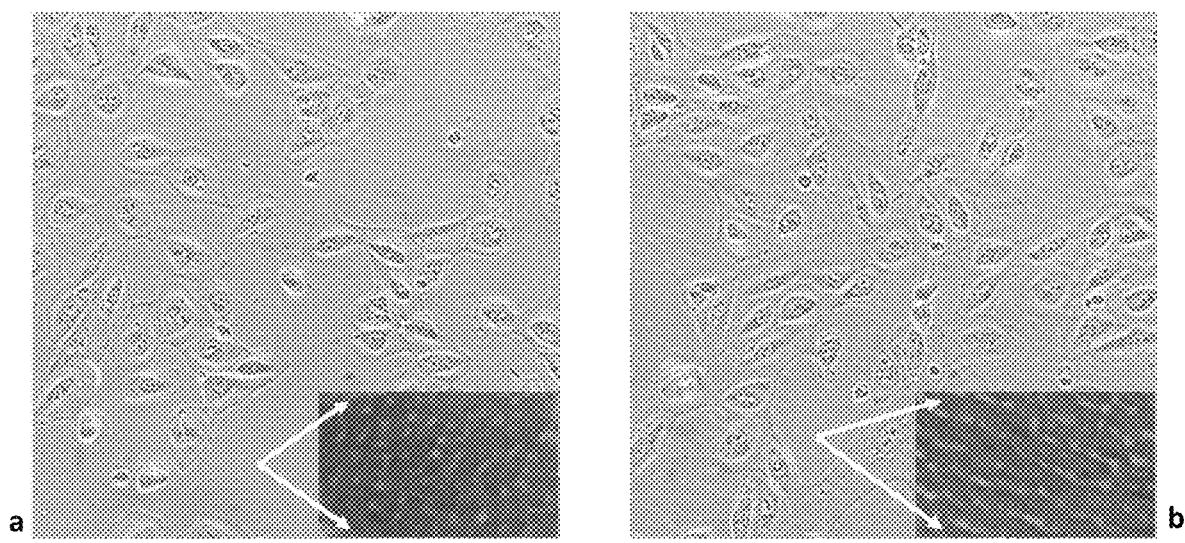
FIG. 5 depicts high-magnification DIC photomicrographs of the collagen-coated collagenase-treated plates from the experiment shown in FIG. 4.

To examine the impact of CMPs of the invention on the underlying collagen matrix in the experiments shown in FIG. 4, collagenase-treated collagen-coated plates (prepared as outlined above) were examined by differential interference contrast (DIC) microscopy. As shown in FIG. 5, high-magnification DIC photomicrographs demonstrated that the underlying collagen matrix on the vehicle-treated plates (FIG. 5a) formed a matrix of randomly oriented collagen fibers (arrows), while the collagen matrix on plates treated with Compound 3 (FIG. 5b) formed fibers that showed a parallel orientation (arrows) similar to what is observed in the stromal matrix in endogenous tissues in the absence of injury. These results with Compound 3 are also analogous to those reported in the literature in other in vitro systems (Kivanany, P B et al., J. Funct. Biomater. 9(4):54 (2018); Hapach, L A et al., Phys. Biol. 12(6): 061002 (2015); Lanfer, B. et al, Biomaterials 29:3888-3895 (2008); Saeidi, N et al., Biomaterials 30:6581-6592 (2009)).

Figure 6:
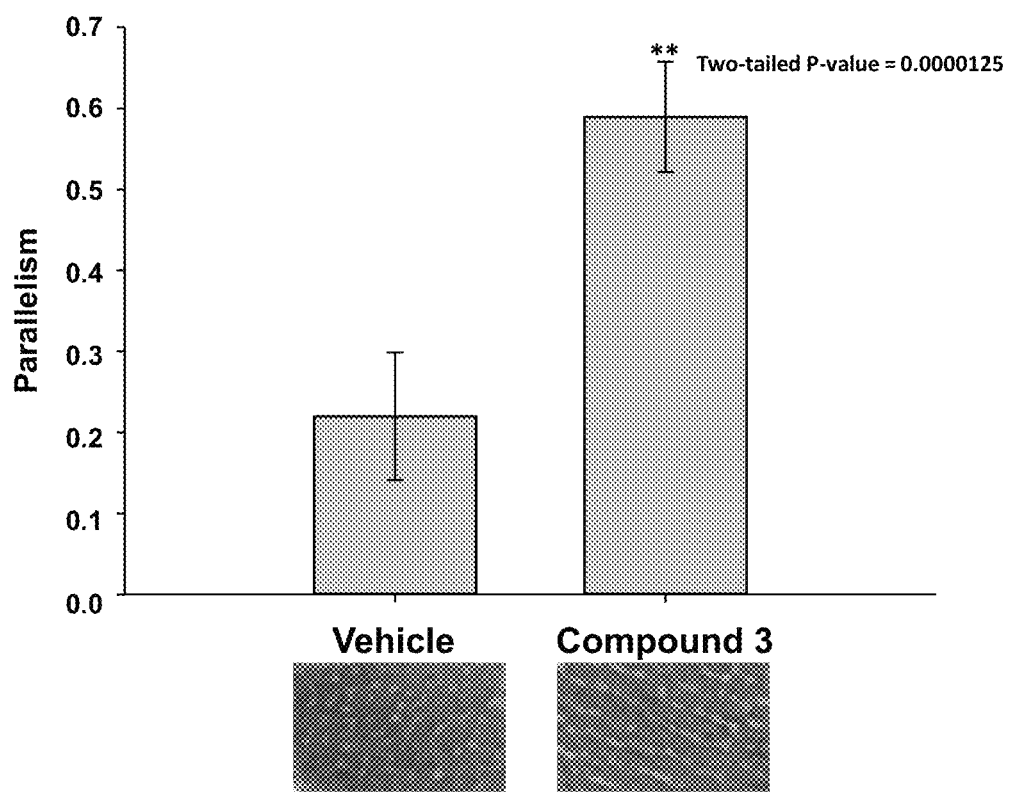
FIG. 6 is a bar graph depicting the degree of parallel (i.e., uni-directional) orientation of collagen observed in collagen-coated collagenase-treated plates from FIGS. 4 and 5, treated with either PBS (vehicle) or Compound 3, quantitated using digital analysis of the micrographs shown in FIG. 5 and underlying the bar graph.

Based on the results shown in FIG. 5, and the analogous reports in the literature, the degree of parallel (i.e., unidirectional) orientation of collagen observed in plates treated with a CMP of the invention (Compound 3) was quantitated using digital analysis of the micrographs shown in FIG. 5 based on an algorithm recently reported in the literature (Cooper, M L et al., Acta Neuropathol. Commun. 6(1):38 (2018)). Results of this analysis (FIG. 6) showed that treatment of the collagenase-treated collagen coated plates with Compound 3 improved collagen parallel alignment by about threefold compared to what was observed on vehicle-treated plates. Together with the results shown in FIG. 5, these results demonstrate that a CMP of the invention (viz., Compound 3) was able to rapidly induce formation of organized collagen fibers in the in vitro matrix, analogous to what is observed in uninjured and healed tissues in vivo.

Figure 7:
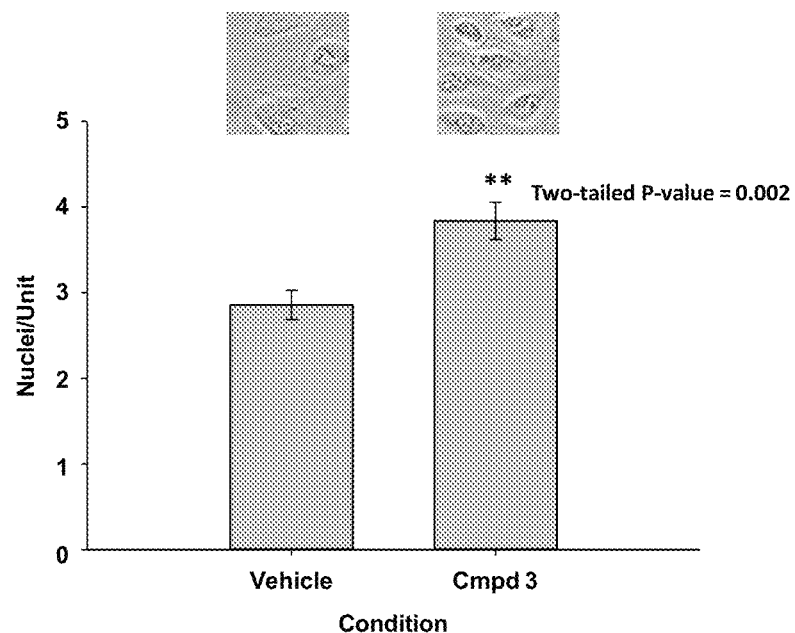
FIG. 7 is a bar graph (and corresponding photomicrographs) of the number of RPE cell nuclei per unit area for cells plated onto on culture plates treated with either vehicle (PBS.

To examine the potential of CMPs of the invention to promote proliferation of RPE cells, ARPE19 cells cultured on collagenase-treated collagen-coated plates as described above were examined by phase contrast microscopy for density on the plate surfaces. Plates were divided into grids of set unit area (15 µm×15 µm), and the number of cell nuclei in each grid was determined for vehicle-treated and CMP (Compound 3)-treated plates. As shown in FIG. 7, RPE cells cultured on CMP-treated plates (FIG. 7b) were present in a significantly higher number per unit of plate area than those cells on vehicle-treated plates (FIG. 7a). These results indicate that Compound 3 promotes the proliferation in vitro of RPE cells.

Figure 8:
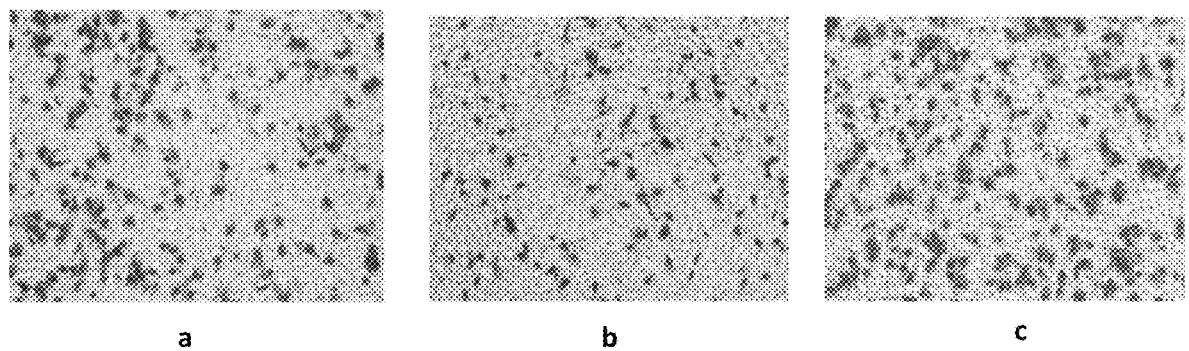
FIG. 8 is a series of photomicrographs of the underside of crystal-violet stained tissue culture membrane inserts coated with vehicle (water.
Figure 9:
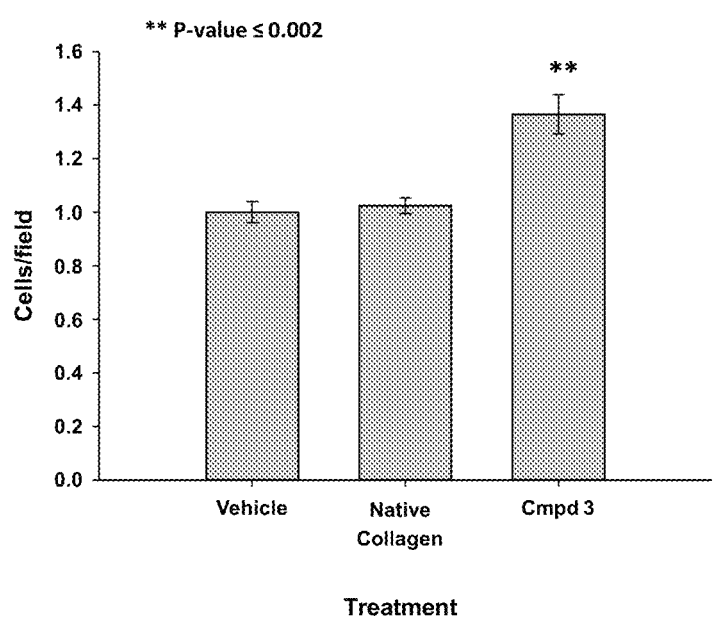
FIG. 9 is a bar graph of the number of cells migrating through and adhering to the basal side of the membranes from FIG. 8, determined by microscopically counting cells within 10× and 20× magnification fields, six fields per membrane insert.

CMPs of the invention were also examined for ability to induce migration and adherence of RPE cells in an in vitro assay, as a model of RPE cell migration and adherence occurring in healing in certain back-of-eye diseases (e.g., macular degeneration, retinitis pigmentosa) and retinal injuries. Transwell insert membranes (Costar; 8 μm pore size) were submersion coated with 500 μL of substrate (100 μg/ml human Type I collagen or 100 μg/ml Compound 3) or immersed in vehicle (water) at room temperature overnight. After 24 hours, insert membranes were washed three times with PBS and allowed to dry at 37° C. Approximately 105 ARPE19 cells for each condition were resuspended in 100 μL serum-free medium and added to the apical side of each insert membrane. The inserts were then placed into a 24-well plate containing 0.5 mL of complete medium (plus 10% FBS), which attracts cells and promotes migration, and plates incubated at 37° C. for 4 hours. An assessment was then done of how well the membrane coating allowed migration of the cells and promoted their adherence to the basal side of the membrane. Following incubation, non-migrated cells on the top of the insert were carefully removed with a cotton swab. Cells adhering to the basal side of the membrane following migration were fixed with 4% paraformaldehyde for 5 mins at room temperature, stained with 0.1% crystal violet solution for 5 mins, and then washed gently with water. The number of cells migrating through and adhering to the basal side of the membranes coated under the various conditions noted above was then determined by microscopically counting cells within 1× and 20× magnification fields, six fields per membrane insert. All experiments were done in duplicate. Qualitative results (FIG. 8) demonstrated that on membranes treated with a CMP of the invention, Compound 3, more RPE cells migrated across the membrane and adhered to the basal side of the membrane (FIG. 8c), both compared to vehicle (FIG. 8a) and native collagen (FIG. 8b). These qualitative results were supported quantitatively as well (FIG. 9), where Compound 3 was found to significantly increase migration and adherence of RPE cells vs. both vehicle and native collagen.

Figure 10:
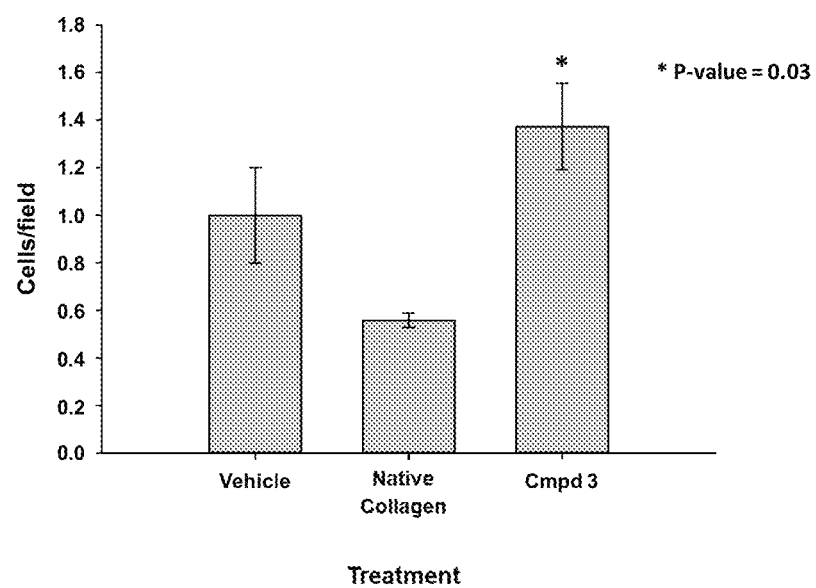
FIG. 10 is a bar graph demonstrating a repeat of the experiment depicted in FIGS. 8 and 9, except that only the apical surfaces of the transwell membrane were coated with vehicle, native human Type I collagen or Compound 3. Cells were then plated, incubated and allowed to migrate, and quantitated as described in FIG. 9.

In a related experiment to examine cellular migration, only the apical surface of the transwell membrane was coated (with 50 μL of solution) with either vehicle, native human Type I collagen (100 μg/mL) or Compound 3 (200 μM). Other conditions were the same as described above. Results of this experiment (FIG. 10) demonstrated that Compound 3 significantly increased migration of RPE cells through the membrane, compared to native Type I collagen. Vehicle and compound 3 were equivalently effective in allowing passage, which indicates that compound 3 provides a substrate for RPE cell migration without also providing the barrier to migration that is provided by natural collagen. These results demonstrate that the CMPs of the invention, and particularly Compound 3, induce migration and adherence of RPE cells in vitro, which provides a useful model of the migration and adherence of RPE cells in vivo in areas of collagen damage accompanying retinal epithelial disruption.

Taken together, these results support the use of the CMPs and CMP-TC conjugates of the present invention in promoting retinal epithelial healing and stromal collagen repair in mammalian retinal epithelial cell lines, a model of a variety of human and veterinary animal back-of-eye conditions including macular degeneration (dry, wet and age-related), retinitis pigmentosa, and other eye disorders, diseases, injuries and conditions involving the retinal epithelium.

Example 3: Effect of CMPs on Adherence of Retinal Pigment Epithelial Cells to Disrupted Collagen Matrices The inventors wished to further examine the possible therapeutic effects of CMPs and CMP-TC conjugates of the invention in back-of-eye indications, particularly in indications in which the collagen matrix may be disrupted. Therefore, studies were designed to test certain CMPs and CMP-TC conjugates in an in vitro setting—the adherence of retinal pigment epithelial (RPE) cells to tissue culture plates in vitro that were collagen-coated and that had been treated with a collagen-disrupting enzyme and then with a CMP of the invention, as a model of a disrupted and then potentially repaired matrix in vivo.

Figure 11:
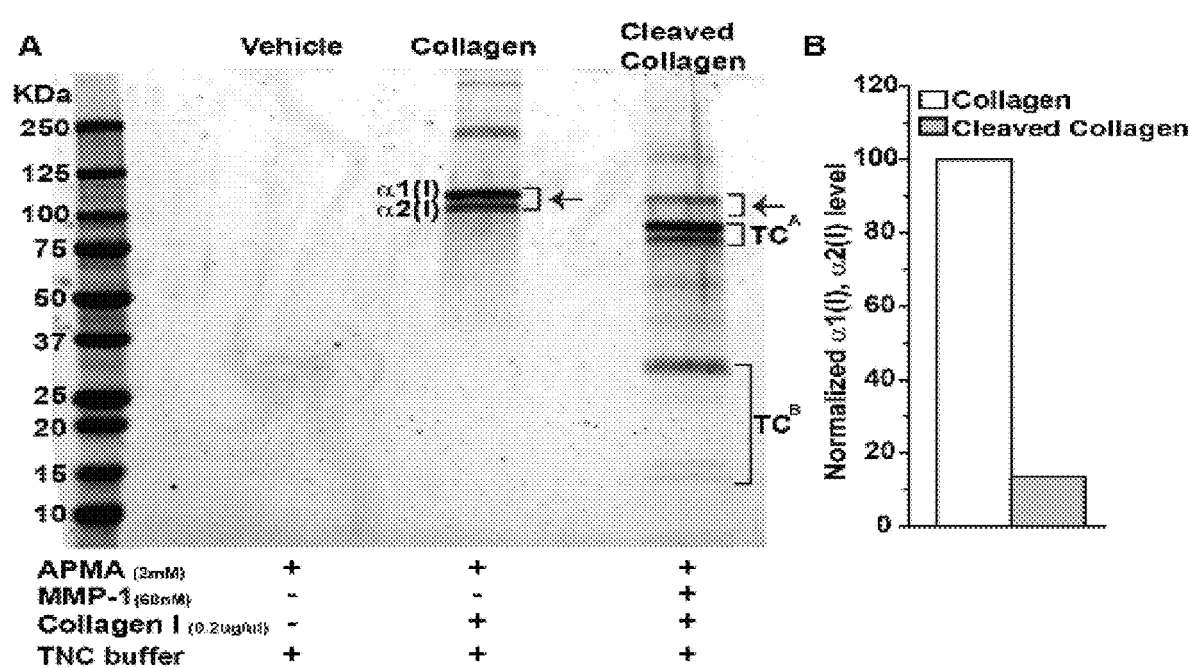
FIG. 11 demonstrates the cleavage of type I collagen by matrix metalloproteinase 1 (MMP-1) in an in vitro assay.

To test the ability of the selected enzyme (matrix metalloproteinase-1 (MMP-1)) to digest the collagen being used in the in vitro assays, 60 nM MMP-1 was activated with 2 mM APMA for 30 minutes at 37° C. in TNC buffer. Human type 1 atelo-collagen (3.375 μg, 0.2 μg/μl) was then added to the reaction and digested for additional 6h at 37° C. The reaction was then subjected to SDS-PAGE under reducing conditions. Results are shown in FIG. 11. As seen in FIG. 11A, the α1 and α2 components of type I collagen were resolved in the gel, and treatment of the collagen with MMP-1 (to form "Cleaved Collagen") demonstrated significant digestion of these components into lower molecular weight fragments ($TC^A$ and $TC^B$). As shown in FIG. 11B, quantitation of the digestion, normalized to the α1 and α2 bands shown in the undigested collagen samples, demonstrated an approximately 7.4-fold (over 80%) reduction in the full length of these chains when collagen was treated with MMP-1. These results validate the ability of MMP-1 to cleave collagen for use in the in vitro assays of this Example. These results also are in line with previous reports that MMP-1 unwinds triple-helical type I collagen prior to the hydrolysis of the peptide bonds by the enzyme (see Chung L. et al., EMBO J. 23(15):3020-3030 (2004)).

For cellular assays, ARPE19 cells (see Example 2) were plated onto tissue culture plates that had been coated with intact collagen or with MMP-1-digested collagen. MMP-1 was activated using APMA as described above. For testing "cut collagen", human type I atelocollagen was for digested with activated MMP-1 as described above, and tissue culture plates were then coated overnight with intact human type I atelocollagen or with cut collagen. Plates were then treated with vehicle (PBS) or with one of four different CMPs of the invention: CMP A (SEQ ID NO:3), CMP B (SEQ ID NO:6), CMP C (SEQ ID NO:391) or CMP D (SEQ ID NO:13), each at 100 μM, 100 μL per well, and incubated at 37° C. for five hours. Plates were then rinsed with culture medium, and ARPE-19 cells were plated uniformly on plates having one of three surface coating conditions: (1) intact collagen; (2) cut collagen; and (3) cut collagen+CMP. Plates were then incubated at 37° C. for 19 hours, and then examined for cell adherence by phase contrast microscopy. Representative results are shown in FIGS. 12-13.

Figure 12:
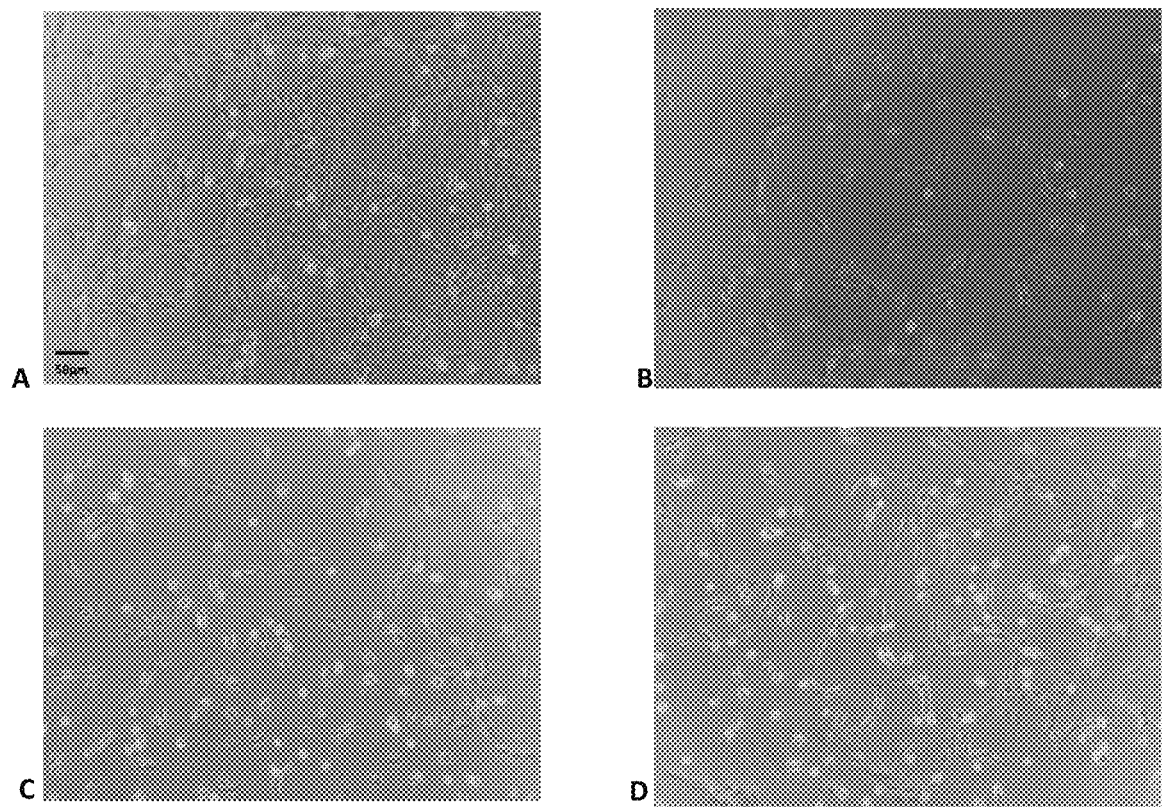
FIG. 12 is a series of phase contrast photomicrographs of retinal pigment epithelial (RPE) cells (ARPE-19 cell line) plated onto tissue culture plates that had been coated overnight with type I collagen ("Collagen"
Figure 13:
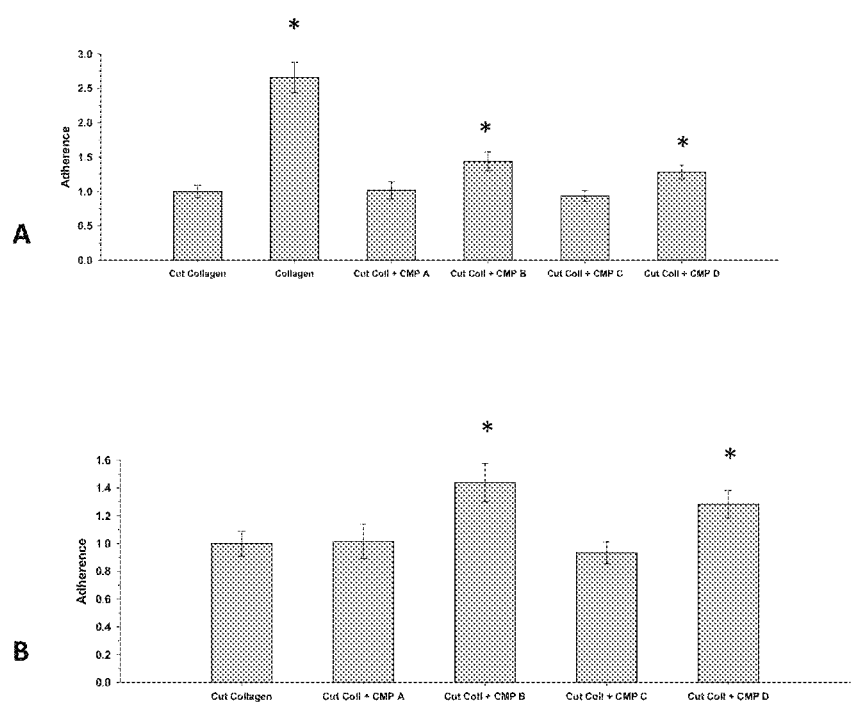
FIG. 13 is a bar graph of the amount of cellular adherence of RPE cells observed under the various conditions described and depicted in FIG. 12, including treatment with CMPs A (SEQ ID NO:3), B (SEQ ID NO:6), C (SEQ ID NO:391) or D (SEQ ID NO:13). All data were normalized to the adherence observed in "Cut Collagen" replicates. *: $p \leq 0.005$ vs. Cut Collagen.

FIG. 12 shows that RPE cells adhered quite readily to collagen-coated plates (FIG. 12A), but not very well to plates coated with cut collagen (FIG. 12B). However, certain CMPs of the invention were apparently able to repair the collagen matrix on the plate to a certain extent such that RPE cells demonstrated increased adherence, at a higher level than seen in the cut collagen plates. For example, in the photomicrographs, cells plated onto plates coated with cut collagen that had been treated with CMP B (SEQ ID NO:6) showed increased adherence vs. cut collagen plates (FIG. 12D); this propensity to increase adherence was less pronounced on plates coated with cut collagen and treated with CMP A SEQ ID NO:3), however, as seen in FIG. 12C. Quantitative assays of adherence of cells on cut collagen plates treated with four different CMPs confirmed these results (FIG. 13A, 13B), in that both CMP B and CMP D (SEQ ID NO:13) demonstrated significantly increased adhesion, and therefore presumably significantly enhanced ability to repair the digested collagen matrix on the plates, compared with cut collagen and with CMP A and CMP C (SEQ ID NO:391). These results provide a cell-based correlation with the DIC microscopy results in Example 2 that demonstrated the impact of CMP treatment on reformation of a disrupted collagen matrix in vitro, and suggest that certain CMPs of the invention may be useful in enhancing the repair of a disrupted collagen matrix to thereby promote adherence, proliferation, migration and network formation in RPE cells in vitro and perhaps neuronal cells in general.

Example 4: Effect of CMPs on Neurite Outgrowth in Dorsal Root Ganglion Cells In Vitro The inventors wished to further examine the possible therapeutic effects of CMPs and CMP-TC conjugates of the invention in neuronal and nervous system indications, particularly in indications in which the collagen matrix may be disrupted. Therefore, studies were designed to test certain CMPs and CMP-TC conjugates in another in vitro setting—the survival of and neurite outgrowth in dorsal root ganglia (DRG) neurons in vitro.

For these assays, DRG neurons were isolated from day 19 embryonic rats and plated onto tissue culture plates that had been coated with intact collagen or with MMP-1-digested collagen and then treated with vehicle (PBS) or with one of four different CMPs of the invention: CMP A (SEQ ID NO:3), CMP B (SEQ ID NO:6), CMP C (SEQ ID NO:391) or CMP D (SEQ ID NO:13), each at 100 μM, 100 μL per well, and incubated at 37° C. for five hours. Plates were then rinsed with culture medium, and DRG neuronal cells were plated uniformly on plates having one of three surface coating conditions: (1) intact collagen; (2) cut collagen; and (3) cut collagen+CMP. Plates were then incubated at 37° C. for 48 hours, and then examined for morphology and neurite outgrowth by inverted brightfield microscopy. Representative results are shown in FIGS. 14-15.

Figure 14:
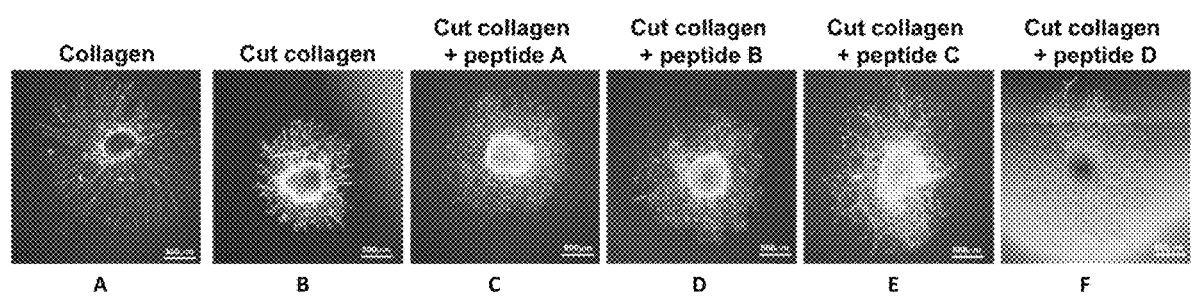
FIG. 14 is a series of inverted brightfield photomicrographs of dorsal root ganglia (DRG) neurons plated onto tissue culture plates that had been coated overnight with type I collagen ("Collagen"
Figure 15:
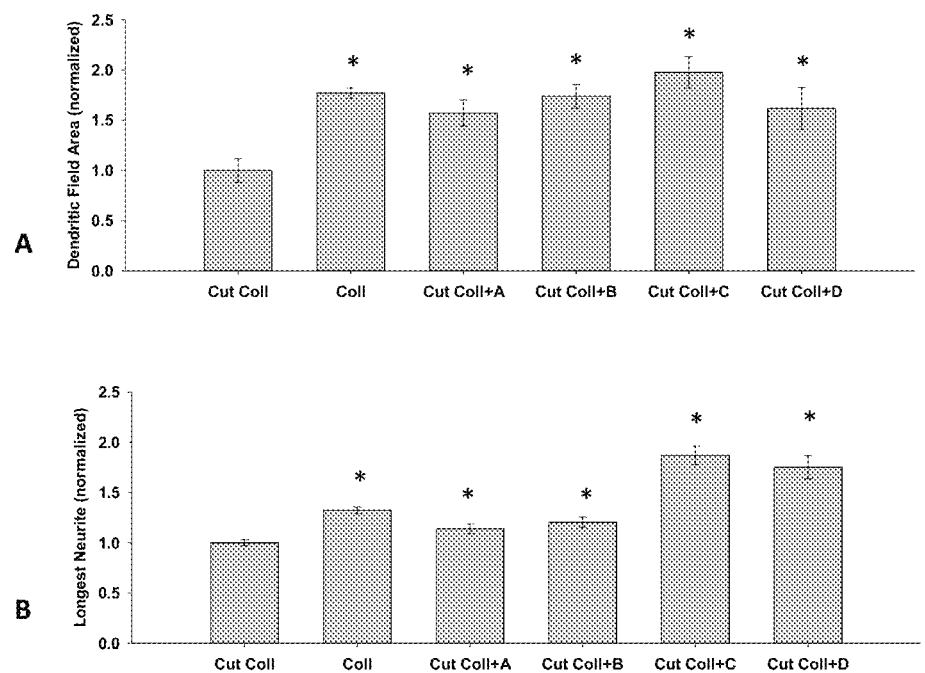
FIG. 15 is a bar graph of the size of the field of dendrite outgrowth ("dendritic field area"

FIG. 14 shows that DRG neurons demonstrated substantial neurite outgrowth in all directions from the cell body when plated onto collagen-coated plates (FIG. 14A), but reduced neurite outgrowth on plates coated with cut collagen (FIG. 14B). However, the CMPs of the invention were apparently able to repair the collagen matrix on the plate to a certain extent such that DRG neurons demonstrated substantial neurite outgrowth well above what was seen on the cut collagen plates, with certain CMPs inducing neurite outgrowth to an extent similar to or even greater than that seen with intact, undigested collagen (FIGS. 14C-14F). When quantitating the area of the dendritic field normalized to that observed on the cut collagen plates (FIG. 15A), all CMPs tested did not differ significantly (p=0.15) from what was observed on the intact collagen plates. Moreover, as shown in FIG. 15B, the length of the longest neurite observed (normalized to cut collagen) on plates treated with CMP C (SEQ ID NO:391) and CMP D (SEQ ID NO:13) even exceeded that observed with intact collagen (p≤0.002). These results provide a primary neuronal cell-based correlation with the RPE cell results in Examples 2 and 3 that demonstrated the impact of CMP treatment on reformation of a disrupted collagen matrix in vitro, and indicate that certain CMPs of the invention are useful in enhancing the repair of a disrupted collagen matrix to thereby promote the proliferation, migration and network formation in neuronal cells. Together, these results suggest that the CMPs of the present invention should prove useful in treating, ameliorating, preventing and diagnosing a variety of diseases and disorders involving nerve cells and the nervous system.

Example 5: Penetration of CMPs from Ocular Surface to Retina

The inventors wished to further examine the possible therapeutic effects of CMPs and CMP-TC conjugates of the invention in back-of-eye indications, particularly in indications in which the collagen matrix may be disrupted. In treating certain such indications, it is desirable to be able to apply the therapeutic composition dropwise to the ocular surface rather than having the patient undergo the more invasive procedure of intravitreal injection; such dropwise addition of therapeutics to the eyes are easily accomplished by patients in their home settings rather than in the physician's office as is required for intravitreal injection, resulting in better patient comfort and compliance with the therapeutic regimen. Therefore, studies were designed to test the ability of certain CMPs to penetrate through the cornea to the retina in an in vivo setting, intact mouse eyes.

Figure 16:
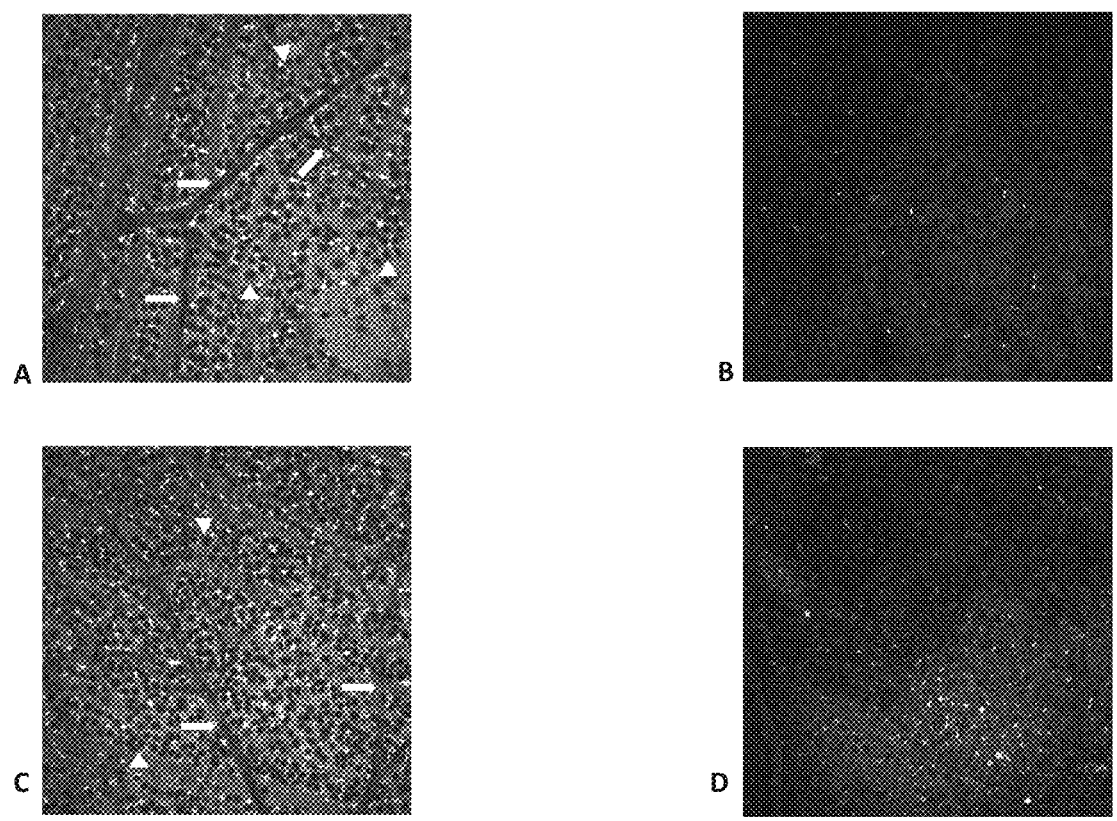
FIG. 16 is a series of confocal fluorescence photomicrographs of mouse eyes that had received intravitreous injection (FIG. 16A, 16B) or dropwise ocular surface application (FIG. 16C, 16D) of a solution of a Tide Fluor™2-conjugated (Pro-Pro-Gly)$_7$ (SEQ ID NO:1) CMP ("TF2-CMP"). Mice were sacrificed on day 3 after surface application of TF2-CMP, or on same day as intravitreal injection, and the localization of TF2-CMP was determined.

To test the ability of a CMP to penetrate from the surface of the eye to the back of the eye, a fluorophore-conjugated CMP was prepared. In these studies, a CMP having the amino acid sequence (Pro-Pro-Gly)$_7$ (SEQ ID NO:1) was conjugated at its C terminus with Tide Fluor™ 2 (AAT Bioquest, Sunnyvale, Calif.) and obtained from Bachem (Torrance, Calif.); this fluorescent conjugate is designated herein as "TF2-CMP." Female mice (8-week-old C57BL/6) were anesthetized, and TF2-CMP was administered to both eyes of the mice either in the form of drops administered to the surface of the eyes (bilaterally, once per day for three days, 10 μL of a 200 μM solution of TF2-CMP in PBS per administration) or to the back of the eye via intravitreal injection as positive controls (bilaterally, one injection only on day 3, using pulled glass needles for the injection; 1.5 μL of a 100 μM solution of TF2-CMP in PBS per injection). Negative control mice were treated with vehicle only (PBS). On day 3, mice were sacrificed and the amount of fluorescence in various portions of the eye structure (indicative of the amount of TF2-CMP) was qualitatively examined via confocal fluorescence photomicrography. Results are depicted in FIG. 16.

As expected, intravitreal injection of TF2-CMP (FIGS. 16A and 16B) demonstrated highly directed binding of the CMP at and around ganglion cell neurons in the ganglion cell layer of the retina (FIG. 16A), with numerous blood vessels (arrows) and ganglion cell nuclei (arrowheads) clearly visible in contrast. The fluorescence was seen to be localized in the ganglion cell layer, with very little of the TF2-CMP localized to the inner limiting membrane of the vitreous surface (FIG. 16B). Surprisingly, similar results were observed in mouse eyes in which the TF2-CMP had been administered dropwise over three days to the eye surface (FIGS. 16C and 16D). In these eyes, the fluorescence was also directed around the ganglion cell neurons in the retinal ganglion cell layer (FIG. 16C), with numerous blood vessels (arrows) and ganglion cell nuclei (arrowheads) again visible in contrast. The amount of non-specific fluorescence observed in the vitreous surface (FIG. 16D) was somewhat higher than that observed for intravitreal injection (FIG. 16B), perhaps indicating that some of the TF2-CMP was retained within the inner limiting membrane of the vitreous surface or was in the process of traversing that membrane into the ganglion cell layer.

These results demonstrate that the CMPs and CMP conjugates of the invention are able to penetrate from the ocular surface through the cornea and to the retina, and more specifically through the inner limiting membrane of the retina to the ganglion cell layer. The CMPs are also seen to be present in the interstitial space and/or on the cell surfaces, with no penetration to the ganglion cell nuclei nor across the basement membrane of retinal blood vessels. Together, these results indicate that dropwise administration of the CMPs and CMP-conjugates of the invention give penetration results that are at least highly similar to direct intravitreal injection of the compositions. These results support the conclusion that a more patient-friendly and patient-compliant approach to treating posterior segment ocular diseases and disorders, using dropwise administration of the CMPs and CMP-conjugates of the invention rather than more invasive procedures such as intravitreal injection, may be achievable.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed. For example, the recitation of a range of values (e.g., a range of dosages or dosing concentrations) should be understood to include the values at the beginning and the end of that range, as well as every value in between those beginning and end values. To illustrate this concept, a range of "about 25 ng/ml to about 250 ng/ml" should be interpreted to include a value that is "about 25 ng/ml," "about 250 ng/ml," and every individual concentration value between those two values. The term "about" when used in conjunction with a numeric value typically means a value that is the actual value recited 10% of that value.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Hence, in addition to those specifically described herein, other suitable embodiments of the invention will be readily apparent to one of ordinary skill in the art based upon the foregoing description and examples, and upon knowledge generally available in the relevant arts. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

All references cited herein, including U.S. patents and published patent applications, international patents and patent applications, and journal references or other publicly available documents, are incorporated herein by reference in their entireties to the same extent as if each reference had been specifically cited for the portion or portions of such reference applicable to the section of this application to which it is relevant.

---

What is claimed is:

1. A method of treating a posterior segment disease, disorder or wound, a paraocular disease, disorder or medical condition, an extraocular disease, disorder or medical condition, or an anterior segment ocular disease, disorder or wound, in a human or veterinary animal suffering from or predisposed to said ocular disease, disorder or wound, comprising administering a composition comprising (a) at least one collagen mimetic peptide (CMP) comprising the amino acid sequence of SEQ ID NO: 6, and (b) one or more pharmaceutically suitable carriers to an eye of said human or veterinary animal in a dosage sufficient to treat said posterior segment ocular disease, disorder or wound, monitoring the condition of the eye in said human or veterinary animal over time, and readministering said composition to the eye until said posterior segment ocular disease, disorder or wound is treated or ameliorated.

2. The method of claim 1, wherein said posterior segment ocular disease, disorder or wound involves the retina, retinal blood vessels, retinal nerves or optic nerve.

3. The method of claim 2, wherein said posterior segment ocular disease or disorder involves the retinal epithelium.

4. The method of claim 2, wherein said posterior segment ocular disease or disorder is selected from the group consisting of macular degeneration, retinitis pigmentosa, a retinal tear, retinal detachment, retinopathy, retinal arterial or venous occlusion, optic neuritis, optic neuropathy and optic atrophy.

5. The method of claim 4, wherein said macular degeneration is selected from wet macular degeneration, dry macular degeneration and age-related macular degeneration.

6. The method of claim 4, wherein said retinopathy is diabetic retinopathy.

7. The method of claim 1, wherein said composition is administered to the eye conjunctivally or subconjunctivally.

8. The method of claim 7, wherein said subconjunctival administration is achieved by administering said composition into the subconjunctival fornix.

9. The method of claim 1, wherein said composition is administered to the eye in the form of one or more drops of solution or a suspension that contains the composition.

10. The method of claim 1, wherein said composition is administered to the eye via injection.

11. The method of claim 1, wherein said composition is administered to the eye in the form of a coating on a solid material that is implanted into an eye structure.

12. The method of claim 1, wherein said composition is administered to the eye in the form of a wafer, film, gel, mesh or patch.

13. The method of claim 1, wherein said composition is attached to one or more spheres or nanoparticles that are delivered to or into an eye structure.

* * * * *

SEQUENCE LISTING

```
<160> NUMBER OF SEQ ID NOS: 419

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4S-hydroxyproline
```

```
<220> FEATURE:
<221> NAME/KEY: MOD_RES
<222> LOCATION: (4)..(4)
<223> OTHER INFORMATION: 4S-hydroxyproline
<220> FEATURE:
<221> NAME/KEY: MOD_RES
<222> LOCATION: (7)..(7)
<223> OTHER INFORMATION: 4S-hydroxyproline
<220> FEATURE:
<221> NAME/KEY: MOD_RES
<222> LOCATION: (10)..(10)
<223> OTHER INFORMATION: 4S-hydroxyproline
<220> FEATURE:
<221> NAME/KEY: MOD_RES
<222> LOCATION: (13)..(13)
<223> OTHER INFORMATION: 4S-hydroxyproline
<220> FEATURE:
<221> NAME/KEY: MOD_RES
<222> LOCATION: (16)..(16)
<223> OTHER INFORMATION: 4S-hydroxyproline
<220> FEATURE:
<221> NAME/KEY: MOD_RES
<222> LOCATION: (19)..(19)
<223> OTHER INFORMATION: 4S-hydroxyproline

<400> SEQUENCE: 2

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 4S-hydroxyproline
<220> FEATURE:
<221> NAME/KEY: MOD_RES
<222> LOCATION: (5)..(5)
<223> OTHER INFORMATION: 4S-hydroxyproline
<220> FEATURE:
<221> NAME/KEY: MOD_RES
<222> LOCATION: (8)..(8)
<223> OTHER INFORMATION: 4S-hydroxyproline
<220> FEATURE:
<221> NAME/KEY: MOD_RES
<222> LOCATION: (11)..(11)
<223> OTHER INFORMATION: 4S-hydroxyproline
<220> FEATURE:
<221> NAME/KEY: MOD_RES
<222> LOCATION: (14)..(14)
<223> OTHER INFORMATION: 4S-hydroxyproline
<220> FEATURE:
<221> NAME/KEY: MOD_RES
<222> LOCATION: (17)..(17)
<223> OTHER INFORMATION: 4S-hydroxyproline
<220> FEATURE:
<221> NAME/KEY: MOD_RES
<222> LOCATION: (20)..(20)
<223> OTHER INFORMATION: 4S-hydroxyproline

<400> SEQUENCE: 3

Pro Pro Gly Pro Pro Gly Pro Pro Gly Pro Pro Gly Pro Pro Gly Pro
1               5                   10                  15

Pro Gly Pro Pro Gly
            20
```

```
<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (19)..(19)
<223> OTHER INFORMATION: Fluoroproline

<400> SEQUENCE: 4

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
```

<223> OTHER INFORMATION: Fluoroproline

<400> SEQUENCE: 5

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 6

Pro Pro Gly Pro Pro Gly Pro Pro Gly Pro Pro Gly Pro Pro Gly Pro
1               5                   10                  15

Pro Gly Pro Pro Gly
         20

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (19)..(19)
<223> OTHER INFORMATION: Chloroproline

<400> SEQUENCE: 7

Pro Pro Gly Pro Pro Gly Pro Pro Gly Pro Pro Gly Pro Pro Gly Pro
1               5                  10                  15

Pro Gly Pro Pro Gly
         20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 8

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

```
<400> SEQUENCE: 9

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 11

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
```

```
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 12

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 13

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 14

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Pro Gly Pro Pro Gly Pro Pro Gly Pro Pro Gly Pro Pro Gly Pro
1               5                   10                  15

Pro Gly Pro Pro Gly
            20

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Pro Gly Cys Pro Gly Pro Pro Gly Pro Pro Gly Pro Pro Gly Pro
1               5                   10                  15
```

-continued

Pro Gly Pro Pro Gly
            20

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 22

Pro Pro Gly Pro Pro Gly Pro Pro Gly Pro Gly Cys Pro Gly Pro
1               5                   10                  15

Pro Gly Pro Pro Gly
            20

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Pro Gly Pro Pro Gly Pro Pro Gly Pro Gly Pro Cys Gly Pro
1               5                   10                  15

Pro Gly Pro Pro Gly
            20

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Pro Pro Gly Pro Pro Gly Pro Pro Gly Pro Pro Gly Pro Pro Gly Pro
1               5                   10                  15

Cys Gly Cys Pro Gly
            20

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Pro Gly Pro Pro Gly Pro Pro Gly Pro Pro Gly Pro Pro Gly Pro
1               5                   10                  15

Pro Gly Cys Pro Gly
            20

```
<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 28

Cys Pro Gly Pro Pro Gly Pro Pro Gly Pro Pro Gly Pro Pro Gly Pro
1               5                   10                  15

Pro Gly Pro Pro Gly
            20

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
```

```
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 29

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 30

Pro Pro Gly Cys Pro Gly Pro Pro Gly Pro Pro Gly Pro Pro Gly Pro
1               5                   10                  15

Pro Gly Pro Pro Gly
            20

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
```

```
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 31

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 32

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 33
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 33

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 34

Pro Pro Gly Pro Pro Gly Pro Pro Gly Pro Cys Gly Pro Pro Gly Pro
1               5                   10                  15
```

Pro Gly Pro Pro Gly
        20

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 35

Pro Pro Gly Pro Pro Gly Pro Pro Gly Pro Pro Gly Cys Pro Gly Pro
1               5                   10                  15

Pro Gly Pro Pro Gly
        20

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)

<223> OTHER INFORMATION: Hydroxyproline

<400> SEQUENCE: 36

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 37

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline

```
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 38

Pro Pro Gly Pro Pro Gly Pro Pro Gly Pro Pro Gly Pro Pro Gly Pro
1               5                   10                  15

Cys Gly Pro Pro Gly
            20

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline

<400> SEQUENCE: 39

Pro Pro Gly Pro Pro Gly Pro Pro Gly Pro Pro Gly Pro Pro Gly Pro
1               5                   10                  15

Pro Gly Cys Pro Gly
            20

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
```

```
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 40

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 41

Cys Pro Gly Pro Pro Gly Pro Pro Gly Pro Pro Gly Pro Pro Gly Pro
1               5                   10                  15

Pro Gly Pro Pro Gly
            20

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 42

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 43

Pro Pro Gly Cys Pro Gly Pro Pro Gly Pro Pro Gly Pro Pro Gly Pro
1               5                   10                  15

Pro Gly Pro Pro Gly
            20

<210> SEQ ID NO 44
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 44

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 45

Pro Pro Gly Pro Pro Gly Cys Pro Gly Pro Pro Gly Pro Pro Gly Pro
1               5                   10                  15
```

Pro Gly Pro Pro Gly
            20

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 46

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES -continued

```
<222> LOCATION: (20)..(20)
<223> OTHER INFORMATION: Hydroxyproline

<400> SEQUENCE: 47

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 48

Pro Pro Gly Pro Pro Gly Pro Pro Gly Pro Gly Cys Pro Gly Pro
1               5                   10                  15

Pro Gly Pro Pro Gly
            20

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
```

<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 49

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 50

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline

```
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 51

Pro Pro Gly Pro Pro Gly Pro Pro Gly Pro Pro Gly Pro Pro Gly Pro
1               5                   10                  15

Cys Gly Pro Pro Gly
            20

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 52

Pro Pro Gly Pro Pro Gly Pro Pro Gly Pro Pro Gly Pro Pro Gly Pro
1               5                   10                  15

Pro Gly Cys Pro Gly
            20

<210> SEQ ID NO 53
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline

<400> SEQUENCE: 53

Pro Pro Gly Pro Pro Gly Pro Pro Gly Pro Pro Gly Pro Pro Gly Pro
1               5                   10                  15
Pro Gly Pro Cys Gly
            20

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 54

Cys Pro Gly Pro Pro Gly Pro Pro Gly Pro Pro Gly Pro Pro Gly Pro
1               5                   10                  15
Pro Gly Pro Pro Gly
            20

<210> SEQ ID NO 55
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 55

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 56

Pro Pro Gly Cys Pro Gly Pro Pro Gly Pro Pro Gly Pro Pro Gly Pro
```

```
1               5                   10                  15
Pro Gly Pro Pro Gly
            20

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 57

Pro Pro Gly Pro Cys Gly Pro Pro Gly Pro Pro Gly Pro Pro Gly Pro
1               5                   10                  15
Pro Gly Pro Pro Gly
            20

<210> SEQ ID NO 58
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
```

```
<221> NAME/KEY: MOD_RES
<222> LOCATION: (20)..(20)
<223> OTHER INFORMATION: Fluoroproline

<400> SEQUENCE: 58

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 59

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
```

```
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 60

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 61
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 61

Pro Pro Gly Pro Pro Gly Pro Pro Gly Pro Pro Gly Cys Pro Gly Pro
1               5                   10                  15

Pro Gly Pro Pro Gly
            20

<210> SEQ ID NO 62
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
```

```
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 62

Pro Pro Gly Pro Pro Gly Pro Pro Gly Pro Gly Pro Cys Gly Pro
1               5                   10                  15

Pro Gly Pro Pro Gly
            20

<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 63

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 64

Pro Pro Gly Pro Pro Gly Pro Pro Gly Pro Pro Gly Pro Pro Gly Pro
1               5                   10                  15

Cys Gly Pro Pro Gly
            20

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 65

Pro Pro Gly Pro Pro Gly Pro Pro Gly Pro Pro Gly Pro Pro Gly Pro
1               5                   10                  15

Pro Gly Cys Pro Gly
            20
```

```
<210> SEQ ID NO 66
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

<400> SEQUENCE: 66

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 67
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 67
```

-continued

```
Cys Pro Gly Pro Pro Gly Pro Pro Gly Pro Pro Gly Pro Pro Gly Pro
1               5                   10                  15

Pro Gly Pro Pro Gly
            20
```

<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 68

```
Pro Cys Gly Pro Pro Gly Pro Pro Gly Pro Pro Gly Pro Pro Gly Pro
1               5                   10                  15

Pro Gly Pro Pro Gly
            20
```

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

```
<220> FEATURE:
<221> NAME/KEY: MOD_RES
<222> LOCATION: (20)..(20)
<223> OTHER INFORMATION: Fluoroproline

<400> SEQUENCE: 69

Pro Pro Gly Cys Pro Gly Pro Pro Gly Pro Pro Gly Pro Pro Gly Pro
1               5                   10                  15

Pro Gly Pro Pro Gly
            20

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 70

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
```

```
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 71

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 72
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 72

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 73
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
```

```
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 73

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 74
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 74

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 75
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

```
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 75

Pro Pro Gly Pro Pro Gly Pro Pro Gly Pro Pro Gly Cys Pro Gly Pro
1               5                   10                  15

Pro Gly Pro Pro Gly
            20

<210> SEQ ID NO 76
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 76

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 77
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 77

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 78
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 78

Pro Pro Gly Pro Pro Gly Pro Pro Gly Pro Pro Gly Pro Pro Gly Pro
1               5                   10                  15
```

Cys Gly Pro Pro Gly
        20

<210> SEQ ID NO 79
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 79

Pro Pro Gly Pro Pro Gly Pro Pro Gly Pro Pro Gly Pro Pro Gly Pro
1               5                   10                  15

Pro Gly Cys Pro Gly
        20

<210> SEQ ID NO 80
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)

```
<223> OTHER INFORMATION: Fluoroproline

<400> SEQUENCE: 80

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 81

Cys Pro Gly Pro Pro Gly Pro Pro Gly Pro Pro Gly Pro Pro Gly Pro
1               5                   10                  15

Pro Gly Pro Pro Gly
            20
```

```
<210> SEQ ID NO 82
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 82

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 83
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 83

Pro Pro Gly Cys Pro Gly Pro Pro Gly Pro Pro Gly Pro Pro Gly Pro
1               5                   10                  15

Pro Gly Pro Pro Gly
            20

<210> SEQ ID NO 84
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
```

```
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 84

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 85
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
```

```
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 85

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
```

```
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 86

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 87
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
```

```
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 87

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 88
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline
```

<400> SEQUENCE: 88

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 89
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 89

Pro Pro Gly Pro Pro Gly Pro Pro Gly Pro Pro Gly Cys Pro Gly Pro
1               5                   10                  15

Pro Gly Pro Pro Gly
            20

```
<210> SEQ ID NO 90
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 90

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 91
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 91

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 92
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
```

```
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 92

Pro Pro Gly Pro Pro Gly Pro Pro Gly Pro Pro Gly Pro Pro Gly Pro
1               5                   10                  15

Cys Gly Pro Pro Gly
            20

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
```

```
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 93

Pro Pro Gly Pro Pro Gly Pro Pro Gly Pro Pro Gly Pro Pro Gly Pro
1               5                   10                  15

Pro Gly Cys Pro Gly
            20

<210> SEQ ID NO 94
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
```

```
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline

<400> SEQUENCE: 94

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 95

Cys Pro Gly Pro Pro Gly Pro Pro Gly Pro Pro Gly Pro Pro Gly Pro
1               5                   10                  15

Pro Gly Pro Pro Gly
            20

<210> SEQ ID NO 96
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 96

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 97
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 97

Pro Pro Gly Cys Pro Gly Pro Pro Gly Pro Pro Gly Pro Pro Gly Pro
1               5                   10                  15

Pro Gly Pro Pro Gly
            20
```

```
<210> SEQ ID NO 98
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 98

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 99
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline
```

<400> SEQUENCE: 99

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 100
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 100

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 101
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES

```
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 101

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 102
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 102

Pro Pro Gly Pro Pro Gly Pro Pro Gly Pro Pro Gly Cys Pro Gly Pro
1               5                   10                  15

Pro Gly Pro Pro Gly
            20

<210> SEQ ID NO 103
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
```

```
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 103

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 104
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 104

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 105
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
```

```
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 105

Pro Pro Gly Pro Pro Gly Pro Pro Gly Pro Pro Gly Pro Pro Gly Pro
1               5                   10                  15

Cys Gly Pro Pro Gly
            20

<210> SEQ ID NO 106
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 106

Pro Pro Gly Pro Pro Gly Pro Pro Gly Pro Pro Gly Pro Pro Gly Pro
1               5                   10                  15

Pro Gly Cys Pro Gly
            20

<210> SEQ ID NO 107
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline

<400> SEQUENCE: 107

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 108
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 108

Cys Pro Gly Pro Pro Gly Pro Pro Gly Pro Pro Gly Pro Pro Gly Pro
1               5                   10                  15

Pro Gly Pro Pro Gly
```

<210> SEQ ID NO 109
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 109

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 110
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 110

Pro Pro Gly Cys Pro Gly Pro Pro Gly Pro Pro Gly Pro Pro Gly Pro
1               5                   10                  15

Pro Gly Pro Pro Gly
            20

<210> SEQ ID NO 111
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 111

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 112
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:

```
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 112

Pro Pro Gly Pro Pro Gly Cys Pro Gly Pro Pro Gly Pro Pro Gly Pro
1               5                  10                  15

Pro Gly Pro Pro Gly
            20

<210> SEQ ID NO 113
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 113

Pro Pro Gly Pro Pro Gly Pro Cys Gly Pro Pro Gly Pro Pro Gly Pro
1               5                  10                  15

Pro Gly Pro Pro Gly
            20

<210> SEQ ID NO 114
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
```

```
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 114

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 115
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 115

Pro Pro Gly Pro Pro Gly Pro Pro Gly Pro Cys Gly Pro Pro Gly Pro
1               5                   10                  15

Pro Gly Pro Pro Gly
            20

<210> SEQ ID NO 116
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
```

```
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 116

Pro Pro Gly Pro Pro Gly Pro Pro Gly Pro Pro Gly Cys Pro Gly Pro
1               5                   10                  15

Pro Gly Pro Pro Gly
            20

<210> SEQ ID NO 117
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 117

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 118
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 118

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 119
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 119

Pro Pro Gly Pro Pro Gly Pro Pro Gly Pro Pro Gly Pro Pro Gly Pro
1               5                   10                  15

Cys Gly Pro Pro Gly
            20
```

```
<210> SEQ ID NO 120
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 120

Pro Pro Gly Pro Pro Gly Pro Pro Gly Pro Pro Gly Pro Pro Gly Pro
1               5                   10                  15

Pro Gly Cys Pro Gly
            20

<210> SEQ ID NO 121
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline

<400> SEQUENCE: 121
```

```
Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 122
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 122

Cys Pro Gly Pro Pro Gly Pro Pro Gly Pro Pro Gly Pro Pro Gly Pro
1               5                   10                  15

Pro Gly Pro Pro Gly
            20

<210> SEQ ID NO 123
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 123

Pro Cys Gly Pro Pro Gly Pro Pro Gly Pro Pro Gly Pro Pro Gly Pro
1               5                   10                  15

Pro Gly Pro Pro Gly
            20

<210> SEQ ID NO 124
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
```

```
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 124

Pro Pro Gly Cys Pro Gly Pro Pro Gly Pro Gly Pro Pro Gly Pro
1               5                   10                  15

Pro Gly Pro Pro Gly
            20

<210> SEQ ID NO 125
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (7)..(7)
<223> OTHER INFORMATION: Chloroproline
```

```
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 125

Pro Pro Gly Pro Cys Gly Pro Pro Gly Pro Pro Gly Pro Pro Gly Pro
1               5                   10                  15

Pro Gly Pro Pro Gly
            20

<210> SEQ ID NO 126
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
```

```
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 126

Pro Pro Gly Pro Pro Gly Cys Pro Gly Pro Pro Gly Pro Pro Gly Pro
1               5                   10                  15

Pro Gly Pro Pro Gly
            20

<210> SEQ ID NO 127
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
```

```
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 127

Pro Pro Gly Pro Pro Gly Pro Cys Gly Pro Pro Gly Pro Pro Gly Pro
1               5                   10                  15

Pro Gly Pro Pro Gly
            20

<210> SEQ ID NO 128
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
```

```
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 128

Pro Pro Gly Pro Pro Gly Pro Pro Gly Cys Pro Gly Pro Pro Gly Pro
1               5                   10                  15

Pro Gly Pro Pro Gly
            20

<210> SEQ ID NO 129
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 129

Pro Pro Gly Pro Pro Gly Pro Pro Gly Pro Cys Gly Pro Pro Gly Pro
```

```
1               5                   10                  15
Pro Gly Pro Pro Gly
        20

<210> SEQ ID NO 130
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 130

Pro Pro Gly Pro Pro Gly Pro Pro Gly Pro Pro Gly Cys Pro Gly Pro
1               5                   10                  15

Pro Gly Pro Pro Gly
        20

<210> SEQ ID NO 131
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 131

Pro Pro Gly Pro Pro Gly Pro Pro Gly Pro Pro Gly Pro Cys Gly Pro
1               5                   10                  15

Pro Gly Pro Pro Gly
            20

<210> SEQ ID NO 132
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
```

```
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 132

Pro Pro Gly Pro Pro Gly Pro Pro Gly Pro Pro Gly Pro Pro Gly Cys
1               5                   10                  15

Pro Gly Pro Pro Gly
            20

<210> SEQ ID NO 133
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
```

```
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 133

Pro Pro Gly Pro Pro Gly Pro Pro Gly Pro Pro Gly Pro Pro Gly Pro
1               5                   10                  15

Cys Gly Pro Pro Gly
            20

<210> SEQ ID NO 134
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
```

<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 134

Pro Pro Gly Pro Pro Gly Pro Pro Gly Pro Pro Gly Pro Pro Gly Pro
1               5                   10                  15

Pro Gly Cys Pro Gly
            20

<210> SEQ ID NO 135
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:

```
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline

<400> SEQUENCE: 135

Pro Pro Gly Pro Pro Gly Pro Pro Gly Pro Pro Gly Pro Pro Gly Pro
1               5                   10                  15

Pro Gly Pro Cys Gly
            20

<210> SEQ ID NO 136
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 137
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 137

Pro Pro Gly Pro Pro Gly Met Pro Gly Pro Pro Gly Pro Pro Gly Pro
1               5                   10                  15
```

```
Pro Gly Pro Pro Gly
        20

<210> SEQ ID NO 138
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 138

Pro Pro Gly Pro Pro Gly Pro Met Gly Pro Pro Gly Pro Pro Gly Pro
1               5                   10                  15

Pro Gly Pro Pro Gly
        20

<210> SEQ ID NO 139
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 139
```

```
Pro Pro Gly Pro Pro Gly Pro Met Gly Pro Pro Gly Pro Pro Gly Pro
1               5                   10                  15

Pro Gly Pro Pro Gly
            20
```

<210> SEQ ID NO 140
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 140

```
Pro Pro Gly Pro Pro Gly Pro Met Gly Pro Pro Gly Pro Pro Gly Pro
1               5                   10                  15

Pro Gly Pro Pro Gly
            20
```

<210> SEQ ID NO 141
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

```
Met Pro Gly Pro Pro Gly Pro Pro Gly Pro Pro Gly Pro Pro Gly Pro
1               5                   10                  15

Pro Gly Pro Pro Gly
            20
```

<210> SEQ ID NO 142
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

```
Pro Met Gly Pro Pro Gly Pro Pro Gly Pro Pro Gly Pro Pro Gly Pro
1               5                   10                  15

Pro Gly Pro Pro Gly
```

20

<210> SEQ ID NO 143
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Pro Pro Gly Met Pro Gly Pro Pro Gly Pro Pro Gly Pro
1               5                   10                  15

Pro Gly Pro Pro Gly
                20

<210> SEQ ID NO 144
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Pro Pro Gly Pro Met Gly Pro Pro Gly Pro Pro Gly Pro Pro Gly Pro
1               5                   10                  15

Pro Gly Pro Pro Gly
                20

<210> SEQ ID NO 145
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Pro Pro Gly Pro Pro Gly Pro Met Gly Pro Pro Gly Pro Pro Gly Pro
1               5                   10                  15

Pro Gly Pro Pro Gly
                20

<210> SEQ ID NO 146
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Pro Pro Gly Pro Pro Gly Pro Pro Gly Met Pro Gly Pro Pro Gly Pro
1               5                   10                  15

Pro Gly Pro Pro Gly
                20

<210> SEQ ID NO 147
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 148
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Pro Pro Gly Pro Pro Gly Pro Pro Gly Pro Pro Gly Met Pro Gly Pro
1               5                   10                  15

Pro Gly Pro Pro Gly
            20

<210> SEQ ID NO 149
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 150
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Pro Pro Gly Pro Pro Gly Pro Pro Gly Pro Pro Gly Pro Pro Gly Met
1               5                   10                  15

Pro Gly Pro Pro Gly
            20

<210> SEQ ID NO 151
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 152
<211> LENGTH: 21

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 153
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 154
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 154

Met Pro Gly Pro Pro Gly Pro Pro Gly Pro Pro Gly Pro Pro Gly Pro
1               5                   10                  15

Pro Gly Pro Pro Gly
            20

<210> SEQ ID NO 155
<211> LENGTH: 21
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 155

Pro Met Gly Pro Pro Gly Pro Pro Gly Pro Pro Gly Pro Pro Gly Pro
1               5                   10                  15

Pro Gly Pro Pro Gly
            20

<210> SEQ ID NO 156
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 156

Pro Pro Gly Met Pro Gly Pro Pro Gly Pro Pro Gly Pro Pro Gly Pro
1               5                   10                  15

Pro Gly Pro Pro Gly
            20
```

```
<210> SEQ ID NO 157
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 157

Pro Pro Gly Pro Met Gly Pro Pro Gly Pro Pro Gly Pro Pro Gly Pro
1               5                   10                  15

Pro Gly Pro Pro Gly
            20

<210> SEQ ID NO 158
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
```

<222> LOCATION: (19)..(19)
<223> OTHER INFORMATION: Hydroxyproline

<400> SEQUENCE: 158

Pro Pro Gly Pro Pro Gly Pro Met Gly Pro Pro Gly Pro Pro Gly Pro
1               5                   10                  15

Pro Gly Pro Pro Gly
            20

<210> SEQ ID NO 159
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 159

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 160
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)

```
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 160

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 161
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 161

Pro Pro Gly Pro Pro Gly Pro Pro Gly Pro Gly Met Pro Gly Pro
1               5                   10                  15

Pro Gly Pro Pro Gly
            20

<210> SEQ ID NO 162
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
```

```
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 162

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 163
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 163

Pro Pro Gly Pro Pro Gly Pro Pro Gly Pro Pro Gly Pro Pro Gly Met
1               5                   10                  15

Pro Gly Pro Pro Gly
            20

<210> SEQ ID NO 164
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
```

```
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 164

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 165
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline

<400> SEQUENCE: 165

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 166
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 166

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 167
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 167

Met Pro Gly Pro Pro Gly Pro Pro Gly Pro Pro Gly Pro Pro Gly Pro
```

```
1               5                   10                  15
Pro Gly Pro Pro Gly
                20
```

<210> SEQ ID NO 168
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 168

```
Pro Met Gly Pro Pro Gly Pro Pro Gly Pro Pro Gly Pro Pro Gly Pro
1               5                   10                  15
Pro Gly Pro Pro Gly
                20
```

<210> SEQ ID NO 169
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:

```
<221> NAME/KEY: MOD_RES
<222> LOCATION: (20)..(20)
<223> OTHER INFORMATION: Hydroxyproline

<400> SEQUENCE: 169

Pro Pro Gly Met Pro Gly Pro Pro Gly Pro Pro Gly Pro Pro Gly Pro
1               5                   10                  15

Pro Gly Pro Pro Gly
            20

<210> SEQ ID NO 170
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 170

Pro Pro Gly Pro Met Gly Pro Pro Gly Pro Pro Gly Pro Pro Gly Pro
1               5                   10                  15

Pro Gly Pro Pro Gly
            20

<210> SEQ ID NO 171
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
```

<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 171

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 172
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 172

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 173
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)

```
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 173

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 174
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 174

Pro Pro Gly Pro Pro Gly Pro Pro Gly Pro Pro Gly Met Pro Gly Pro
1               5                   10                  15

Pro Gly Pro Pro Gly
            20

<210> SEQ ID NO 175
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 175

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 176
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 176

Pro Pro Gly Pro Pro Gly Pro Pro Gly Pro Pro Gly Pro Pro Gly Met
1               5                   10                  15

Pro Gly Pro Pro Gly
            20
```

```
<210> SEQ ID NO 177
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 177

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 178
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 178
```

```
Pro Pro Gly Pro Pro Gly Pro Pro Gly Pro Pro Gly Pro Pro Gly Pro
1               5                   10                  15

Pro Gly Met Pro Gly
            20
```

<210> SEQ ID NO 179
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline

<400> SEQUENCE: 179

```
Pro Pro Gly Pro Pro Gly Pro Pro Gly Pro Pro Gly Pro Pro Gly Pro
1               5                   10                  15

Pro Gly Pro Met Gly
            20
```

<210> SEQ ID NO 180
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

```
<220> FEATURE:
<221> NAME/KEY: MOD_RES
<222> LOCATION: (20)..(20)
<223> OTHER INFORMATION: Fluoroproline

<400> SEQUENCE: 180

Met Pro Gly Pro Pro Gly Pro Pro Gly Pro Pro Gly Pro Pro Gly Pro
1               5                   10                  15

Pro Gly Pro Pro Gly
            20

<210> SEQ ID NO 181
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 181

Pro Met Gly Pro Pro Gly Pro Pro Gly Pro Pro Gly Pro Pro Gly Pro
1               5                   10                  15

Pro Gly Pro Pro Gly
            20

<210> SEQ ID NO 182
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
```

```
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 182

Pro Pro Gly Met Pro Gly Pro Pro Gly Pro Pro Gly Pro Pro Gly Pro
1               5                   10                  15

Pro Gly Pro Pro Gly
            20

<210> SEQ ID NO 183
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 183

Pro Pro Gly Pro Met Gly Pro Pro Gly Pro Pro Gly Pro Pro Gly Pro
1               5                   10                  15

Pro Gly Pro Pro Gly
            20

<210> SEQ ID NO 184
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
```

<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 184

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 185
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 185

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 186
<211> LENGTH: 21
<212> TYPE: PRT
<213> ORGANISM: Artificial Sequence
<220> FEATURE:
<223> OTHER INFORMATION: Description of Artificial Sequence: Synthetic

```
              peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 186

Pro Pro Gly Pro Pro Gly Pro Pro Gly Pro Met Gly Pro Pro Gly
1               5                   10                  15

Pro Gly Pro Pro Gly
            20

<210> SEQ ID NO 187
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 187

Pro Pro Gly Pro Pro Gly Pro Pro Gly Pro Pro Gly Met Pro Gly Pro
1               5                   10                  15

Pro Gly Pro Pro Gly
            20
```

```
<210> SEQ ID NO 188
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 188

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 189
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 189
```

-continued

Pro Pro Gly Pro Pro Gly Pro Pro Gly Pro Pro Gly Pro Pro Gly Met
1               5                   10                  15

Pro Gly Pro Pro Gly
            20

<210> SEQ ID NO 190
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 190

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 191
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)

```
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 191

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 192
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

<400> SEQUENCE: 192

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 193
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
```

```
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 193

Met Pro Gly Pro Pro Gly Pro Pro Gly Pro Pro Gly Pro Pro Gly Pro
1               5                   10                  15

Pro Gly Pro Pro Gly
            20

<210> SEQ ID NO 194
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 194

Pro Met Gly Pro Pro Gly Pro Pro Gly Pro Pro Gly Pro Pro Gly Pro
1               5                   10                  15

Pro Gly Pro Pro Gly
            20

<210> SEQ ID NO 195
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
```

<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 195

Pro Pro Gly Met Pro Gly Pro Pro Gly Pro Pro Gly Pro Pro Gly Pro
1               5                   10                  15

Pro Gly Pro Pro Gly
            20

<210> SEQ ID NO 196
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 196

Pro Pro Gly Pro Met Gly Pro Pro Gly Pro Pro Gly Pro Pro Gly Pro
1               5                   10                  15

Pro Gly Pro Pro Gly
            20

<210> SEQ ID NO 197
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 197

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 198
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 198

Pro Pro Gly Pro Pro Gly Pro Met Gly Pro Pro Gly Pro Pro Gly Pro
1               5                   10                  15

Pro Gly Pro Pro Gly
            20

<210> SEQ ID NO 199
<211> LENGTH: 21

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 199

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 200
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 200

Pro Pro Gly Pro Pro Gly Pro Pro Gly Pro Met Gly Pro Pro Gly Pro
1               5                   10                  15
```

Pro Gly Pro Pro Gly
        20

<210> SEQ ID NO 201
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 201

Pro Pro Gly Pro Pro Gly Pro Pro Gly Pro Pro Gly Met Pro Gly Pro
1               5                   10                  15

Pro Gly Pro Pro Gly
        20

<210> SEQ ID NO 202
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES

```
<222> LOCATION: (20)..(20)
<223> OTHER INFORMATION: Fluoroproline

<400> SEQUENCE: 202

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 203
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 203

Pro Pro Gly Pro Pro Gly Pro Pro Gly Pro Pro Gly Pro Pro Gly Met
1               5                   10                  15

Pro Gly Pro Pro Gly
            20

<210> SEQ ID NO 204
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
```

<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 204

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 205
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 205

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 206
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline

```
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

<400> SEQUENCE: 206

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 207
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
```

```
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 207

Met Pro Gly Pro Pro Gly Pro Pro Gly Pro Pro Gly Pro Pro Gly Pro
1               5                   10                  15

Pro Gly Pro Pro Gly
            20

<210> SEQ ID NO 208
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 208

Pro Met Gly Pro Pro Gly Pro Pro Gly Pro Pro Gly Pro Pro Gly Pro
```

```
1               5                  10                 15
Pro Gly Pro Pro Gly
        20

<210> SEQ ID NO 209
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 209

Pro Pro Gly Met Pro Gly Pro Pro Gly Pro Gly Pro Pro Gly Pro
1               5                  10                 15

Pro Gly Pro Pro Gly
        20

<210> SEQ ID NO 210
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 210

Pro Pro Gly Pro Met Gly Pro Pro Gly Pro Pro Gly Pro Pro Gly Pro
1               5                   10                  15

Pro Gly Pro Pro Gly
            20

<210> SEQ ID NO 211
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
```

```
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 211

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 212
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
```

```
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 212

Pro Pro Gly Pro Pro Gly Pro Met Gly Pro Pro Gly Pro Pro Gly Pro
1               5                   10                  15

Pro Gly Pro Pro Gly
            20

<210> SEQ ID NO 213
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
```

```
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 213

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 214
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
```

<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 214

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 215
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)

<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 215

Pro Pro Gly Pro Pro Gly Pro Pro Gly Pro Pro Gly Met Pro Gly Pro
1               5                   10                  15

Pro Gly Pro Pro Gly
            20

<210> SEQ ID NO 216
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 216

Pro Pro Gly Pro Pro Gly Pro Pro Gly Pro Gly Pro Met Gly Pro
1               5                   10                  15

Pro Gly Pro Pro Gly
        20

<210> SEQ ID NO 217
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 217

Pro Pro Gly Pro Pro Gly Pro Pro Gly Pro Gly Pro Pro Gly Met
1               5                   10                  15

Pro Gly Pro Pro Gly
        20

<210> SEQ ID NO 218
<211> LENGTH: 21
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 218

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 219
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline

```
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 219

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 220
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
```

```
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline

<400> SEQUENCE: 220

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 221
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline
```

<400> SEQUENCE: 221

Met Pro Gly Pro Pro Gly Pro Pro Gly Pro Pro Gly Pro Pro Gly Pro
1               5                   10                  15

Pro Gly Pro Pro Gly
            20

<210> SEQ ID NO 222
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 222

Pro Met Gly Pro Pro Gly Pro Pro Gly Pro Pro Gly Pro Pro Gly Pro
1               5                   10                  15

Pro Gly Pro Pro Gly
            20

<210> SEQ ID NO 223
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:

<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 223

Pro Pro Gly Met Pro Gly Pro Pro Gly Pro Pro Gly Pro Pro Gly Pro
1               5                   10                  15

Pro Gly Pro Pro Gly
            20

<210> SEQ ID NO 224
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 224

Pro Pro Gly Pro Met Gly Pro Pro Gly Pro Pro Gly Pro Pro Gly Pro
1               5                   10                  15

Pro Gly Pro Pro Gly
            20

<210> SEQ ID NO 225
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES

```
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 225

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 226
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 226

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 227
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

-continued

```
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 227

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 228
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 228

Pro Pro Gly Pro Pro Gly Pro Pro Gly Pro Pro Gly Met Pro Gly Pro
1               5                   10                  15

Pro Gly Pro Pro Gly
            20

<210> SEQ ID NO 229
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 229

Pro Pro Gly Pro Pro Gly Pro Pro Gly Pro Pro Gly Pro Met Gly Pro
1               5                   10                  15

Pro Gly Pro Pro Gly
            20

<210> SEQ ID NO 230
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 230

Pro Pro Gly Pro Pro Gly Pro Pro Gly Pro Pro Gly Pro Pro Gly Met
1               5                   10                  15
```

Pro Gly Pro Pro Gly
        20

<210> SEQ ID NO 231
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 231

Pro Pro Gly Pro Pro Gly Pro Pro Gly Pro Pro Gly Pro Pro Gly Pro
1               5                   10                  15

Met Gly Pro Pro Gly
        20

<210> SEQ ID NO 232
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)

<223> OTHER INFORMATION: Chloroproline

<400> SEQUENCE: 232

Pro Pro Gly Pro Pro Gly Pro Pro Gly Pro Pro Gly Pro Pro Gly Pro
1               5                   10                  15
Pro Gly Met Pro Gly
            20

<210> SEQ ID NO 233
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline

<400> SEQUENCE: 233

Pro Pro Gly Pro Pro Gly Pro Pro Gly Pro Pro Gly Pro Pro Gly Pro
1               5                   10                  15
Pro Gly Pro Met Gly
            20

<210> SEQ ID NO 234
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline

```
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 234

Met Pro Gly Pro Pro Gly Pro Pro Gly Pro Pro Gly Pro Pro Gly Pro
1               5                   10                  15

Pro Gly Pro Pro Gly
            20

<210> SEQ ID NO 235
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 235

Pro Met Gly Pro Pro Gly Pro Pro Gly Pro Pro Gly Pro Pro Gly Pro
1               5                   10                  15

Pro Gly Pro Pro Gly
            20

<210> SEQ ID NO 236
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
```

```
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 236

Pro Pro Gly Met Pro Gly Pro Pro Gly Pro Pro Gly Pro Pro Gly Pro
1               5                   10                  15

Pro Gly Pro Pro Gly
            20

<210> SEQ ID NO 237
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 237

Pro Pro Gly Pro Met Gly Pro Pro Gly Pro Pro Gly Pro Pro Gly Pro
1               5                   10                  15

Pro Gly Pro Pro Gly
            20

<210> SEQ ID NO 238
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
```

```
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 238

Pro Pro Gly Pro Pro Gly Met Pro Gly Pro Pro Gly Pro Pro Gly Pro
1               5                   10                  15
Pro Gly Pro Pro Gly
            20

<210> SEQ ID NO 239
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 239

Pro Pro Gly Pro Pro Gly Pro Met Gly Pro Pro Gly Pro Pro Gly Pro
1               5                   10                  15
Pro Gly Pro Pro Gly
            20

<210> SEQ ID NO 240
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 240

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 241
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 241

Pro Pro Gly Pro Pro Gly Pro Pro Gly Pro Met Gly Pro Pro Gly Pro
1               5                   10                  15

Pro Gly Pro Pro Gly
            20
```

```
<210> SEQ ID NO 242
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 242

Pro Pro Gly Pro Pro Gly Pro Pro Gly Pro Pro Gly Met Pro Gly Pro
1               5                   10                  15

Pro Gly Pro Pro Gly
            20

<210> SEQ ID NO 243
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 243
```

```
Pro Pro Gly Pro Pro Gly Pro Pro Gly Pro Pro Gly Pro Met Gly Pro
1               5                   10                  15

Pro Gly Pro Pro Gly
            20

<210> SEQ ID NO 244
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 244

Pro Pro Gly Pro Pro Gly Pro Pro Gly Pro Pro Gly Pro Pro Gly Met
1               5                   10                  15

Pro Gly Pro Pro Gly
            20

<210> SEQ ID NO 245
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
```

```
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 245

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 246
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 246

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 247
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
```

```
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline

<400> SEQUENCE: 247

Pro Pro Gly Pro Pro Gly Pro Pro Gly Pro Pro Gly Pro Pro Gly Pro
1               5                   10                  15

Pro Gly Pro Met Gly
            20

<210> SEQ ID NO 248
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
```

<222> LOCATION: (20)..(20)
<223> OTHER INFORMATION: Hydroxyproline

<400> SEQUENCE: 248

Met Pro Gly Pro Pro Gly Pro Pro Gly Pro Pro Gly Pro Pro Gly Pro
1               5                   10                  15

Pro Gly Pro Pro Gly
            20

<210> SEQ ID NO 249
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 249

Pro Met Gly Pro Pro Gly Pro Pro Gly Pro Pro Gly Pro Pro Gly Pro
1               5                   10                  15

Pro Gly Pro Pro Gly
            20

```
<210> SEQ ID NO 250
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 250

Pro Pro Gly Met Pro Gly Pro Pro Gly Pro Pro Gly Pro Pro Gly Pro
1               5                   10                  15

Pro Gly Pro Pro Gly
            20

<210> SEQ ID NO 251
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 251

Pro Pro Gly Pro Met Gly Pro Pro Gly Pro Pro Gly Pro Pro Gly Pro
1               5                   10                  15

Pro Gly Pro Pro Gly
            20

<210> SEQ ID NO 252
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
```

-continued

```
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 252

Pro Pro Gly Pro Pro Gly Met Pro Gly Pro Pro Gly Pro Pro Gly Pro
1               5                   10                  15

Pro Gly Pro Pro Gly
            20

<210> SEQ ID NO 253
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
```

<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 253

Pro Pro Gly Pro Pro Gly Pro Met Gly Pro Pro Gly Pro Pro Gly Pro
1               5                   10                  15

Pro Gly Pro Pro Gly
            20

<210> SEQ ID NO 254
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)

```
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 254

Pro Pro Gly Pro Pro Gly Pro Pro Gly Met Pro Gly Pro Pro Gly Pro
1               5                   10                  15

Pro Gly Pro Pro Gly
            20

<210> SEQ ID NO 255
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
```

```
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 255

Pro Pro Gly Pro Pro Gly Pro Pro Gly Pro Met Gly Pro Pro Gly Pro
1               5                   10                  15

Pro Gly Pro Pro Gly
            20

<210> SEQ ID NO 256
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
```

<223> OTHER INFORMATION: Hydroxyproline

<400> SEQUENCE: 256

Pro Pro Gly Pro Pro Gly Pro Pro Gly Pro Gly Met Pro Gly Pro
1               5                   10                  15

Pro Gly Pro Pro Gly
            20

<210> SEQ ID NO 257
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 257

Pro Pro Gly Pro Pro Gly Pro Pro Gly Pro Pro Gly Pro Met Gly Pro
1               5                   10                  15

Pro Gly Pro Pro Gly
            20

```
<210> SEQ ID NO 258
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 258

Pro Pro Gly Pro Pro Gly Pro Pro Gly Pro Pro Gly Pro Pro Gly Met
1               5                   10                  15

Pro Gly Pro Pro Gly
            20

<210> SEQ ID NO 259
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 259

Pro Pro Gly Pro Pro Gly Pro Pro Gly Pro Pro Gly Pro Pro Gly Pro
1               5                   10                  15

Met Gly Pro Pro Gly
            20

<210> SEQ ID NO 260
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline

```
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 260

Pro Pro Gly Pro Pro Gly Pro Pro Gly Pro Pro Gly Pro Pro Gly Pro
1               5                   10                  15

Pro Gly Met Pro Gly
            20

<210> SEQ ID NO 261
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
```

<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline

<400> SEQUENCE: 261

Pro Pro Gly Pro Pro Gly Pro Pro Gly Pro Pro Gly Pro Pro Gly Pro
1               5                   10                  15
Pro Gly Pro Met Gly
            20

<210> SEQ ID NO 262
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Pro Pro Gly Pro Pro Gly Lys Pro Gly Pro Pro Gly Pro Pro Gly Pro
1               5                   10                  15
Pro Gly Pro Pro Gly
            20

<210> SEQ ID NO 263
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)

```
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 263

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 264
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 264

Pro Pro Gly Pro Pro Gly Pro Lys Gly Pro Pro Gly Pro Pro Gly Pro
1               5                   10                  15

Pro Gly Pro Pro Gly
            20

<210> SEQ ID NO 265
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
```

```
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 265

Pro Pro Gly Pro Pro Gly Pro Lys Gly Pro Pro Gly Pro Pro Gly Pro
1               5                   10                  15

Pro Gly Pro Pro Gly
            20

<210> SEQ ID NO 266
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 266

Pro Pro Gly Pro Pro Gly Pro Lys Gly Pro Pro Gly Pro Pro Gly Pro
1               5                   10                  15

Pro Gly Pro Pro Gly
            20

<210> SEQ ID NO 267
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Lys Pro Gly Pro Pro Gly Pro Pro Gly Pro Pro Gly Pro Pro Gly Pro
1               5                   10                  15

Pro Gly Pro Pro Gly
            20
```

<210> SEQ ID NO 268
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 268

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 269
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 269

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 270
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 270

Pro Pro Gly Pro Lys Gly Pro Pro Gly Pro Pro Gly Pro Pro Gly Pro
1               5                   10                  15

Pro Gly Pro Pro Gly
            20

<210> SEQ ID NO 271
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 271

Pro Pro Gly Pro Pro Gly Pro Lys Gly Pro Pro Gly Pro Pro Gly Pro
1               5                   10                  15

Pro Gly Pro Pro Gly
            20

<210> SEQ ID NO 272
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 272

-continued

Pro Pro Gly Pro Pro Gly Pro Pro Gly Lys Pro Gly Pro Pro Gly Pro
1               5                   10                  15

Pro Gly Pro Pro Gly
        20

<210> SEQ ID NO 273
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Pro Pro Gly Pro Pro Gly Pro Pro Gly Pro Lys Gly Pro Pro Gly Pro
1               5                   10                  15

Pro Gly Pro Pro Gly
        20

<210> SEQ ID NO 274
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Pro Pro Gly Pro Pro Gly Pro Pro Gly Pro Pro Gly Lys Pro Gly Pro
1               5                   10                  15

Pro Gly Pro Pro Gly
        20

<210> SEQ ID NO 275
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Pro Pro Gly Pro Pro Gly Pro Pro Gly Pro Pro Gly Pro Lys Gly Pro
1               5                   10                  15

Pro Gly Pro Pro Gly
        20

<210> SEQ ID NO 276
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Pro Pro Gly Pro Pro Gly Pro Pro Gly Pro Pro Gly Pro Pro Gly Lys
1               5                   10                  15

Pro Gly Pro Pro Gly
        20

<210> SEQ ID NO 277
<211> LENGTH: 21
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 277

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 278
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 279
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 280
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline
```

```
<400> SEQUENCE: 280

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 281
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 281

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 282
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
```

```
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 282

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 283
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 283

Pro Pro Gly Pro Lys Gly Pro Pro Gly Pro Pro Gly Pro Pro Gly Pro
1               5                   10                  15

Pro Gly Pro Pro Gly
            20

<210> SEQ ID NO 284
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
```

<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 284

Pro Pro Gly Pro Pro Gly Pro Lys Gly Pro Pro Gly Pro Pro Gly Pro
1               5                   10                  15

Pro Gly Pro Pro Gly
            20

<210> SEQ ID NO 285
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 285

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 286
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline

```
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 286

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 287
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 287

Pro Pro Gly Pro Pro Gly Pro Pro Gly Pro Gly Lys Pro Gly Pro
1               5                   10                  15

Pro Gly Pro Pro Gly
            20

<210> SEQ ID NO 288
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 288

Pro Pro Gly Pro Pro Gly Pro Pro Gly Pro Pro Gly Pro Lys Gly Pro
1               5                   10                  15

Pro Gly Pro Pro Gly
            20

<210> SEQ ID NO 289
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 289

Pro Pro Gly Pro Pro Gly Pro Pro Gly Pro Pro Gly Pro Pro Gly Lys
1               5                   10                  15

Pro Gly Pro Pro Gly
```

<210> SEQ ID NO 290
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 290

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 291
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline

```
<400> SEQUENCE: 291

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 292
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline
<220> FEATURE:
<221> NAME/KEY: MOD_RES
<222> LOCATION: (10)..(10)
<223> OTHER INFORMATION: Hydroxyproline
<220> FEATURE:
<221> NAME/KEY: MOD_RES
<222> LOCATION: (13)..(13)
<223> OTHER INFORMATION: Hydroxyproline
<220> FEATURE:
<221> NAME/KEY: MOD_RES
<222> LOCATION: (16)..(16)
<223> OTHER INFORMATION: Hydroxyproline
<220> FEATURE:
<221> NAME/KEY: MOD_RES
<222> LOCATION: (19)..(19)
<223> OTHER INFORMATION: Hydroxyproline

<400> SEQUENCE: 292

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 293
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
```

```
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 293

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 294
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 294

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 295
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
```

```
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 295

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 296
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 296

Pro Pro Gly Pro Lys Gly Pro Pro Gly Pro Pro Gly Pro Pro Gly Pro
1               5                   10                  15

Pro Gly Pro Pro Gly
            20

<210> SEQ ID NO 297
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 297

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 298
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 298

Pro Pro Gly Pro Pro Gly Pro Pro Gly Lys Pro Gly Pro Pro Gly Pro
1               5                   10                  15

Pro Gly Pro Pro Gly
            20

```
<210> SEQ ID NO 299
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 299

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 300
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 300
```

Pro Pro Gly Pro Pro Gly Pro Pro Gly Pro Pro Gly Lys Pro Gly Pro
1               5               10              15

Pro Gly Pro Pro Gly
            20

<210> SEQ ID NO 301
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 301

Pro Pro Gly Pro Pro Gly Pro Pro Gly Pro Pro Gly Pro Lys Gly Pro
1               5               10              15

Pro Gly Pro Pro Gly
            20

<210> SEQ ID NO 302
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)

```
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 302

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 303
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 303

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 304
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
```

<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 304

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 305
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline

<400> SEQUENCE: 305

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 306
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:

```
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 306

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 307
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 307

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 308
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 308

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 309
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 309

Pro Pro Gly Pro Lys Gly Pro Pro Gly Pro Pro Gly Pro Pro Gly Pro
1               5                   10                  15

Pro Gly Pro Pro Gly
            20

<210> SEQ ID NO 310
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 310

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 311
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline
```

-continued

```
<400> SEQUENCE: 311

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 312
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 312

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 313
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
```

```
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 313

Pro Pro Gly Pro Pro Gly Pro Pro Gly Pro Pro Gly Lys Pro Gly Pro
1               5                   10                  15

Pro Gly Pro Pro Gly
            20

<210> SEQ ID NO 314
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 314

Pro Pro Gly Pro Pro Gly Pro Pro Gly Pro Pro Gly Pro Lys Gly Pro
1               5                   10                  15

Pro Gly Pro Pro Gly
            20

<210> SEQ ID NO 315
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
```

```
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 315

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 316
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 316

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 317
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
```

```
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 317

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 318
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

<400> SEQUENCE: 318

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 319
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 319

Lys Pro Gly Pro Pro Gly Pro Pro Gly Pro Pro Gly Pro Pro Gly Pro
1               5                   10                  15
Pro Gly Pro Pro Gly
            20

<210> SEQ ID NO 320
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 320

Pro Lys Gly Pro Pro Gly Pro Pro Gly Pro Pro Gly Pro Pro Gly Pro
1               5                   10                  15
Pro Gly Pro Pro Gly
            20

<210> SEQ ID NO 321
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 321

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 322
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 322

Pro Pro Gly Pro Lys Gly Pro Pro Gly Pro Pro Gly Pro Pro Gly Pro
```

```
1               5                   10                  15
Pro Gly Pro Pro Gly
            20

<210> SEQ ID NO 323
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 323

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 324
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
```

```
<221> NAME/KEY: MOD_RES
<222> LOCATION: (20)..(20)
<223> OTHER INFORMATION: Fluoroproline

<400> SEQUENCE: 324

Pro Pro Gly Pro Pro Gly Pro Lys Gly Pro Pro Gly Pro Pro Gly Pro
1               5                   10                  15

Pro Gly Pro Pro Gly
            20

<210> SEQ ID NO 325
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 325

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 326
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
```

```
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 326

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 327
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 327

Pro Pro Gly Pro Pro Gly Pro Pro Gly Pro Pro Gly Lys Pro Gly Pro
1               5                   10                  15

Pro Gly Pro Pro Gly
            20

<210> SEQ ID NO 328
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
```

<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 328

Pro Pro Gly Pro Pro Gly Pro Pro Gly Pro Gly Pro Lys Gly Pro
1               5                   10                  15

Pro Gly Pro Pro Gly
            20

<210> SEQ ID NO 329
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 329

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 330
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 330

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 331
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 331

Pro Pro Gly Pro Pro Gly Pro Pro Gly Pro Pro Gly Pro Pro Gly Pro
1               5                   10                  15

Pro Gly Lys Pro Gly
            20
```

```
<210> SEQ ID NO 332
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

<400> SEQUENCE: 332

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 333
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
```

```
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 333

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 334
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
```

```
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 334

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 335
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
```

<223> OTHER INFORMATION: Hydroxyproline

<400> SEQUENCE: 335

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 336
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 336

Pro Pro Gly Pro Lys Gly Pro Pro Gly Pro Pro Gly Pro Pro Gly Pro
1               5                   10                  15

Pro Gly Pro Pro Gly
            20

```
<210> SEQ ID NO 337
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 337

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 338
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 338

Pro Pro Gly Pro Pro Gly Pro Lys Gly Pro Pro Gly Pro Pro Gly Pro
1               5                   10                  15

Pro Gly Pro Pro Gly
            20

<210> SEQ ID NO 339
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline

```
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 339

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 340
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
```

```
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 340

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 341
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
```

```
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 341

Pro Pro Gly Pro Pro Gly Pro Pro Gly Pro Pro Gly Lys Pro Gly Pro
1               5                   10                  15

Pro Gly Pro Pro Gly
            20

<210> SEQ ID NO 342
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
```

```
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 342

Pro Pro Gly Pro Pro Gly Pro Pro Gly Pro Pro Gly Pro Lys Gly Pro
1               5                   10                  15

Pro Gly Pro Pro Gly
            20

<210> SEQ ID NO 343
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline
```

<400> SEQUENCE: 343

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 344
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: Hydroxyproline

<400> SEQUENCE: 344

Pro Pro Gly Pro Pro Gly Pro Pro Gly Pro Pro Gly Pro Pro Gly Pro
1               5                   10                  15

Lys Gly Pro Pro Gly
            20

```
<210> SEQ ID NO 345
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 345

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 346
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Fluoroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Fluoroproline

<400> SEQUENCE: 346

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 347
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
```

<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 347

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 348
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 348

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 349
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES

```
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 349

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 350
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 350

Pro Pro Gly Pro Lys Gly Pro Pro Gly Pro Pro Gly Pro Pro Gly Pro
1               5                   10                  15

Pro Gly Pro Pro Gly
            20

<210> SEQ ID NO 351
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 351

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 352
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 352

Pro Pro Gly Pro Pro Gly Pro Pro Gly Lys Pro Gly Pro Pro Gly Pro
1               5                   10                  15
```

Pro Gly Pro Pro Gly
            20

<210> SEQ ID NO 353
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 353

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 354
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 354

Pro Pro Gly Pro Pro Gly Pro Pro Gly Pro Pro Gly Lys Pro Gly Pro
1               5                   10                  15

Pro Gly Pro Pro Gly
            20

<210> SEQ ID NO 355
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 355

Pro Pro Gly Pro Pro Gly Pro Pro Gly Pro Pro Gly Pro Lys Gly Pro
1               5                   10                  15

Pro Gly Pro Pro Gly
            20

<210> SEQ ID NO 356
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)

```
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 356

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 357
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 357

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 358
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
```

```
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 358

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 359
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline

<400> SEQUENCE: 359

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 360
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
```

```
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 360

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 361
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 361

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 362
<211> LENGTH: 21
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 362

Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 363
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 363

Pro Pro Gly Pro Lys Gly Pro Pro Gly Pro Pro Gly Pro Pro Gly Pro
1               5                   10                  15

Pro Gly Pro Pro Gly
            20

```
<210> SEQ ID NO 364
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 364

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 365
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline
```

-continued

```
<400> SEQUENCE: 365

Pro Pro Gly Pro Pro Gly Pro Lys Gly Pro Pro Gly Pro Pro Gly Pro
1               5                   10                  15

Pro Gly Pro Pro Gly
            20

<210> SEQ ID NO 366
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 366

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 367
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
```

```
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 367

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 368
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 368

Pro Pro Gly Pro Pro Gly Pro Pro Gly Pro Gly Lys Pro Pro Gly Pro
1               5                   10                  15

Pro Gly Pro Pro Gly
            20

<210> SEQ ID NO 369
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
```

<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 369

Pro Pro Gly Pro Pro Gly Pro Pro Gly Pro Gly Pro Lys Gly Pro
1               5                   10                  15

Pro Gly Pro Pro Gly
            20

<210> SEQ ID NO 370
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 370

Pro Pro Gly Pro Pro Gly Pro Pro Gly Pro Pro Gly Pro Pro Gly Lys
1               5                   10                  15

Pro Gly Pro Pro Gly
            20

<210> SEQ ID NO 371
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline

```
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 371

Pro Pro Gly Pro Pro Gly Pro Pro Gly Pro Pro Gly Pro Pro Gly Pro
1               5                   10                  15

Lys Gly Pro Pro Gly
            20

<210> SEQ ID NO 372
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 372

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 373
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline

<400> SEQUENCE: 373

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 374
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
```

```
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 374

Lys Pro Gly Pro Pro Gly Pro Pro Gly Pro Pro Gly Pro Pro Gly Pro
1               5                   10                  15

Pro Gly Pro Pro Gly
            20

<210> SEQ ID NO 375
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
```

```
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 375

Pro Lys Gly Pro Pro Gly Pro Pro Gly Pro Pro Gly Pro Pro Gly Pro
1               5                   10                  15

Pro Gly Pro Pro Gly
            20

<210> SEQ ID NO 376
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 376
```

```
Pro Pro Gly Lys Pro Gly Pro Pro Gly Pro Pro Gly Pro Pro Gly Pro
1               5                   10                  15

Pro Gly Pro Pro Gly
            20

<210> SEQ ID NO 377
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 377

Pro Pro Gly Pro Lys Gly Pro Pro Gly Pro Pro Gly Pro Pro Gly Pro
1               5                   10                  15

Pro Gly Pro Pro Gly
            20

<210> SEQ ID NO 378
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 378

Pro Pro Gly Pro Pro Gly Lys Pro Gly Pro Pro Gly Pro Pro Gly Pro
1               5                   10                  15

Pro Gly Pro Pro Gly
            20

<210> SEQ ID NO 379
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
```

```
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 379

Pro Pro Gly Pro Pro Gly Pro Lys Gly Pro Pro Gly Pro Pro Gly Pro
1               5                   10                  15

Pro Gly Pro Pro Gly
            20

<210> SEQ ID NO 380
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
```

-continued

```
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 380

Pro Pro Gly Pro Pro Gly Pro Pro Gly Lys Pro Gly Pro Pro Gly Pro
1               5                   10                  15

Pro Gly Pro Pro Gly
            20

<210> SEQ ID NO 381
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
```

<222> LOCATION: (10)..(10)
<223> OTHER INFORMATION: Chloroproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 381

Pro Pro Gly Pro Pro Gly Pro Pro Gly Pro Lys Gly Pro Pro Gly Pro
1               5                   10                  15

Pro Gly Pro Pro Gly
            20

<210> SEQ ID NO 382
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (14)..(14)
<223> OTHER INFORMATION: Hydroxyproline

```
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 382

Pro Pro Gly Pro Pro Gly Pro Pro Gly Pro Pro Gly Lys Pro Gly Pro
1               5                   10                  15

Pro Gly Pro Pro Gly
            20

<210> SEQ ID NO 383
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
```

```
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 383

Pro Pro Gly Pro Pro Gly Pro Pro Gly Pro Pro Gly Pro Lys Gly Pro
1               5                   10                  15

Pro Gly Pro Pro Gly
            20

<210> SEQ ID NO 384
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 384

Pro Pro Gly Pro Pro Gly Pro Pro Gly Pro Pro Gly Pro Pro Gly Lys
```

```
1               5                   10                  15
Pro Gly Pro Pro Gly
        20

<210> SEQ ID NO 385
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: Hydroxyproline

<400> SEQUENCE: 385

Pro Pro Gly Pro Pro Gly Pro Pro Gly Pro Pro Gly Pro Pro Gly Pro
1               5                   10                  15

Lys Gly Pro Pro Gly
        20

<210> SEQ ID NO 386
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (20)..(20)
<223> OTHER INFORMATION: Hydroxyproline

<400> SEQUENCE: 386

Pro Pro Gly Pro Pro Gly Pro Pro Gly Pro Pro Gly Pro Pro Gly Pro
1               5                   10                  15

Pro Gly Lys Pro Gly
            20

<210> SEQ ID NO 387
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
```

```
<223> OTHER INFORMATION: Hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: Hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: Hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: Hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: Hydroxyproline
<220> FEATURE:
<221> NAME/KEY: MOD_RES
<222> LOCATION: (19)..(19)
<223> OTHER INFORMATION: Chloroproline

<400> SEQUENCE: 387

Pro Pro Gly Pro Pro Gly Pro Pro Gly Pro Pro Gly Pro Pro Gly Pro
1               5                   10                  15

Pro Gly Pro Lys Gly
            20

<210> SEQ ID NO 388
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4S-hydroxyproline
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (4)..(4)
<223> OTHER INFORMATION: 4S-hydroxyproline
<220> FEATURE:
<221> NAME/KEY: MOD_RES
<222> LOCATION: (5)..(5)
<223> OTHER INFORMATION: Fluoroproline
<220> FEATURE:
```

```
<221> NAME/KEY: MOD_RES
<222> LOCATION: (7)..(7)
<223> OTHER INFORMATION: 4S-hydroxyproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (10)..(10)
<223> OTHER INFORMATION: 4S-hydroxyproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (13)..(13)
<223> OTHER INFORMATION: 4S-hydroxyproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (16)..(16)
<223> OTHER INFORMATION: 4S-hydroxyproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (19)..(19)
<223> OTHER INFORMATION: 4S-hydroxyproline
<220> FEATURE:
<221> NAME/KEY: MOD_RES
<222> LOCATION: (20)..(20)
<223> OTHER INFORMATION: Fluoroproline

<400> SEQUENCE: 388

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 389
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Arg Pro Lys Pro Gln Gln Phe Phe Gly Leu Met
1               5                   10

<210> SEQ ID NO 390
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 390

Pro Pro Gly Pro Pro Gly Pro Pro Gly Pro Pro Gly Pro Pro Gly Pro
1               5                   10                  15

Pro Gly Pro Pro Gly Arg Pro Lys Pro Gln Gln Phe Phe Gly Leu Met
            20                  25                  30
```

```
<210> SEQ ID NO 391
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4S-hydroxyproline
<220> FEATURE:
<221> NAME/KEY: MOD_RES
<222> LOCATION: (4)..(4)
<223> OTHER INFORMATION: 4S-hydroxyproline
<220> FEATURE:
<221> NAME/KEY: MOD_RES
<222> LOCATION: (7)..(7)
<223> OTHER INFORMATION: 4S-hydroxyproline
<220> FEATURE:
<221> NAME/KEY: MOD_RES
<222> LOCATION: (10)..(10)
<223> OTHER INFORMATION: 4S-hydroxyproline
<220> FEATURE:
<221> NAME/KEY: MOD_RES
<222> LOCATION: (13)..(13)
<223> OTHER INFORMATION: 4S-hydroxyproline
<220> FEATURE:
<221> NAME/KEY: MOD_RES
<222> LOCATION: (16)..(16)
<223> OTHER INFORMATION: 4S-hydroxyproline
<220> FEATURE:
<221> NAME/KEY: MOD_RES
<222> LOCATION: (19)..(19)
<223> OTHER INFORMATION: 4S-hydroxyproline

<400> SEQUENCE: 391

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 392
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: 4S-hydroxyproline
<220> FEATURE:
<221> NAME/KEY: MOD_RES
<222> LOCATION: (5)..(5)
<223> OTHER INFORMATION: 4S-hydroxyproline
<220> FEATURE:
<221> NAME/KEY: MOD_RES
<222> LOCATION: (8)..(8)
<223> OTHER INFORMATION: 4S-hydroxyproline
<220> FEATURE:
<221> NAME/KEY: MOD_RES
<222> LOCATION: (11)..(11)
<223> OTHER INFORMATION: 4S-hydroxyproline
<220> FEATURE:
<221> NAME/KEY: MOD_RES
<222> LOCATION: (14)..(14)
<223> OTHER INFORMATION: 4S-hydroxyproline
<220> FEATURE:
<221> NAME/KEY: MOD_RES
<222> LOCATION: (17)..(17)
<223> OTHER INFORMATION: 4S-hydroxyproline
<220> FEATURE:
<221> NAME/KEY: MOD_RES
```

-continued

```
<222> LOCATION: (20)..(20)
<223> OTHER INFORMATION: 4S-hydroxyproline

<400> SEQUENCE: 392

Pro Pro Gly Pro Pro Gly Pro Pro Gly Pro Pro Gly Pro Pro Gly Pro
1               5                   10                  15

Pro Gly Pro Pro Gly Arg Pro Lys Pro Gln Gln Phe Phe Gly Leu Met
            20                  25                  30

<210> SEQ ID NO 393
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Fluoroproline
<220> FEATURE:
<221> NAME/KEY: MOD_RES
<222> LOCATION: (2)..(2)
<223> OTHER INFORMATION: 4S-hydroxyproline
<220> FEATURE:
<221> NAME/KEY: MOD_RES
<222> LOCATION: (4)..(4)
<223> OTHER INFORMATION: Fluoroproline
<220> FEATURE:
<221> NAME/KEY: MOD_RES
<222> LOCATION: (5)..(5)
<223> OTHER INFORMATION: 4S-hydroxyproline
<220> FEATURE:
<221> NAME/KEY: MOD_RES
<222> LOCATION: (7)..(7)
<223> OTHER INFORMATION: Fluoroproline
<220> FEATURE:
<221> NAME/KEY: MOD_RES
<222> LOCATION: (8)..(8)
<223> OTHER INFORMATION: 4S-hydroxyproline
<220> FEATURE:
<221> NAME/KEY: MOD_RES
<222> LOCATION: (10)..(10)
<223> OTHER INFORMATION: Fluoroproline
<220> FEATURE:
<221> NAME/KEY: MOD_RES
<222> LOCATION: (11)..(11)
<223> OTHER INFORMATION: 4S-hydroxyproline
<220> FEATURE:
<221> NAME/KEY: MOD_RES
<222> LOCATION: (13)..(13)
<223> OTHER INFORMATION: Fluoroproline
<220> FEATURE:
<221> NAME/KEY: MOD_RES
<222> LOCATION: (14)..(14)
<223> OTHER INFORMATION: 4S-hydroxyproline
<220> FEATURE:
<221> NAME/KEY: MOD_RES
<222> LOCATION: (16)..(16)
<223> OTHER INFORMATION: Fluoroproline
<220> FEATURE:
<221> NAME/KEY: MOD_RES
<222> LOCATION: (17)..(17)
<223> OTHER INFORMATION: 4S-hydroxyproline
<220> FEATURE:
<221> NAME/KEY: MOD_RES
<222> LOCATION: (19)..(19)
<223> OTHER INFORMATION: Fluoroproline
<220> FEATURE:
<221> NAME/KEY: MOD_RES
<222> LOCATION: (20)..(20)
<223> OTHER INFORMATION: 4S-hydroxyproline

<400> SEQUENCE: 393

Pro Pro Gly Pro Pro Gly Pro Pro Gly Pro Pro Gly Pro Pro Gly Pro
```

```
1               5                   10                  15
Pro Gly Pro Pro Gly Arg Pro Lys Pro Gln Gln Phe Phe Gly Leu Met
        20                  25                  30
```

<210> SEQ ID NO 394
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Chloroproline
<220> FEATURE:
<221> NAME/KEY: MOD_RES
<222> LOCATION: (2)..(2)
<223> OTHER INFORMATION: 4S-hydroxyproline
<220> FEATURE:
<221> NAME/KEY: MOD_RES
<222> LOCATION: (4)..(4)
<223> OTHER INFORMATION: Chloroproline
<220> FEATURE:
<221> NAME/KEY: MOD_RES
<222> LOCATION: (5)..(5)
<223> OTHER INFORMATION: 4S-hydroxyproline
<220> FEATURE:
<221> NAME/KEY: MOD_RES
<222> LOCATION: (7)..(7)
<223> OTHER INFORMATION: Chloroproline
<220> FEATURE:
<221> NAME/KEY: MOD_RES
<222> LOCATION: (8)..(8)
<223> OTHER INFORMATION: 4S-hydroxyproline
<220> FEATURE:
<221> NAME/KEY: MOD_RES
<222> LOCATION: (10)..(10)
<223> OTHER INFORMATION: Chloroproline
<220> FEATURE:
<221> NAME/KEY: MOD_RES
<222> LOCATION: (11)..(11)
<223> OTHER INFORMATION: 4S-hydroxyproline
<220> FEATURE:
<221> NAME/KEY: MOD_RES
<222> LOCATION: (13)..(13)
<223> OTHER INFORMATION: Chloroproline
<220> FEATURE:
<221> NAME/KEY: MOD_RES
<222> LOCATION: (14)..(14)
<223> OTHER INFORMATION: 4S-hydroxyproline
<220> FEATURE:
<221> NAME/KEY: MOD_RES
<222> LOCATION: (16)..(16)
<223> OTHER INFORMATION: Chloroproline
<220> FEATURE:
<221> NAME/KEY: MOD_RES
<222> LOCATION: (17)..(17)
<223> OTHER INFORMATION: 4S-hydroxyproline
<220> FEATURE:
<221> NAME/KEY: MOD_RES
<222> LOCATION: (19)..(19)
<223> OTHER INFORMATION: Chloroproline
<220> FEATURE:
<221> NAME/KEY: MOD_RES
<222> LOCATION: (20)..(20)
<223> OTHER INFORMATION: 4S-hydroxyproline

<400> SEQUENCE: 394

```
Pro Pro Gly Pro Pro Gly Pro Pro Gly Pro Pro Gly Pro Pro Gly Pro
1               5                   10                  15

Pro Gly Pro Pro Gly Arg Pro Lys Pro Gln Gln Phe Phe Gly Leu Met
        20                  25                  30
```

```
<210> SEQ ID NO 395
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 395

Pro Pro Gly Pro Pro Gly Pro Pro Gly Pro Pro Gly Pro Pro Gly Pro
1               5                   10                  15

Pro Gly Pro Pro Gly Arg Pro Lys Pro Gln Gln Phe Phe Gly Leu Met
            20                  25                  30

<210> SEQ ID NO 396
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: 4S-hydroxyproline
<220> FEATURE:
<221> NAME/KEY: MOD_RES
<222> LOCATION: (5)..(5)
<223> OTHER INFORMATION: 4S-hydroxyproline
<220> FEATURE:
<221> NAME/KEY: MOD_RES
<222> LOCATION: (8)..(8)
<223> OTHER INFORMATION: 4S-hydroxyproline
<220> FEATURE:
<221> NAME/KEY: MOD_RES
<222> LOCATION: (11)..(11)
<223> OTHER INFORMATION: 4S-hydroxyproline
<220> FEATURE:
<221> NAME/KEY: MOD_RES
<222> LOCATION: (14)..(14)
<223> OTHER INFORMATION: 4S-hydroxyproline
<220> FEATURE:
<221> NAME/KEY: MOD_RES
<222> LOCATION: (17)..(17)
<223> OTHER INFORMATION: 4S-hydroxyproline
<220> FEATURE:
<221> NAME/KEY: MOD_RES
<222> LOCATION: (20)..(20)
```

```
<223> OTHER INFORMATION: 4S-hydroxyproline
<220> FEATURE:
<221> NAME/KEY: MOD_RES
<222> LOCATION: (23)..(23)
<223> OTHER INFORMATION: 4S-hydroxyproline
<220> FEATURE:
<221> NAME/KEY: MOD_RES
<222> LOCATION: (26)..(26)
<223> OTHER INFORMATION: 4S-hydroxyproline
<220> FEATURE:
<221> NAME/KEY: MOD_RES
<222> LOCATION: (29)..(29)
<223> OTHER INFORMATION: 4S-hydroxyproline

<400> SEQUENCE: 396

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly
            20                  25                  30

<210> SEQ ID NO 397
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

Pro Pro Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly
            20                  25                  30

<210> SEQ ID NO 398
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (2)..(2)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (4)..(4)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (5)..(5)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (7)..(7)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (8)..(8)
<223> OTHER INFORMATION: Pro, 4R-hydroxyproline, fluoroproline,
      chloroproline, Lys, Cys or Met
<220> FEATURE:
<221> NAME/KEY: MOD_RES
```

```
<222> LOCATION: (10)..(10)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (11)..(11)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (13)..(13)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (14)..(14)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (16)..(16)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (17)..(17)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (19)..(19)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (20)..(20)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (22)..(22)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (23)..(23)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (25)..(25)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (26)..(26)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (28)..(28)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (29)..(29)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (31)..(31)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (32)..(32)
<223> OTHER INFORMATION: Pro, 4R-hydroxyproline, fluoroproline,
      chloroproline, Lys, Cys or Met
<220> FEATURE:
```

```
<221> NAME/KEY: MOD_RES
<222> LOCATION: (34)..(34)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (35)..(35)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (37)..(37)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (38)..(38)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (40)..(40)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (41)..(41)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (43)..(43)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (44)..(44)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (46)..(46)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (47)..(47)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (49)..(49)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (50)..(50)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (52)..(52)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (53)..(53)
<223> OTHER INFORMATION: Pro, 4R-hydroxyproline, fluoroproline,
      chloroproline, Lys, Cys or Met
<220> FEATURE:
<221> NAME/KEY: MOD_RES
<222> LOCATION: (55)..(55)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (56)..(56)
<223> OTHER INFORMATION: Pro, 4R-hydroxyproline, fluoroproline,
      chloroproline, Lys, Cys or Met
```

```
<220> FEATURE:
<221> NAME/KEY: MOD_RES
<222> LOCATION: (58)..(58)
<223> OTHER INFORMATION: Pro, 4S-hydroxyproline, fluoroproline,
      chloroproline, Lys, Cys or Met
<220> FEATURE:
<221> NAME/KEY: MOD_RES
<222> LOCATION: (59)..(59)
<223> OTHER INFORMATION: Pro, 4R-hydroxyproline, fluoroproline,
      chloroproline, Lys, Cys or Met
<220> FEATURE:
<221> NAME/KEY: MISC_FEATURE
<222> LOCATION: (1)..(60)
<223> OTHER INFORMATION: This sequence may encompass 1-20 "Xaa Xaa Gly"
      repeating units wherein Xaa is Pro, 4S-hydroxyproline,
      4R-hydroxyproline, fluoroproline, chloroproline, Lys, Cys or Met
<220> FEATURE:
<223> OTHER INFORMATION: See specification as filed for detailed
      description of substitutions and preferred embodiments

<400> SEQUENCE: 398

Xaa Xaa Gly Xaa Xaa Gly Xaa Xaa Gly Xaa Xaa Gly Xaa Xaa Gly Xaa
1               5                   10                  15

Xaa Gly Xaa Xaa Gly Xaa Xaa Gly Xaa Xaa Gly Xaa Xaa Gly Xaa Xaa
            20                  25                  30

Gly Xaa Xaa Gly Xaa Xaa Gly Xaa Xaa Gly Xaa Xaa Gly Xaa Xaa Gly
        35                  40                  45

Xaa Xaa Gly Xaa Xaa Gly Xaa Xaa Gly Xaa Xaa Gly
    50                  55                  60

<210> SEQ ID NO 399
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4S-hydroxyproline
<220> FEATURE:
<221> NAME/KEY: MOD_RES
<222> LOCATION: (8)..(8)
<223> OTHER INFORMATION: 4S-hydroxyproline
<220> FEATURE:
<221> NAME/KEY: MOD_RES
<222> LOCATION: (11)..(11)
<223> OTHER INFORMATION: 4S-hydroxyproline
<220> FEATURE:
<221> NAME/KEY: MOD_RES
<222> LOCATION: (14)..(14)
<223> OTHER INFORMATION: 4S-hydroxyproline
<220> FEATURE:
<221> NAME/KEY: MOD_RES
<222> LOCATION: (17)..(17)
<223> OTHER INFORMATION: 4S-hydroxyproline
<220> FEATURE:
<221> NAME/KEY: MOD_RES
<222> LOCATION: (20)..(20)
<223> OTHER INFORMATION: 4S-hydroxyproline
<220> FEATURE:
<221> NAME/KEY: MOD_RES
<222> LOCATION: (23)..(23)
<223> OTHER INFORMATION: 4S-hydroxyproline

<400> SEQUENCE: 399

Gly Gly Gly Pro Pro Gly Pro Pro Gly Pro Pro Gly Pro Pro Gly Pro
1               5                   10                  15

Pro Gly Pro Pro Gly Pro Pro Gly
            20
```

```
<210> SEQ ID NO 400
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline
<220> FEATURE:
<221> NAME/KEY: MOD_RES
<222> LOCATION: (23)..(23)
<223> OTHER INFORMATION: Fluoroproline

<400> SEQUENCE: 400

Gly Gly Gly Pro Pro Gly Pro Pro Gly Pro Pro Gly Pro Pro Gly Pro
1               5                   10                  15

Pro Gly Pro Pro Gly Pro Pro Gly
            20

<210> SEQ ID NO 401
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4S-hydroxyproline
<220> FEATURE:
<221> NAME/KEY: MOD_RES
<222> LOCATION: (8)..(8)
<223> OTHER INFORMATION: 4S-hydroxyproline
<220> FEATURE:
<221> NAME/KEY: MOD_RES
<222> LOCATION: (11)..(11)
<223> OTHER INFORMATION: 4S-hydroxyproline
<220> FEATURE:
<221> NAME/KEY: MOD_RES
<222> LOCATION: (14)..(14)
<223> OTHER INFORMATION: 4S-hydroxyproline
<220> FEATURE:
<221> NAME/KEY: MOD_RES
<222> LOCATION: (17)..(17)
<223> OTHER INFORMATION: 4S-hydroxyproline
<220> FEATURE:
<221> NAME/KEY: MOD_RES
<222> LOCATION: (20)..(20)
<223> OTHER INFORMATION: 4S-hydroxyproline
<220> FEATURE:
<221> NAME/KEY: MOD_RES
```

```
<222> LOCATION: (23)..(23)
<223> OTHER INFORMATION: 4S-hydroxyproline
<220> FEATURE:
<221> NAME/KEY: MOD_RES
<222> LOCATION: (26)..(26)
<223> OTHER INFORMATION: 4S-hydroxyproline

<400> SEQUENCE: 401

Gly Gly Gly Pro Pro Gly Pro Pro Gly Pro Pro Gly Pro Pro Gly Pro
1               5                   10                  15

Pro Gly Pro Pro Gly Pro Pro Gly Pro Pro Gly
            20                  25

<210> SEQ ID NO 402
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline
<220> FEATURE:
<221> NAME/KEY: MOD_RES
<222> LOCATION: (23)..(23)
<223> OTHER INFORMATION: Fluoroproline
<220> FEATURE:
<221> NAME/KEY: MOD_RES
<222> LOCATION: (26)..(26)
<223> OTHER INFORMATION: Fluoroproline

<400> SEQUENCE: 402

Gly Gly Gly Pro Pro Gly Pro Pro Gly Pro Pro Gly Pro Pro Gly Pro
1               5                   10                  15

Pro Gly Pro Pro Gly Pro Pro Gly Pro Pro Gly
            20                  25

<210> SEQ ID NO 403
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: 4S-hydroxyproline
<220> FEATURE:
<221> NAME/KEY: MOD_RES
<222> LOCATION: (8)..(8)
```

```
<223> OTHER INFORMATION: 4S-hydroxyproline
<220> FEATURE:
<221> NAME/KEY: MOD_RES
<222> LOCATION: (11)..(11)
<223> OTHER INFORMATION: 4S-hydroxyproline
<220> FEATURE:
<221> NAME/KEY: MOD_RES
<222> LOCATION: (14)..(14)
<223> OTHER INFORMATION: 4S-hydroxyproline
<220> FEATURE:
<221> NAME/KEY: MOD_RES
<222> LOCATION: (17)..(17)
<223> OTHER INFORMATION: 4S-hydroxyproline
<220> FEATURE:
<221> NAME/KEY: MOD_RES
<222> LOCATION: (20)..(20)
<223> OTHER INFORMATION: 4S-hydroxyproline
<220> FEATURE:
<221> NAME/KEY: MOD_RES
<222> LOCATION: (23)..(23)
<223> OTHER INFORMATION: 4S-hydroxyproline
<220> FEATURE:
<221> NAME/KEY: MOD_RES
<222> LOCATION: (26)..(26)
<223> OTHER INFORMATION: 4S-hydroxyproline
<220> FEATURE:
<221> NAME/KEY: MOD_RES
<222> LOCATION: (29)..(29)
<223> OTHER INFORMATION: 4S-hydroxyproline

<400> SEQUENCE: 403

Gly Gly Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly
            20                  25                  30

<210> SEQ ID NO 404
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline
<220> FEATURE:
<221> NAME/KEY: MOD_RES
<222> LOCATION: (23)..(23)
<223> OTHER INFORMATION: Fluoroproline
<220> FEATURE:
<221> NAME/KEY: MOD_RES
<222> LOCATION: (26)..(26)
<223> OTHER INFORMATION: Fluoroproline
<220> FEATURE:
```

```
<221> NAME/KEY: MOD_RES
<222> LOCATION: (29)..(29)
<223> OTHER INFORMATION: Fluoroproline

<400> SEQUENCE: 404

Gly Gly Gly Pro Pro Gly Pro Pro Gly Pro Pro Gly Pro Pro Gly Pro
1               5                   10                  15

Pro Gly Pro Pro Gly Pro Pro Gly Pro Pro Gly Pro Pro Gly
            20                  25                  30

<210> SEQ ID NO 405
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 4S-hydroxyproline
<220> FEATURE:
<221> NAME/KEY: MOD_RES
<222> LOCATION: (5)..(5)
<223> OTHER INFORMATION: 4S-hydroxyproline
<220> FEATURE:
<221> NAME/KEY: MOD_RES
<222> LOCATION: (8)..(8)
<223> OTHER INFORMATION: 4S-hydroxyproline
<220> FEATURE:
<221> NAME/KEY: MOD_RES
<222> LOCATION: (11)..(11)
<223> OTHER INFORMATION: 4S-hydroxyproline
<220> FEATURE:
<221> NAME/KEY: MOD_RES
<222> LOCATION: (14)..(14)
<223> OTHER INFORMATION: 4S-hydroxyproline
<220> FEATURE:
<221> NAME/KEY: MOD_RES
<222> LOCATION: (17)..(17)
<223> OTHER INFORMATION: 4S-hydroxyproline

<400> SEQUENCE: 405

Pro Pro Gly Pro Pro Gly Pro Pro Gly Pro Pro Gly Pro Pro Gly Pro
1               5                   10                  15

Pro Gly Tyr

<210> SEQ ID NO 406
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
```

```
<223> OTHER INFORMATION: Fluoroproline
<220> FEATURE:
<221> NAME/KEY: MOD_RES
<222> LOCATION: (17)..(17)
<223> OTHER INFORMATION: Fluoroproline

<400> SEQUENCE: 406

Pro Pro Gly Pro Pro Gly Pro Pro Gly Pro Pro Gly Pro Pro Gly Pro
1               5                   10                  15

Pro Gly Tyr

<210> SEQ ID NO 407
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 4S-hydroxyproline
<220> FEATURE:
<221> NAME/KEY: MOD_RES
<222> LOCATION: (5)..(5)
<223> OTHER INFORMATION: 4S-hydroxyproline
<220> FEATURE:
<221> NAME/KEY: MOD_RES
<222> LOCATION: (8)..(8)
<223> OTHER INFORMATION: 4S-hydroxyproline
<220> FEATURE:
<221> NAME/KEY: MOD_RES
<222> LOCATION: (11)..(11)
<223> OTHER INFORMATION: 4S-hydroxyproline
<220> FEATURE:
<221> NAME/KEY: MOD_RES
<222> LOCATION: (14)..(14)
<223> OTHER INFORMATION: 4S-hydroxyproline
<220> FEATURE:
<221> NAME/KEY: MOD_RES
<222> LOCATION: (17)..(17)
<223> OTHER INFORMATION: 4S-hydroxyproline
<220> FEATURE:
<221> NAME/KEY: MOD_RES
<222> LOCATION: (20)..(20)
<223> OTHER INFORMATION: 4S-hydroxyproline

<400> SEQUENCE: 407

Pro Pro Gly Pro Pro Gly Pro Pro Gly Pro Pro Gly Pro Pro Gly Pro
1               5                   10                  15

Pro Gly Pro Pro Gly Tyr
            20

<210> SEQ ID NO 408
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
```

```
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 408

Pro Pro Gly Pro Pro Gly Pro Pro Gly Pro Pro Gly Pro Pro Gly Pro
1               5                   10                  15

Pro Gly Pro Pro Gly Tyr
            20

<210> SEQ ID NO 409
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 4S-hydroxyproline
<220> FEATURE:
<221> NAME/KEY: MOD_RES
<222> LOCATION: (5)..(5)
<223> OTHER INFORMATION: 4S-hydroxyproline
<220> FEATURE:
<221> NAME/KEY: MOD_RES
<222> LOCATION: (8)..(8)
<223> OTHER INFORMATION: 4S-hydroxyproline
<220> FEATURE:
<221> NAME/KEY: MOD_RES
<222> LOCATION: (11)..(11)
<223> OTHER INFORMATION: 4S-hydroxyproline
<220> FEATURE:
<221> NAME/KEY: MOD_RES
<222> LOCATION: (14)..(14)
<223> OTHER INFORMATION: 4S-hydroxyproline
<220> FEATURE:
<221> NAME/KEY: MOD_RES
<222> LOCATION: (17)..(17)
<223> OTHER INFORMATION: 4S-hydroxyproline
<220> FEATURE:
<221> NAME/KEY: MOD_RES
<222> LOCATION: (20)..(20)
<223> OTHER INFORMATION: 4S-hydroxyproline
<220> FEATURE:
<221> NAME/KEY: MOD_RES
<222> LOCATION: (23)..(23)
<223> OTHER INFORMATION: 4S-hydroxyproline

<400> SEQUENCE: 409

Pro Pro Gly Pro Pro Gly Pro Pro Gly Pro Pro Gly Pro Pro Gly Pro
1               5                   10                  15

Pro Gly Pro Pro Gly Pro Pro Gly Tyr
            20                  25

<210> SEQ ID NO 410
<211> LENGTH: 25
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fluoroproline
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline
<220> FEATURE:
<221> NAME/KEY: MOD_RES
<222> LOCATION: (23)..(23)
<223> OTHER INFORMATION: Fluoroproline

<400> SEQUENCE: 410

Pro Pro Gly Pro Pro Gly Pro Pro Gly Pro Pro Gly Pro Pro Gly Pro
1               5                   10                  15

Pro Gly Pro Pro Gly Pro Pro Gly Tyr
            20                  25

<210> SEQ ID NO 411
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4S-hydroxyproline
<220> FEATURE:
<221> NAME/KEY: MOD_RES
<222> LOCATION: (6)..(6)
<223> OTHER INFORMATION: 4S-hydroxyproline
<220> FEATURE:
<221> NAME/KEY: MOD_RES
<222> LOCATION: (9)..(9)
<223> OTHER INFORMATION: 4S-hydroxyproline

<400> SEQUENCE: 411

Cys Pro Pro Gly Pro Pro Gly Pro Pro Gly
1               5                   10

<210> SEQ ID NO 412
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)..(3)
<223> OTHER INFORMATION: Fluoroproline
<220> FEATURE:
<221> NAME/KEY: MOD_RES
<222> LOCATION: (6)..(6)
<223> OTHER INFORMATION: Fluoroproline
<220> FEATURE:
<221> NAME/KEY: MOD_RES
<222> LOCATION: (9)..(9)
<223> OTHER INFORMATION: Fluoroproline

<400> SEQUENCE: 412

Cys Pro Pro Gly Pro Pro Gly Pro Pro Gly
1               5                   10

<210> SEQ ID NO 413
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4S-hydroxyproline
<220> FEATURE:
<221> NAME/KEY: MOD_RES
<222> LOCATION: (6)..(6)
<223> OTHER INFORMATION: 4S-hydroxyproline
<220> FEATURE:
<221> NAME/KEY: MOD_RES
<222> LOCATION: (9)..(9)
<223> OTHER INFORMATION: 4S-hydroxyproline
<220> FEATURE:
<221> NAME/KEY: MOD_RES
<222> LOCATION: (12)..(12)
<223> OTHER INFORMATION: 4S-hydroxyproline
<220> FEATURE:
<221> NAME/KEY: MOD_RES
<222> LOCATION: (15)..(15)
<223> OTHER INFORMATION: 4S-hydroxyproline

<400> SEQUENCE: 413

Cys Pro Pro Gly Pro Pro Gly Pro Pro Gly Pro Pro Gly Pro Pro Gly
1               5                   10                  15

<210> SEQ ID NO 414
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Fluoroproline
<220> FEATURE:
<221> NAME/KEY: MOD_RES
<222> LOCATION: (6)..(6)
<223> OTHER INFORMATION: Fluoroproline
<220> FEATURE:
<221> NAME/KEY: MOD_RES
<222> LOCATION: (9)..(9)
<223> OTHER INFORMATION: Fluoroproline
<220> FEATURE:
<221> NAME/KEY: MOD_RES
<222> LOCATION: (12)..(12)
<223> OTHER INFORMATION: Fluoroproline
<220> FEATURE:
<221> NAME/KEY: MOD_RES
<222> LOCATION: (15)..(15)
<223> OTHER INFORMATION: Fluoroproline
```

-continued

<400> SEQUENCE: 414

Cys Pro Pro Gly Pro Pro Gly Pro Pro Gly Pro Pro Gly Pro Pro Gly
1               5                   10                  15

<210> SEQ ID NO 415
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4S-hydroxyproline
<220> FEATURE:
<221> NAME/KEY: MOD_RES
<222> LOCATION: (6)..(6)
<223> OTHER INFORMATION: 4S-hydroxyproline
<220> FEATURE:
<221> NAME/KEY: MOD_RES
<222> LOCATION: (9)..(9)
<223> OTHER INFORMATION: 4S-hydroxyproline
<220> FEATURE:
<221> NAME/KEY: MOD_RES
<222> LOCATION: (12)..(12)
<223> OTHER INFORMATION: 4S-hydroxyproline
<220> FEATURE:
<221> NAME/KEY: MOD_RES
<222> LOCATION: (15)..(15)
<223> OTHER INFORMATION: 4S-hydroxyproline
<220> FEATURE:
<221> NAME/KEY: MOD_RES
<222> LOCATION: (18)..(18)
<223> OTHER INFORMATION: 4S-hydroxyproline
<220> FEATURE:
<221> NAME/KEY: MOD_RES
<222> LOCATION: (21)..(21)
<223> OTHER INFORMATION: 4S-hydroxyproline

<400> SEQUENCE: 415

Cys Pro Pro Gly Pro Pro Gly Pro Pro Gly Pro Pro Gly Pro Pro Gly
1               5                   10                  15

Pro Pro Gly Pro Pro Gly
            20

<210> SEQ ID NO 416
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Fluoroproline
<220> FEATURE:
<221> NAME/KEY: MOD_RES
<222> LOCATION: (6)..(6)
<223> OTHER INFORMATION: Fluoroproline
<220> FEATURE:
<221> NAME/KEY: MOD_RES
<222> LOCATION: (9)..(9)
<223> OTHER INFORMATION: Fluoroproline
<220> FEATURE:
<221> NAME/KEY: MOD_RES
<222> LOCATION: (12)..(12)
<223> OTHER INFORMATION: Fluoroproline
<220> FEATURE:
<221> NAME/KEY: MOD_RES
<222> LOCATION: (15)..(15)
<223> OTHER INFORMATION: Fluoroproline
<220> FEATURE:

<221> NAME/KEY: MOD_RES
<222> LOCATION: (18)..(18)
<223> OTHER INFORMATION: Fluoroproline
<220> FEATURE:
<221> NAME/KEY: MOD_RES
<222> LOCATION: (21)..(21)
<223> OTHER INFORMATION: Fluoroproline

<400> SEQUENCE: 416

Cys Pro Pro Gly Pro Pro Gly Pro Pro Gly Pro Pro Gly Pro Pro Gly
1               5                   10                  15

Pro Pro Gly Pro Pro Gly
            20

<210> SEQ ID NO 417
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4S-hydroxyproline
<220> FEATURE:
<221> NAME/KEY: MOD_RES
<222> LOCATION: (8)..(8)
<223> OTHER INFORMATION: 4S-hydroxyproline
<220> FEATURE:
<221> NAME/KEY: MOD_RES
<222> LOCATION: (11)..(11)
<223> OTHER INFORMATION: 4S-hydroxyproline
<220> FEATURE:
<221> NAME/KEY: MOD_RES
<222> LOCATION: (14)..(14)
<223> OTHER INFORMATION: 4S-hydroxyproline
<220> FEATURE:
<221> NAME/KEY: MOD_RES
<222> LOCATION: (17)..(17)
<223> OTHER INFORMATION: 4S-hydroxyproline
<220> FEATURE:
<221> NAME/KEY: MOD_RES
<222> LOCATION: (20)..(20)
<223> OTHER INFORMATION: 4S-hydroxyproline

<400> SEQUENCE: 417

Gly Gly Gly Pro Pro Gly Pro Pro Gly Pro Pro Gly Pro Pro Gly Pro
1               5                   10                  15

Pro Gly Pro Pro Gly
            20

<210> SEQ ID NO 418
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fluoroproline
<220> FEATURE:
<221> NAME/KEY: MOD_RES
<222> LOCATION: (8)..(8)
<223> OTHER INFORMATION: Fluoroproline
<220> FEATURE:
<221> NAME/KEY: MOD_RES
<222> LOCATION: (11)..(11)
<223> OTHER INFORMATION: Fluoroproline
<220> FEATURE:
<221> NAME/KEY: MOD_RES

```
<222> LOCATION: (14)..(14)
<223> OTHER INFORMATION: Fluoroproline
<220> FEATURE:
<221> NAME/KEY: MOD_RES
<222> LOCATION: (17)..(17)
<223> OTHER INFORMATION: Fluoroproline
<220> FEATURE:
<221> NAME/KEY: MOD_RES
<222> LOCATION: (20)..(20)
<223> OTHER INFORMATION: Fluoroproline

<400> SEQUENCE: 418

Gly Gly Gly Pro Pro Gly Pro Pro Gly Pro Pro Gly Pro Pro Gly Pro
1               5                   10                  15

Pro Gly Pro Pro Gly
            20

<210> SEQ ID NO 419
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Chloroproline
<220> FEATURE:
<221> NAME/KEY: MOD_RES
<222> LOCATION: (5)..(5)
<223> OTHER INFORMATION: Chloroproline
<220> FEATURE:
<221> NAME/KEY: MOD_RES
<222> LOCATION: (8)..(8)
<223> OTHER INFORMATION: Chloroproline
<220> FEATURE:
<221> NAME/KEY: MOD_RES
<222> LOCATION: (11)..(11)
<223> OTHER INFORMATION: Chloroproline
<220> FEATURE:
<221> NAME/KEY: MOD_RES
<222> LOCATION: (14)..(14)
<223> OTHER INFORMATION: Chloroproline
<220> FEATURE:
<221> NAME/KEY: MOD_RES
<222> LOCATION: (17)..(17)
<223> OTHER INFORMATION: Chloroproline
<220> FEATURE:
<221> NAME/KEY: MOD_RES
<222> LOCATION: (20)..(20)
<223> OTHER INFORMATION: Chloroproline

<400> SEQUENCE: 419

Pro Pro Gly Pro Pro Gly Pro Pro Gly Pro Pro Gly Pro Pro Gly Pro
1               5                   10                  15

Pro Gly Pro Pro Gly Arg Pro Lys Pro Gln Gln Phe Phe Gly Leu Met
            20                  25                  30
```